US012780851B2

(12) United States Patent
He et al.

(10) Patent No.: US 12,780,851 B2
(45) Date of Patent: Nov. 3, 2026

(54) COMPOUND FOR EGFR KINASE INHIBITOR, COMPOSITION, AND USE THEREOF

(71) Applicant: INNOVATION INSTITUTE FOR ARTIFICIAL INTELLIGENCE IN MEDICINE OF ZHEJIANG UNIVERSITY, Hangzhou (CN)

(72) Inventors: Qiaojun He, Hangzhou (CN); Qinjie Weng, Hangzhou (CN); Binhui Chen, Hangzhou (CN); Fangjie Yan, Hangzhou (CN); Jun Mo, Hangzhou (CN); Chunxia Wu, Hangzhou (CN); Rushuang Jin, Hangzhou (CN); Liying Yan, Hangzhou (CN)

(73) Assignee: INNOVATION INSTITUTE FOR ARTIFICIAL INTELLIGENCE IN MEDICINE OF ZHEJIANG UNIVERSITY, Hangzhou (CN)

( * ) Notice: Subject to any disclaimer, the term of this patent is extended or adjusted under 35 U.S.C. 154(b) by 314 days.

(21) Appl. No.: 18/292,180

(22) PCT Filed: Jul. 29, 2022

(86) PCT No.: PCT/CN2022/109097

§ 371 (c)(1),
(2) Date: Jan. 25, 2024

(87) PCT Pub. No.: WO2023/006088

PCT Pub. Date: Feb. 2, 2023

(65) Prior Publication Data

US 2025/0101052 A1 Mar. 27, 2025

(30) Foreign Application Priority Data

Jul. 30, 2021 (CN) ......................... 202110874921.0

(51) Int. Cl.

| | |
|---|---|
| ***C07F 9/6558*** | (2006.01) |
| ***A61K 31/675*** | (2006.01) |
| ***C07F 9/6561*** | (2006.01) |

(52) U.S. Cl.

CPC ........ *C07F 9/65583* (2013.01); *A61K 31/675* (2013.01); *C07F 9/6561* (2013.01)

(58) Field of Classification Search

CPC ..................................................... C07F 9/6561

See application file for complete search history.

(56) References Cited

FOREIGN PATENT DOCUMENTS

| | | | | | |
|---|---|---|---|---|---|
| CN | 103153064 | A | 6/2013 | | |
| CN | 105330698 | A | 2/2016 | | |
| CN | 108689994 | A | 10/2018 | | |
| CN | 110305161 | A | 10/2019 | | |
| WO | 2017086832 | A1 | 5/2017 | | |
| WO | 2021018003 | A1 | 2/2021 | | |
| WO | WO 2022/211573 | * | 10/2022 | ........... | C07D 401/12 |
| WO | 2023006088 | A1 | 2/2023 | | |

OTHER PUBLICATIONS

PCT/CN2022/109097—International Search Report and Written Opinion mailed on Oct. 12, 2022, 12 pages.

* cited by examiner

*Primary Examiner* — Alicia L Otton

(74) *Attorney, Agent, or Firm* — Getech Law LLC; Jun Ye

(57) ABSTRACT

Disclosed is a compound having a structure in formula I. The compound of the present invention has good enzyme inhibitory activity against EGFR mutants (L858R/T790M/C797S, del19/T790M/C797S, del19/C797S, L858R/C797S), a weak inhibitory effect on wild-type EGFR, and good selectivity. The compound has significant inhibitory activity against the proliferation of EGFR mutant cells, and has potential application value in the treatment of diseases related to cell proliferation. The compound of the present invention has good solubility and permeability, good in-vivo metabolic stability, high in-vivo exposure, and high bioavailability, and is a potential pharmaceutical compound.

9 Claims, 1 Drawing Sheet

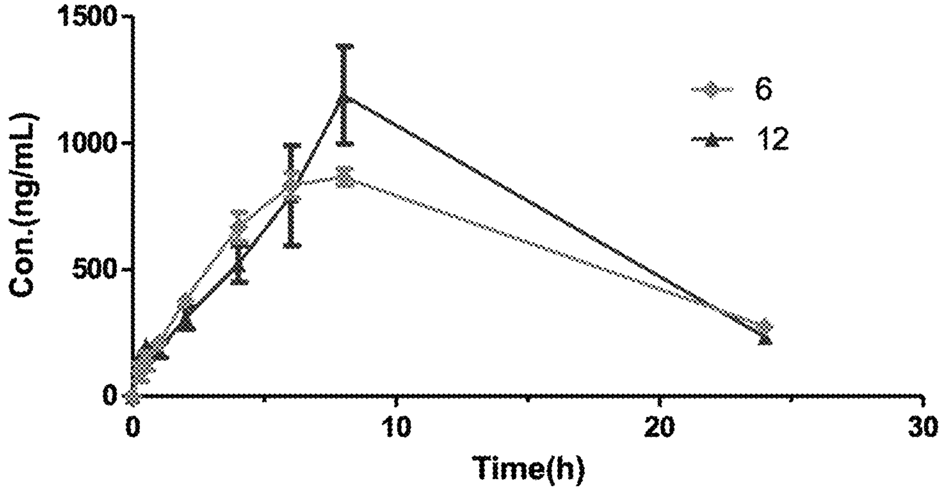
1500
1000
500
0
Con.(ng/mL)
0
10
20
30
Time(h)
6
12

COMPOUND FOR EGFR KINASE INHIBITOR, COMPOSITION, AND USE THEREOF

CROSS REFERENCE OF RELATED APPLICATION

The present application is a 371 of international Application PCT/CN2022/109097, filed Jul. 29, 2022, which claims priority to Chinese Patent Application No. 202110874921.0 filed Jul. 30, 2021. The contents of the applications are incorporated herein by reference in their entireties.

FIELD OF TECHNOLOGY

The present invention belongs to the technical field of drug synthesis, and in particular to a compound for an EGFR kinase inhibitor and use thereof.

BACKGROUND

Non-small cell lung cancer (NSCLC) is one of the most malignant types of cancer worldwide, posing a serious threat to human health and life. Epidermal growth factor receptor (EGFR) is a member of the HER family and is an essential transmembrane glycoprotein in the cell signaling pathway that regulates cell proliferation, differentiation, and apoptosis. Overexpression of EGFR has been observed in various types of solid tumors, including NSCLC. Various EGFR small molecule inhibitors have been developed as drugs for the treatment of NSCLC.

The first-generation reversible EGFR inhibitors Gefitinib and Erlotinib have significant therapeutic effects on NSCLC patients with EGFR sensitive mutations. L858R point mutation and exon 19 deletion are the most common sensitive mutations that can be treated with the first-generation inhibitors. But after 12 months of clinical treatment, 50% to 60% of drug-resistant patients developed T790M mutation. The presence of T790M increases the affinity of receptors for ATP, thereby reducing the ability of EGFR inhibitors to competitively bind to receptors with ATP. Then, the second and third generations of EGFR irreversible inhibitors were developed, and mainly covalently bind to Cys797 to enhance the efficacy of cells against T790M mutants. However, due to the potentially less effective interaction between the aniline portion of the second-generation EGFR inhibitors and the Met790 side chain, the inhibitory activity against T790M mutation is lower than the activity of wild-type EGFR. The third-generation EGFR inhibitors selectively and irreversibly target EGFR T790M and other EGFR mutations. AZD9291 (Osimertinib) is the only FDA-approved third-generation inhibitor with good efficacy and minimal toxicity against EGFR T790M mutants. However, a clinical study showed that 20% to 30% of patients treated with AZD9291 developed an another point mutation C797S, which can prevent irreversible inhibitors from covalently binding to Cys797. The loss of covalent interaction leads to a significant decrease in inhibitory efficacy, which in turn leads to the development of drug resistance. At present, there is no mature treatment means for mutations that are prone to occur after resistance to Osimertinib: L858R/T790M/C797S, del19/T790M/C797S, L858R/C797S, and del19/C797S, as well as some rare mutations. The clinical demand is urgent.

Research has shown that simultaneously inhibiting EGFR and Aurora B can maximize the efficacy of BIM and PUMB mediated apoptosis to eradicate cancer cells (Cancer cell, 2021, 39(9): 1245-1261). Targeting Aurora B kinase can prevent and overcome the resistance of lung cancer to EGFR inhibitors. Therefore, combination with Aurora B inhibitors or the development of dual-target drugs with both Aurora B and EGFR inhibitory activity may become an important means to overcome resistance to EGFR inhibitors.

SUMMARY

The present invention relates to pharmaceutical active compounds and pharmaceutically acceptable salts thereof, which can be used for treating cell proliferative diseases mediated by certain mutant forms of epidermal growth factor receptors, such as cancer.

A compound, having a structure represented by formula I:

formula I

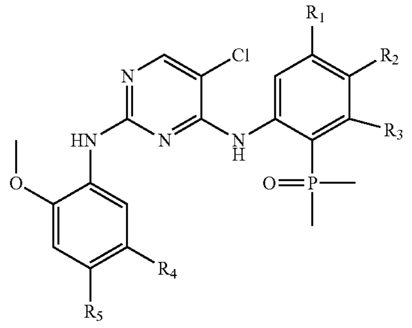

or being an isomer of the structure represented by formula I or a pharmaceutically acceptable salt thereof, wherein $R_1$, $R_2$, and $R_3$ are each independently selected from H, Cl, $C_{1-3}$ alkyl (preferably $CH_3$ and ethyl), and $CF_3$;

$R_4$ is selected from H, halogens, and $C_{1-3}$ alkyl (preferably $CH_3$ and $CH_2CH_3$);

$R_5$ is selected from

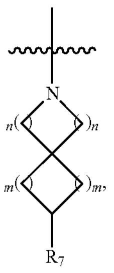

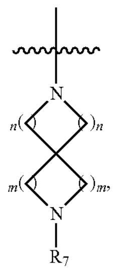

and

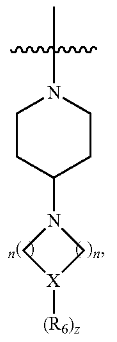

where m and n are each independently selected from 1 and 2, Z is selected from 0 or 1, and X is selected from N, O, and CH;

$R_6$ is selected from H, $C_{1-3}$ alkyl (preferably $CH_3$), and $C_{1-3}$ alkyl substituted amino (preferably

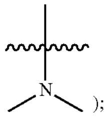

);

$R_7$ is selected from $C_{1-6}$ alkyl, $C_{1-6}$ cycloalkyl, amino, and $C_{1-6}$ alkoxy, the amino may be optionally substituted by 1 or 2 $C_{1-6}$ alkyls and $C_{1-6}$ cycloalkyl, and the $C_{1-6}$ alkyl and the $C_{1-6}$ alkoxy may be optionally substituted by 1 or more $C_{1-6}$ cycloalkyls, halogens, oxy (i.e., =o), hydroxyl, and cyano;

when X is O, z is selected from 0;

$R_1$, $R_2$, and $R_3$ are not H at the same time, and when one thereof is selected from $CH_3$, at most one of the other two is selected from H; and when both $R_2$ and $R_3$ are $CH_3$, $R_5$ is not selected from

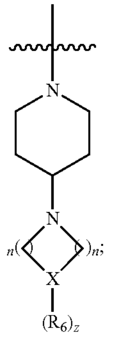

when $R_4$ is Cl, $R_5$ is not selected from

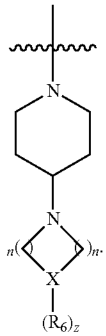

In some solutions of the present invention, the compound has a structure in formula II, an isomer thereof, or a pharmaceutically acceptable salt thereof:

formula II

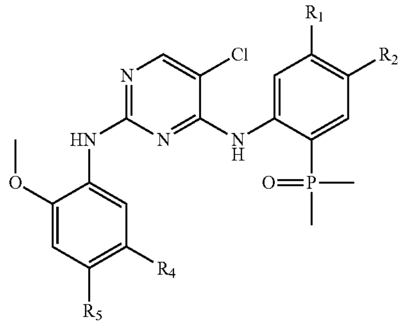

wherein $R_1$ is selected from Cl, $CH_3$, and $CF_3$;

$R_2$ is selected from H, Cl, $CH_3$, and $CF_3$;

$R_4$ is selected from H, halogens, $CH_3$, and $CH_2CH_3$;

$R_5$ is selected from

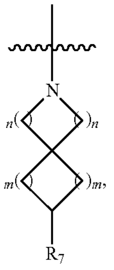

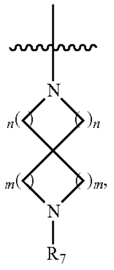

and

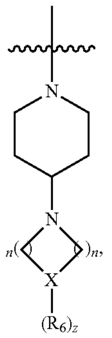

where m and n are each independently selected from 1 and 2, Z is selected from 0 or 1, and X is selected from N, O, and CH;

$R_6$ is selected from H, $CH_3$, and

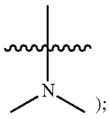

);

$R_7$ is selected from $C_{1-6}$ alkyl, $C_{1-6}$ cycloalkyl, amino, and $C_{1-6}$ alkoxy, the amino may be optionally substituted by 1 or 2 $C_{1-6}$ alkyls and $C_{1-6}$ cycloalkyl, and the $C_{1-6}$ alkyl and the $C_{1-6}$ alkoxy may be optionally substituted by 1 or more $C_{1-6}$ cycloalkyls, halogens, oxy (i.e., =o), hydroxyl, and cyano; when X is O, z is selected from 0;

when $R_2$ is H, $R_1$ is not selected from $CH_3$;

when $R_4$ is Cl, $R_5$ is not selected from

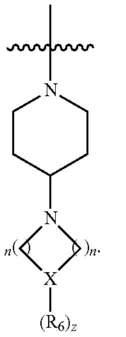

In some solutions of the present invention, the compound has a structure in formula III, an isomer thereof, or a pharmaceutically acceptable salt thereof:

formula III

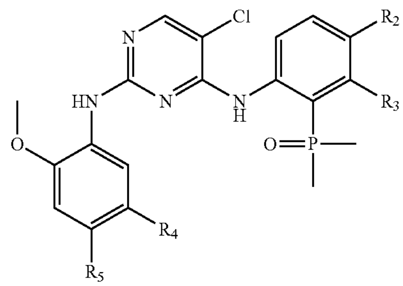

$R_2$ and $R_3$ are each independently selected from Cl and $CH_3$;

$R_4$ is selected from H, halogens, $CH_3$, and $CH_2CH_3$;

$R_5$ is selected from

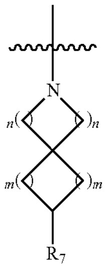

and

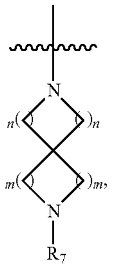

where m and n are each independently selected from 1 and 2;

$R_7$ is selected from $C_{1-6}$ alkyl, $C_{1-6}$ cycloalkyl, amino, and $C_1$-6 alkoxy, the amino may be optionally substituted by 1 or 2 $C_{1-6}$ alkyls and $C_{1-6}$ cycloalkyl, and the $C_{1-6}$ alkyl and the $C_{1-6}$ alkoxy may be optionally substituted by 1 or more $C_{1-6}$ cycloalkyls, halogens, oxy (i.e., =○), hydroxyl, and cyano.

As preferred, $R_3$ is H;

$R_1$ is selected from Cl, $CH_3$, and $CF_3$;

$R_2$ is selected from H, Cl, $CH_3$, and $CF_3$;

$R_4$ is selected from H, halogens, $CH_3$, and $CH_2CH_3$;

or $R_1$ is H;

$R_2$ and $R_3$ are each independently selected from Cl and $CH_3$;

$R_4$ is selected from H, halogens, $CH_3$, and $CH_2CH_3$.

As preferred, the $R_5$ is selected from:

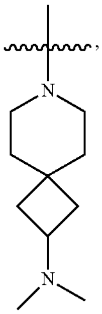
,
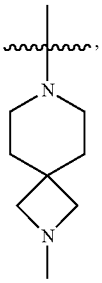
,
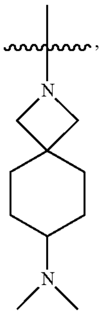
,
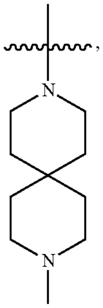
,
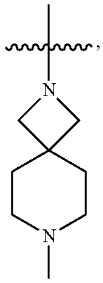
,
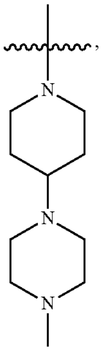
,
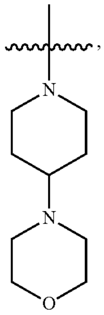
,
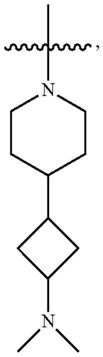
,
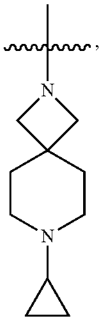
,
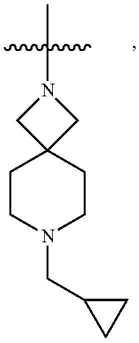
,
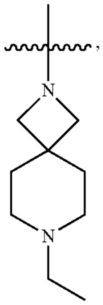
,
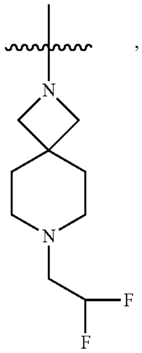
,
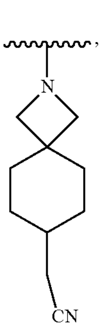
,
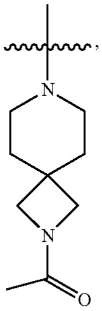
,
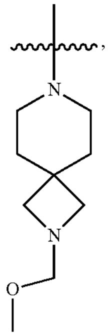
,
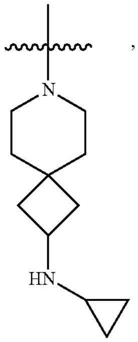
, -continued

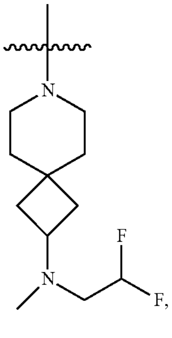 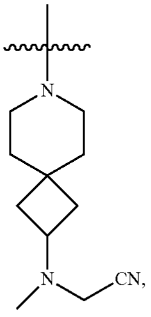 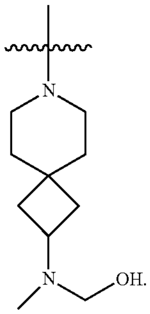

In some solutions of the present invention, for the compound, the $R_5$ is selected from:

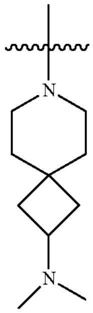, 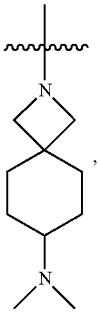, 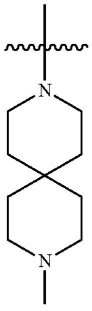, 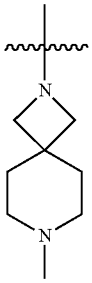,

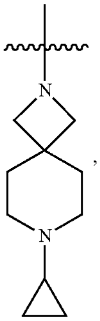, 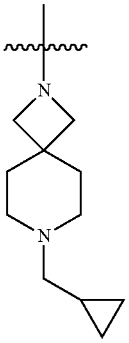, 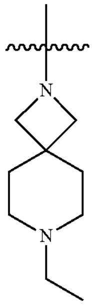, 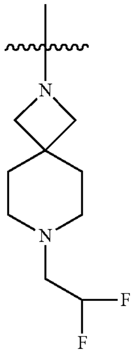,

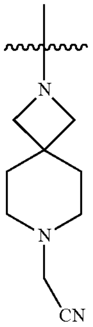, 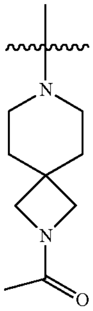, 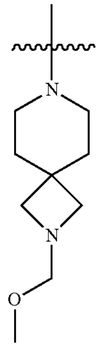, 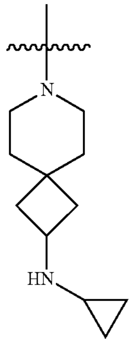,

-continued

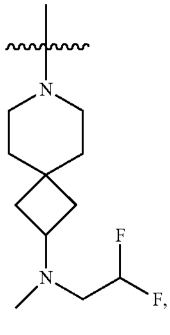 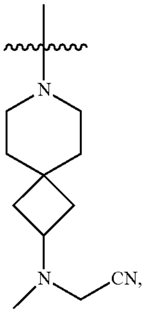 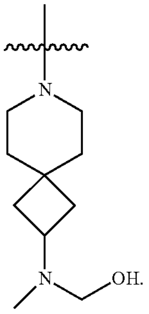

In some solutions of the present invention, the $R_1$ and the $R_2$ are each independently selected from Cl and $CH_3$.

In some solutions of the present invention, both the $R_1$ and the $R_2$ are $CH_3$ or both are Cl.

In some solutions of the present invention, both the $R_1$ and the $R_2$ are $CH_3$.

In some solutions of the present invention, both the $R_2$ and the $R_3$ are $CH_3$.

In some solutions of the present invention, when the $R_2$ is H, the $R_3$ is Cl.

As preferred, when $R_3$ is H, $R_1$ and $R_2$ are each independently selected from Cl and $CH_3$.

As preferred, when $R_3$ is H, both $R_1$ and $R_2$ are $CH_3$ or both are Cl.

As preferred, when $R_1$ is H, both $R_2$ and $R_3$ are $CH_3$.

As preferred, when $R_1$ is H and $R_2$ is H, $R_3$ is Cl.

As preferred, the compound is selected from:

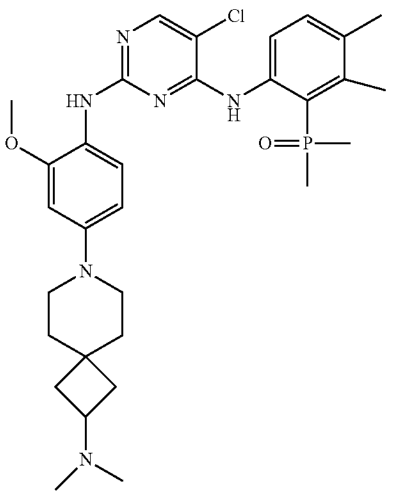

-continued
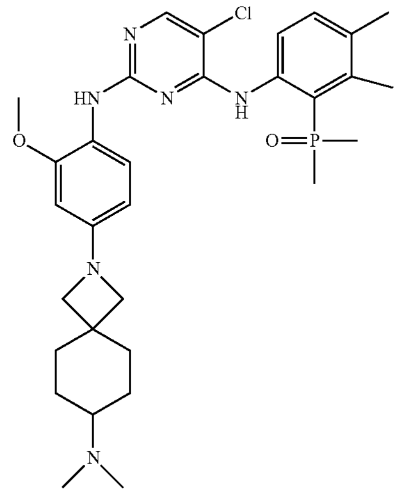
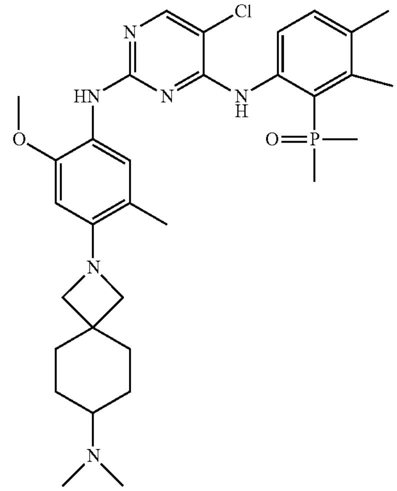
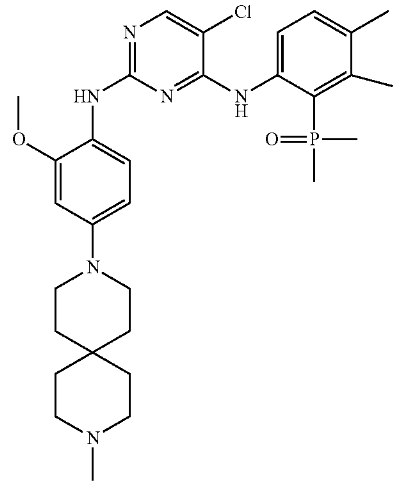
-continued
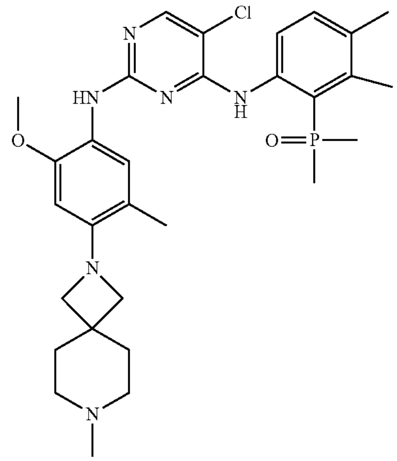
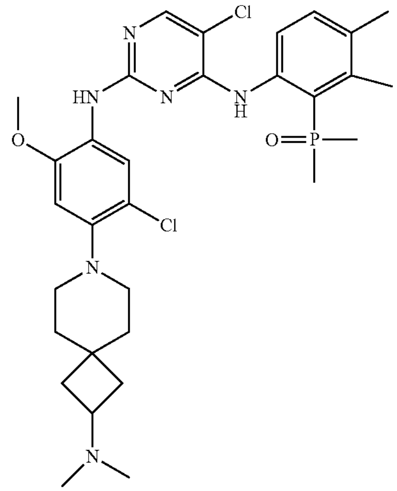
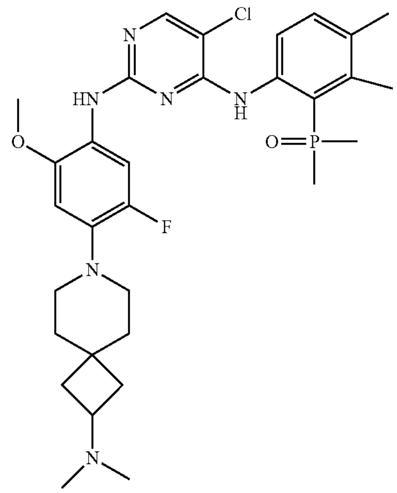

-continued
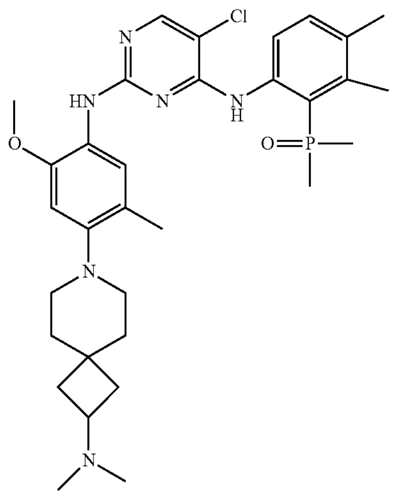
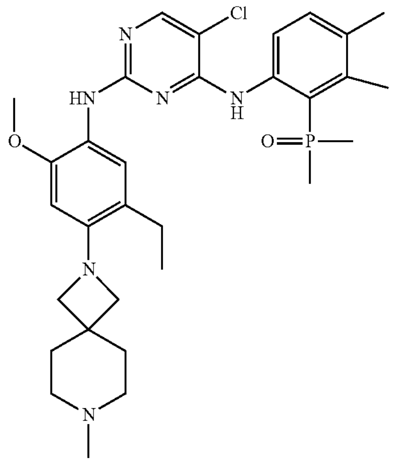
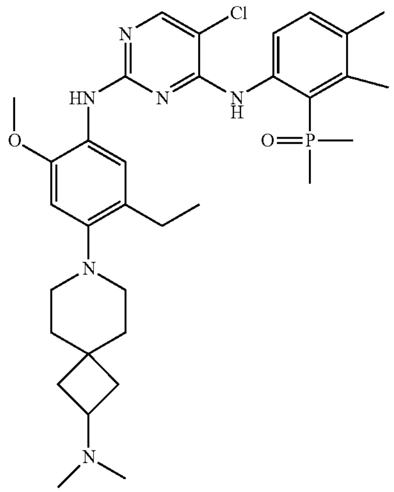
-continued
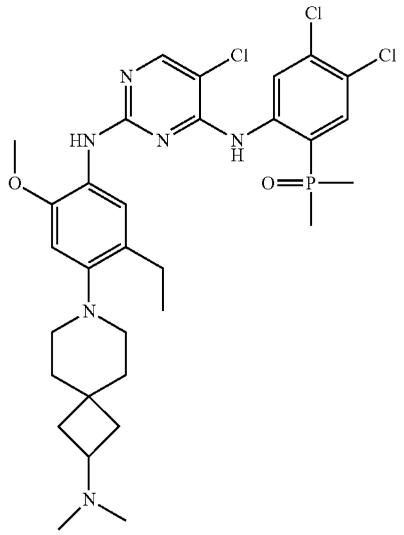
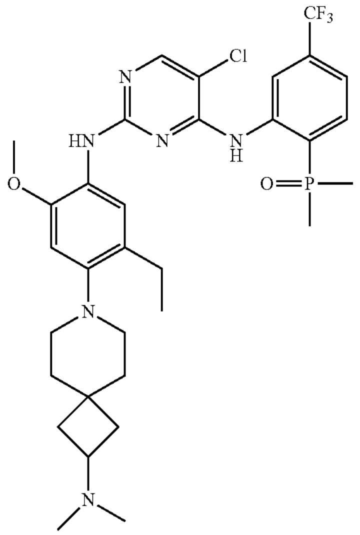
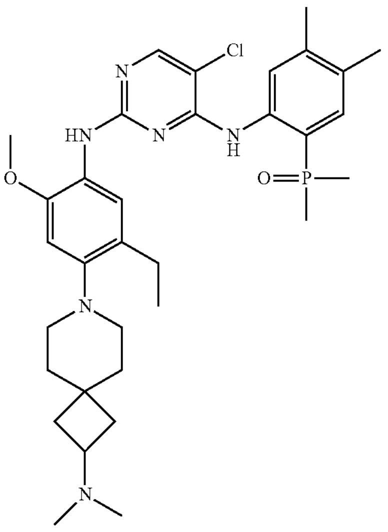

-continued
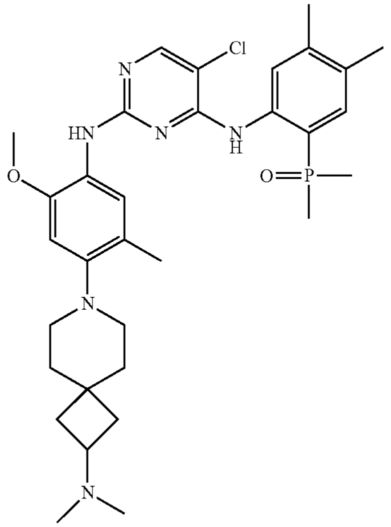
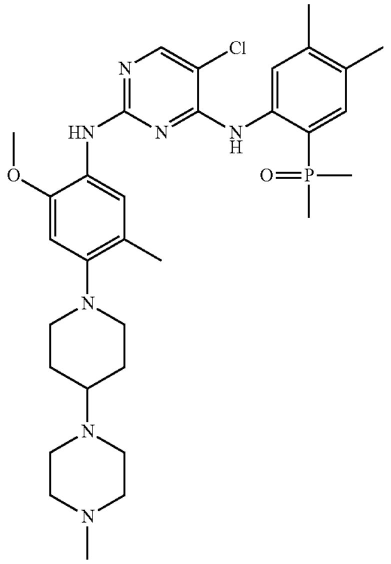
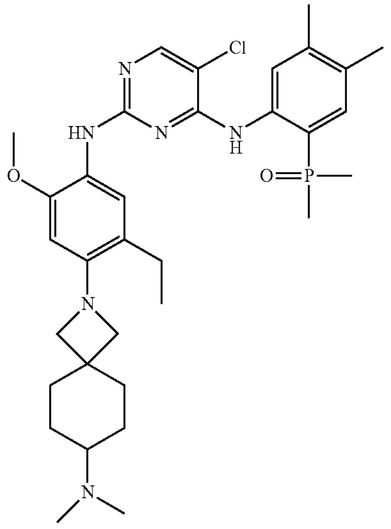
-continued
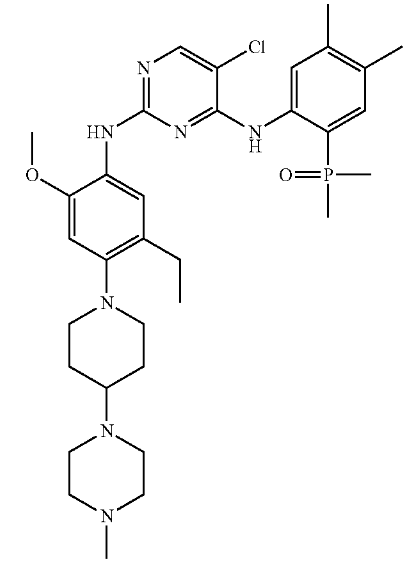
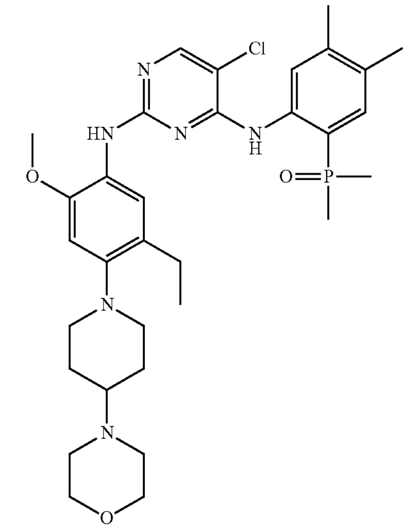
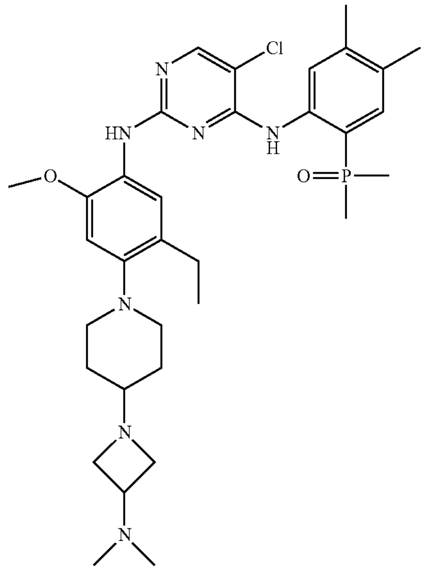

-continued
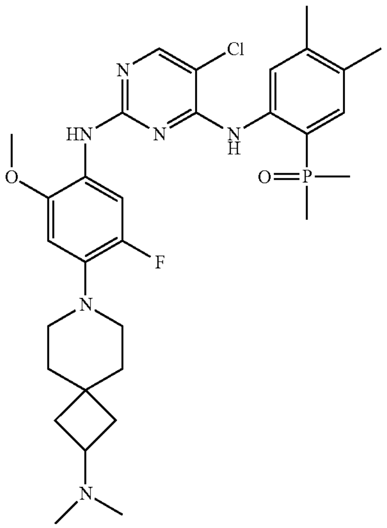
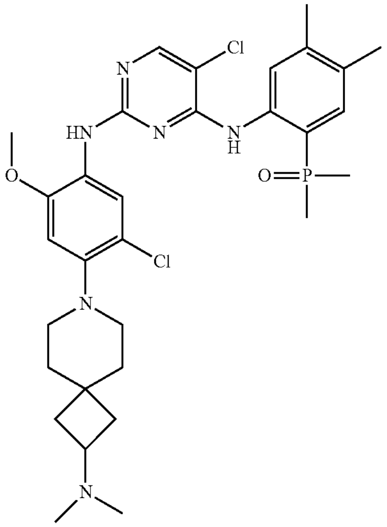
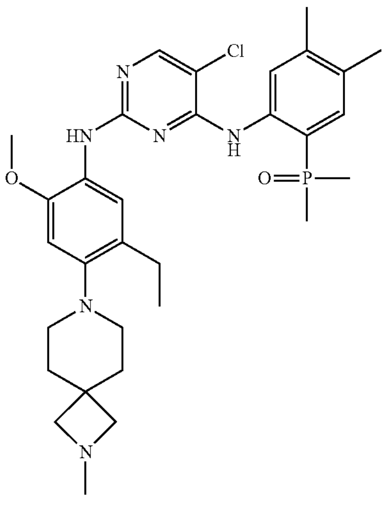
-continued
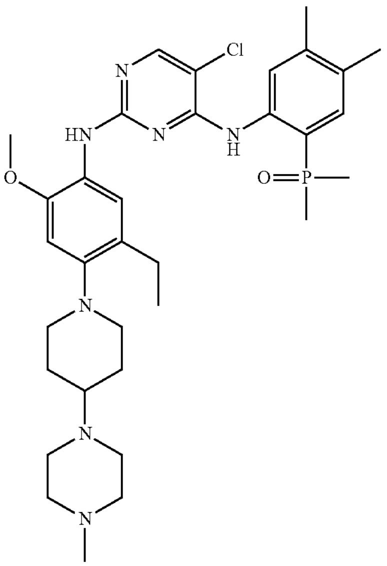
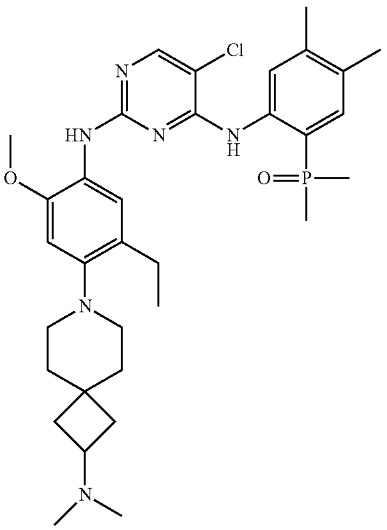
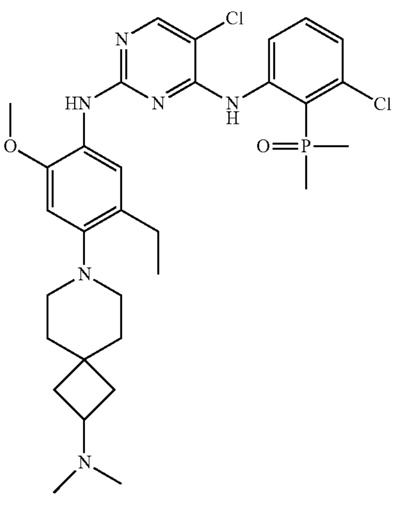

-continued
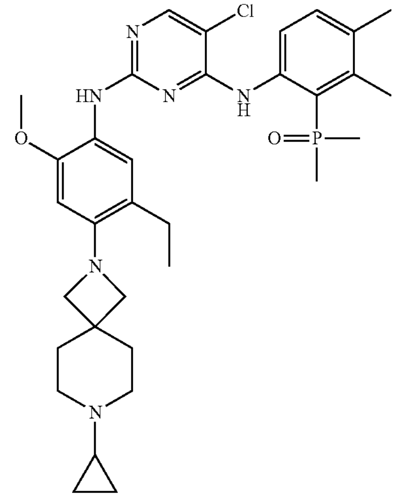
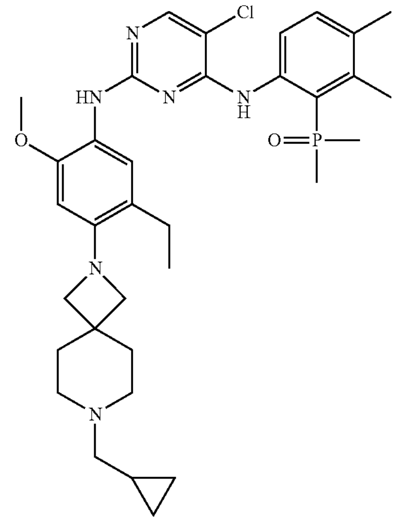
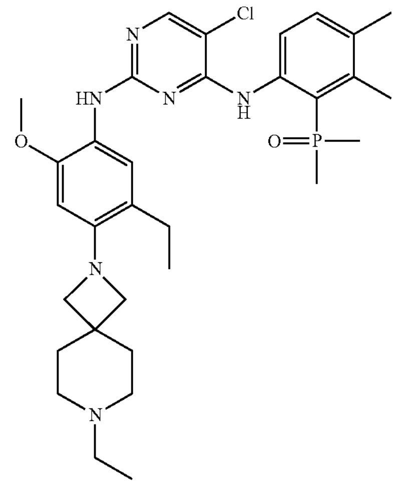
-continued
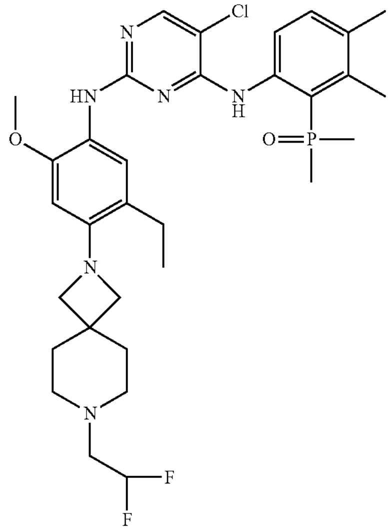
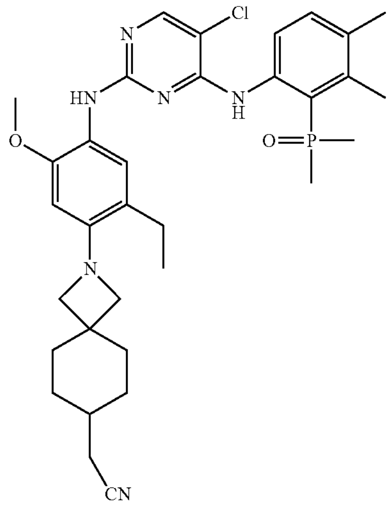
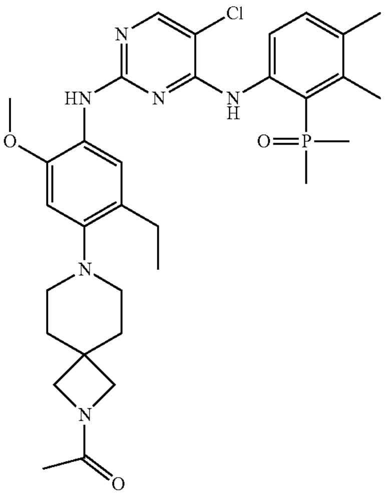

-continued
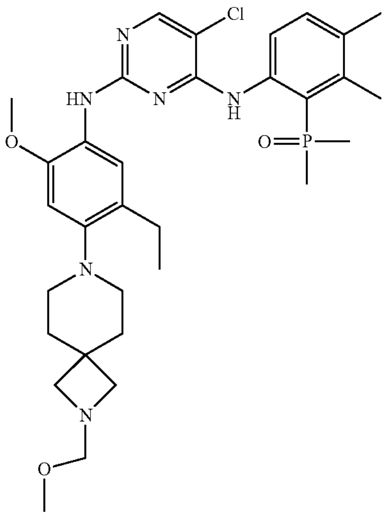
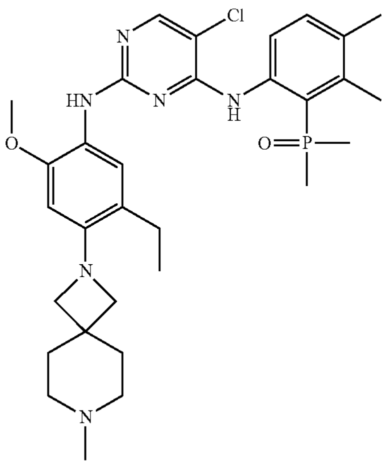
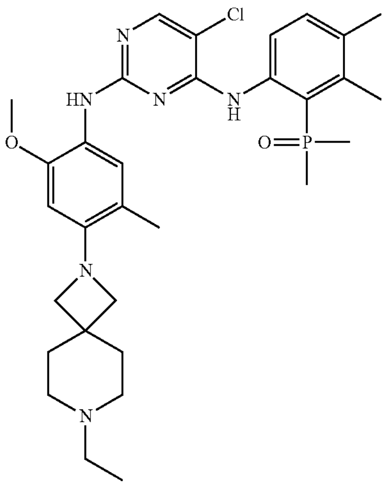
-continued
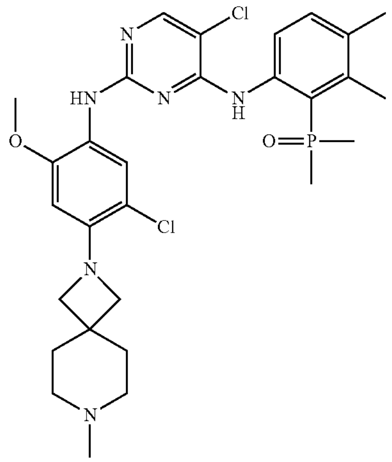
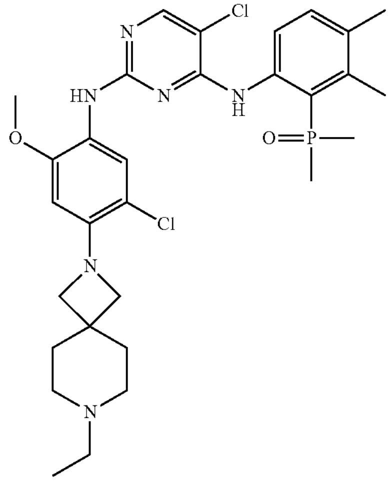
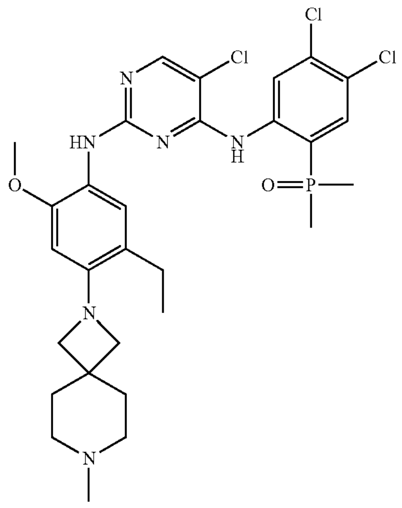

-continued
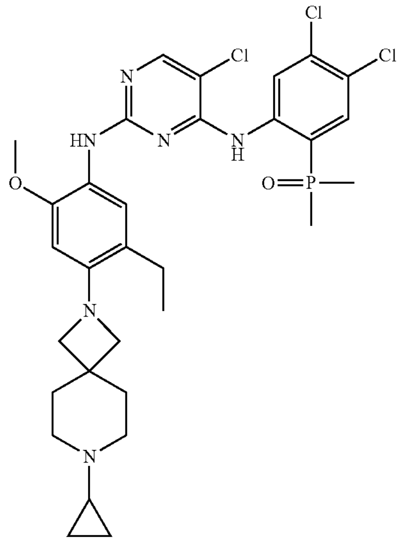
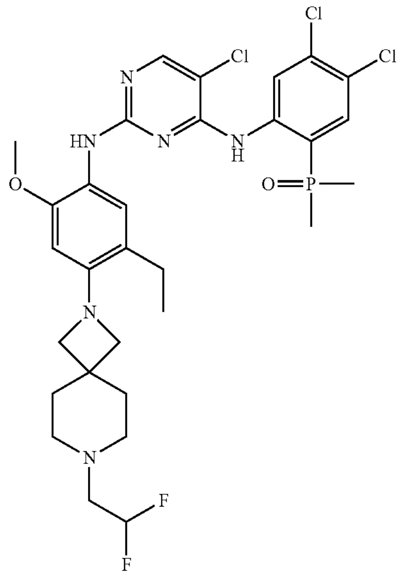
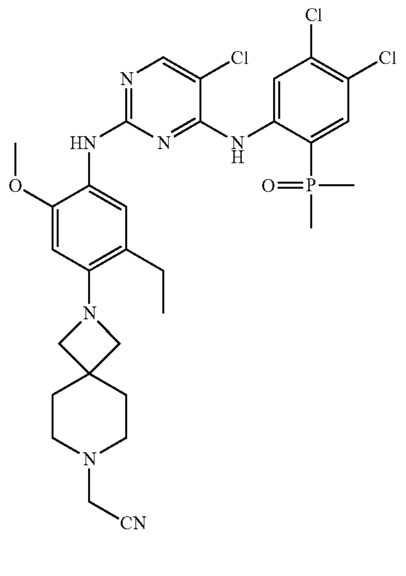
-continued
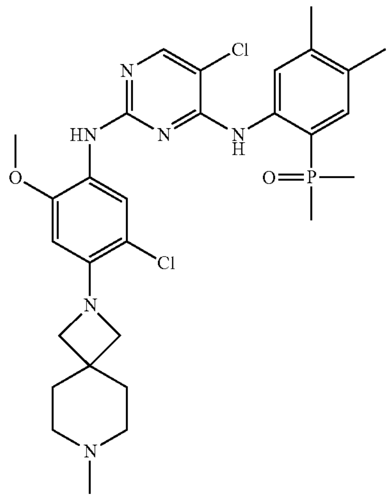
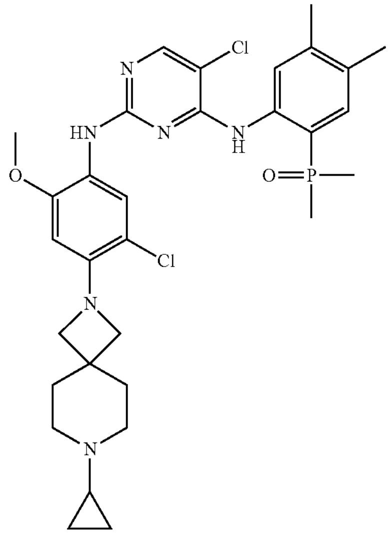
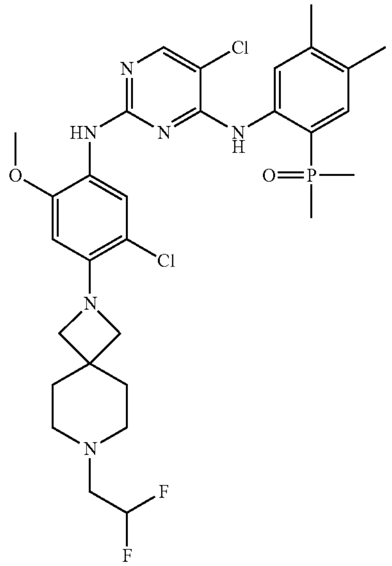

-continued
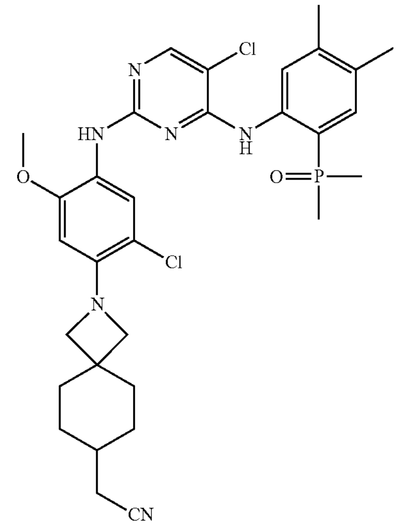
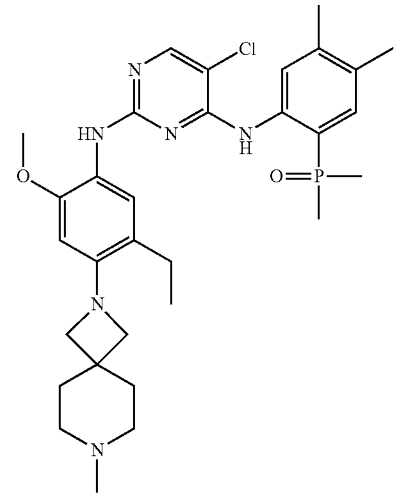
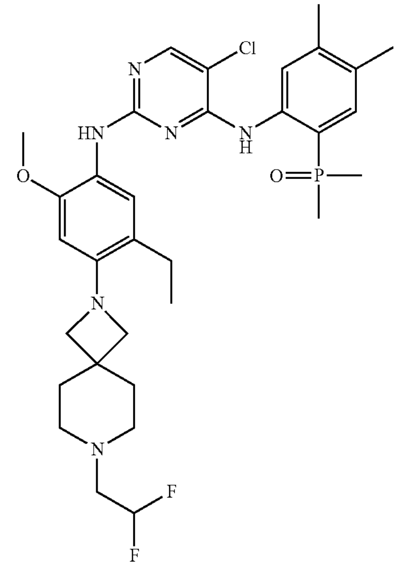
-continued
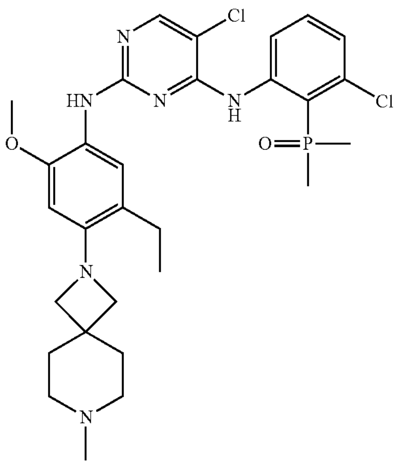
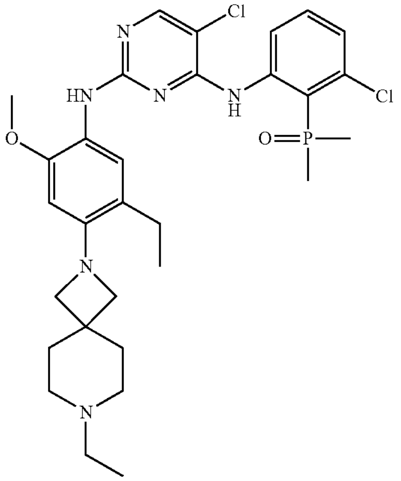
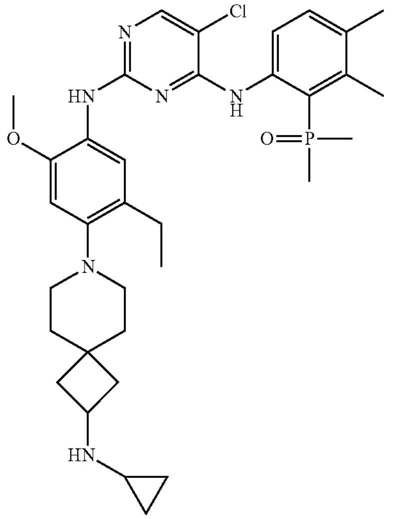

-continued

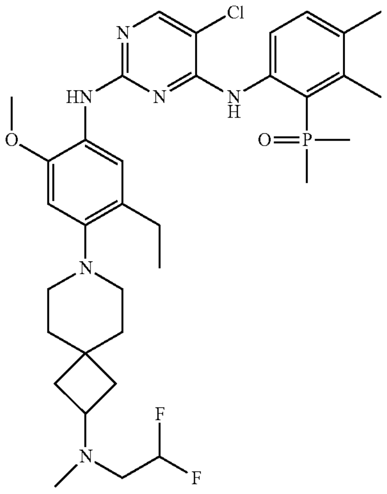

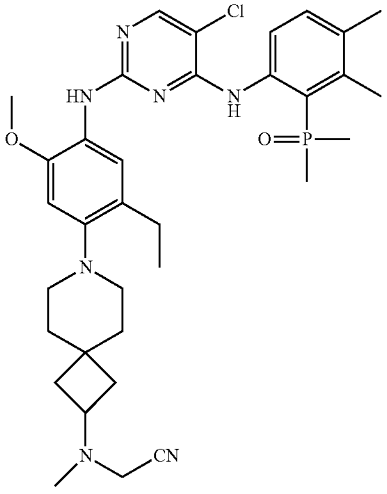 [SMILES: CCc1cc(Nc2ncc(Cl)c(Nc3ccc(C)c(C)c3P(C)(C)=O)n2)c(OC)cc1N1CCC2(CC1)CC(N(C)CO)C2]

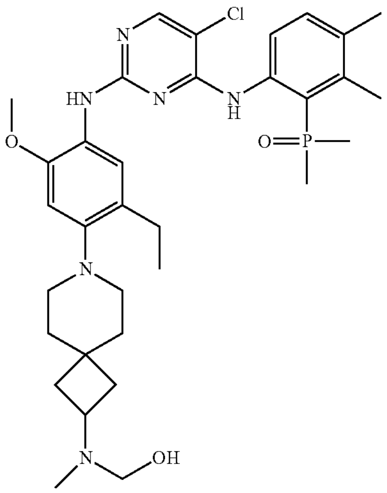

In some solutions of the present invention, provided is a compound, having a structure represented by formula IV:

formula IV

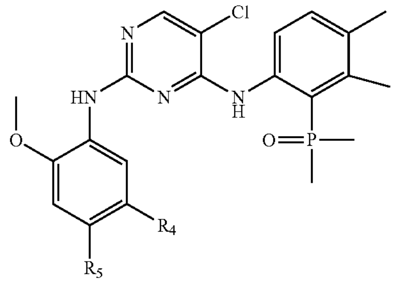

or being an isomer of the structure represented by formula IV or a pharmaceutically acceptable salt thereof, $R_4$ is selected from $C_{1-3}$ alkyl;

$R_5$ is selected from

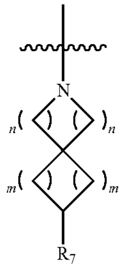
and
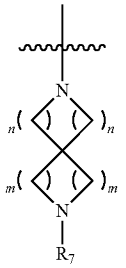
, where m and n are each independently selected from 1 and 2;

$R_7$ is selected from $C_{1-3}$ alkyl and

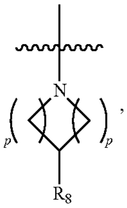
, where p is selected from 1 and 2; and $R_8$ is selected from H and cyano.

In some solutions of the present invention, the mentioned-above compound is characterized in that $R_5$ is selected from:

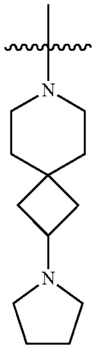
and
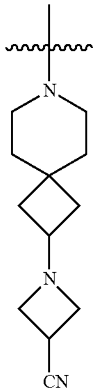
.
In some solutions of the present invention, any one of the above compounds is characterized in that the compound is selected from:
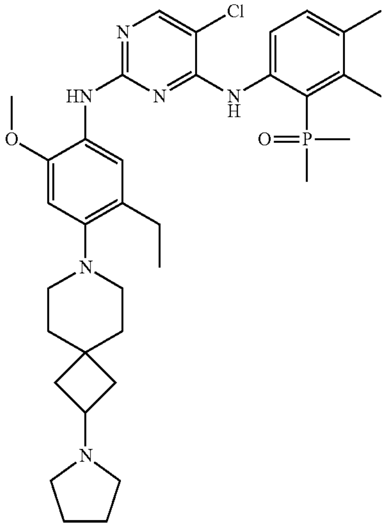
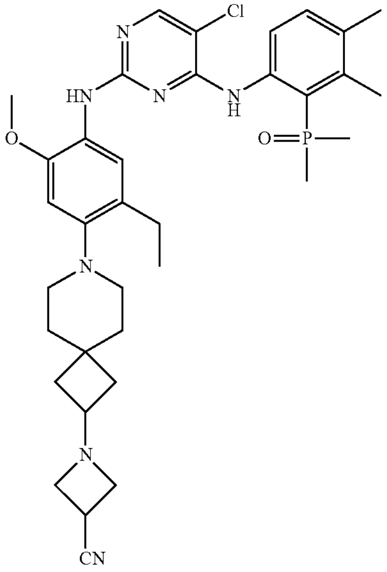
-continued
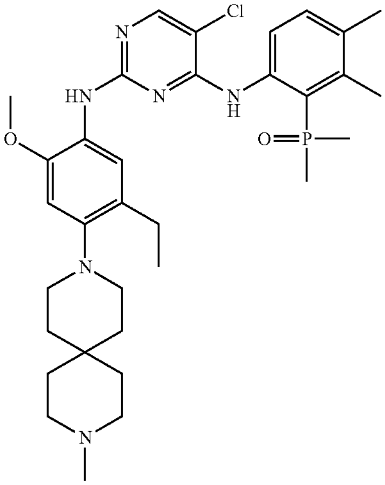
The present invention provides a compound, characterized in that the compound is selected from:
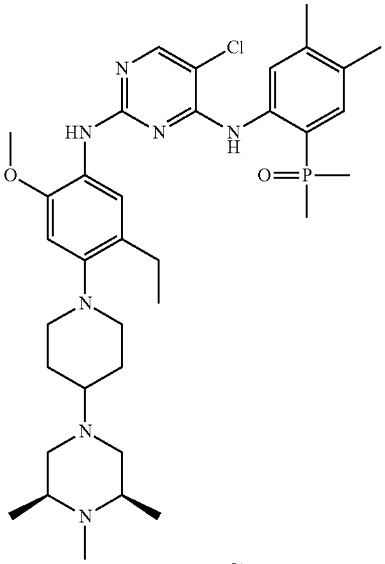
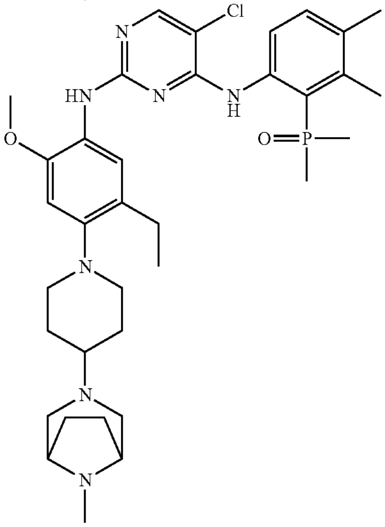

-continued

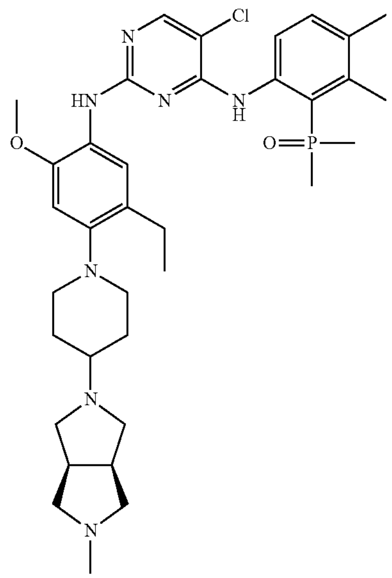

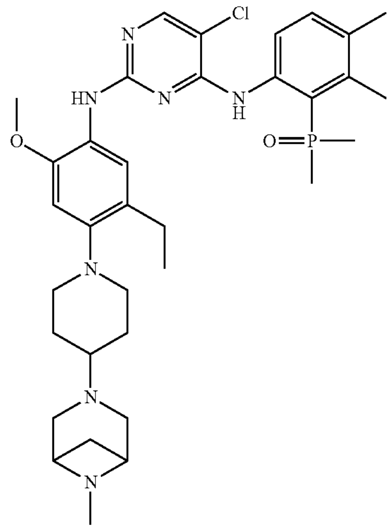

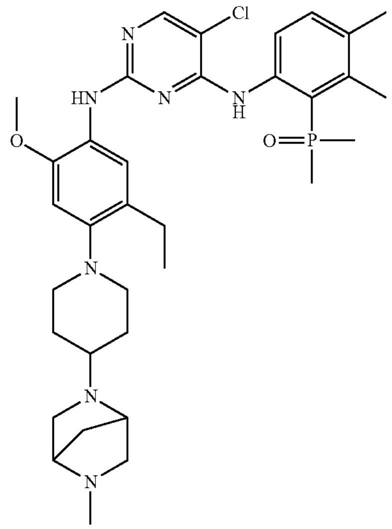

In some solutions of the present invention, provided is a pharmaceutical composition, comprising any one of the above compounds, an isomer thereof, a pharmaceutically acceptable salt thereof or a prodrug thereof.

In some solutions of the present invention, provided is use of any one of the above compounds, an isomer thereof, a pharmaceutically acceptable salt thereof or a prodrug thereof, characterized in use in preparation of an inhibitor or a drug for inhibiting a mutant EGFR.

In some solutions of the present invention, provided is use of any one of the above compounds, an isomer thereof, a pharmaceutically acceptable salt thereof, a solvate thereof or a prodrug thereof, and the drug is used for treating cancers caused by EGFR mutation, including but not limited to lung cancer, breast cancer, colorectal cancer, cerebral cancer, and head and neck cancer, wherein the lung cancer comprises small cell lung cancer and non-small cell lung cancer.

Definition and Explanation

Unless otherwise specified, the following terms and phrases used herein are intended to have the following meanings. A specific term or phrase should not be considered uncertain or unclear without a specific definition, but should be understood according to its ordinary meaning.

The term "pharmaceutically acceptable salt" refers to the inorganic or organic acid salt of the compound. The inorganic acid salt is selected from hydrochloride, hydrobromate, hydroiodate, sulfate, bisulfate, nitrate, carbonate, bicarbonate, phosphate, monohydrogen phosphate, dihydrogen phosphate, metaphosphate, and pyrophosphate; the organic acid salt is selected from formate, acetate, octanoate, isobutyrate, oxalate, trifluoroacetate, propionate, pyruvate, hydroxyacetate, oxalate, malonate, succinate, fumarate, maleate, lactate, malate, citrate, tartrate, methanesulfonate, ethanesulfonate, benzenesulfonate, salicylate, picrate, glutamate, ascorbate, camphorate, camphorsulfonate, etc.

The term "isomer" refers to the geometric isomer and stereoisomer that may be present in the compound of the present invention, such as cis-trans-isomers, enantiomers, diastereomers, as well as racemic mixtures thereof and other mixtures, all of which fall within the scope of the present invention.

The term "cis-trans-isomers" refer to a configuration in a molecule where double bonds or annulation carbon atom single bonds cannot rotate freely.

The term "enantiomers" refer to stereoisomers that are mirror images of each other.

The term "diastereomers" refer to stereoisomers in which a molecule has two or more chiral centers and molecules are not mirror images of each other.

The term "optional" or "optionally" refers to events or situations described subsequently that may but not necessarily appear, and the description includes the circumstances in which the events or situations occur and the circumstances in which the events or situations do not occur.

The term "substituted" refers to any one or more hydrogen atoms on a specific atom being replaced with substituents, which can include heavy hydrogen and hydrogen variants, as long as the valence state of the specific atom is normal and the substituted compound is stable. When the substituent is oxy (i.e., =O), it means that two hydrogen atoms are substituted. Oxy substitution does not occur on aryl. The term "optionally substituted" refers to being capable of being substituted or not substituted, unless otherwise specified, wherein the type and number of substituents can be arbitrary on the basis of chemical feasibility.

When any variable (such as R) appears more than once in the composition or structure of a compound, its definition in each case is independent. Therefore, for example, if a group is substituted by 0 to 2 Rs, the group can be optionally substituted by at most two Rs, and R in each case has an independent option. In addition, combinations of substituents and/or variants thereof are only allowed if such combinations produce stable compounds.

Unless otherwise specified, the term "alkyl" is to represent saturated hydrocarbyl in a straight or branched chain, which may be monosubstituted (such as —$CH_2F$) or polysubstituted (such as —$CF_3$), and may be monovalent (such as methyl), divalent (such as methylene), or multivalent (such as methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl), etc.

Unless otherwise specified, cycloalkyls include any stable cyclic or polycyclic hydrocarbyls, and any carbon atom is saturated, may be monosubstituted or polysubstituted, and may be monovalent, divalent, or multivalent. Examples of these cycloalkyls include, but are not limited to, cyclopropyl, norbornyl, [2.2.2]dicyclooctane, [4.4.0]dicyclodecane, etc.

Unless otherwise specified, the term "halogen" itself or as part of another substituent represents fluorine (F), chlorine (Cl), bromine (Br), or iodine (I) atoms.

Unless otherwise specified, the term "alkoxy" represents an alkyl group connected to the rest of the molecule by means of an oxygen atom, where the alkyl group has the meaning described in the present invention. Unless otherwise specified, $C_{1-5}$ alkoxys include C1, C2, C3, C4 and C5 alkoxys. Examples of alkoxys include, but are not limited to: methoxy, ethoxy, n-propoxy, isopropoxy, n-butoxy, sec-butoxy, tert-butoxy, n-pentyloxy, and S-pentyloxy. The alkoxy groups can be optionally substituted by one or more substituents described in the present invention.

Unless otherwise specified, the term "amino" refers to —NH2, —NH(alkyl), or —N(alkyl)(alkyl).

The compound of the present invention has good enzyme inhibitory activity against EGFR mutants (L858R/T790M/C797S, del19/T790M/C797S, del19/C797S, L858R/C797S), a weak inhibitory effect on wild-type EGFR, and good selectivity. The compound has significant inhibitory activity against the proliferation of EGFR mutant cells, and has potential application value in the treatment of diseases related to cell proliferation. The compound of the present invention has good solubility and permeability, good in-vivo metabolic stability, high in-vivo exposure, and high bioavailability, and is a potential pharmaceutical compound.

BRIEF DESCRIPTION OF THE DRAWINGS

FIG. 1 shows oral plasma exposure of rats of compound 6 and 12.

DESCRIPTION OF THE EMBODIMENTS

The following provides a detailed description of the present invention through embodiments, but does not imply any adverse limitations to the present invention. The present invention has been described in detail herein, and specific implementations thereof are also disclosed. For those skilled in the art, it will be apparent to make various changes and improvements to the specific implementations of the present invention without departing from the spirit and scope of the present invention.

| Compound No. | Structural formula |
| --- | --- |
| 1 | 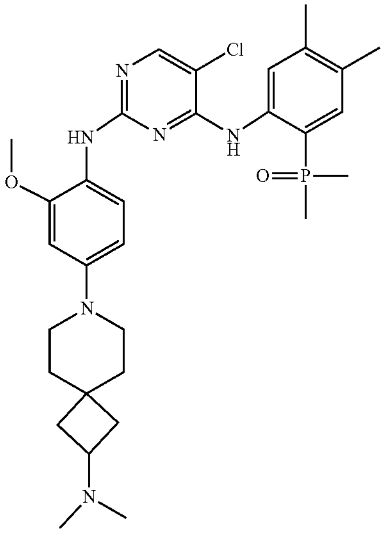 [SMILES: COc1cc(N2CCC3(CC2)CC(N(C)C)C3)ccc1Nc1ncc(Cl)c(Nc2cc(C)c(C)cc2P(C)(C)=O)n1] |
| 2 | 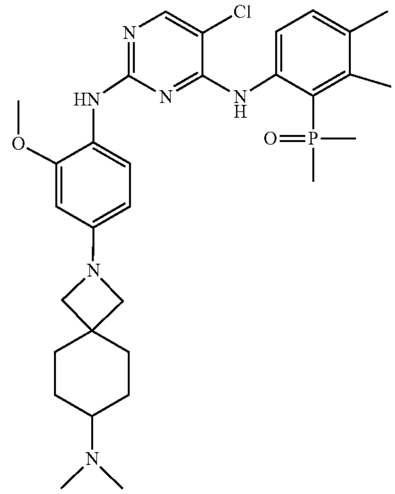 [SMILES: COc1cc(N2CC3(CCC(N(C)C)CC3)C2)ccc1Nc1ncc(Cl)c(Nc2ccc(C)c(C)c2P(C)(C)=O)n1] |
| 3 | 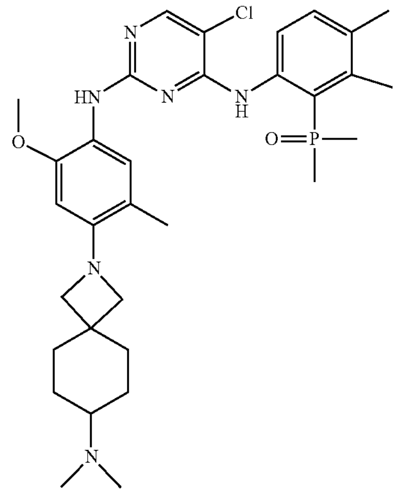 [SMILES: COc1cc(N2CC3(CCC(N(C)C)CC3)C2)c(C)cc1Nc1ncc(Cl)c(Nc2ccc(C)c(C)c2P(C)(C)=O)n1] |

-continued
| Compound No. | Structural formula |
| --- | --- |
| 4 | 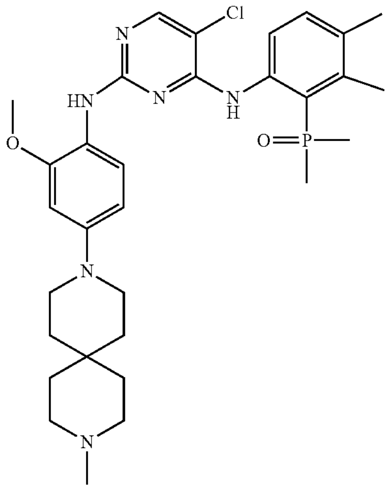 [SMILES: COc1cc(N2CCC3(CCN(C)CC3)CC2)ccc1Nc1ncc(Cl)c(Nc2ccc(C)c(C)c2P(C)(C)=O)n1] |
| 5 | 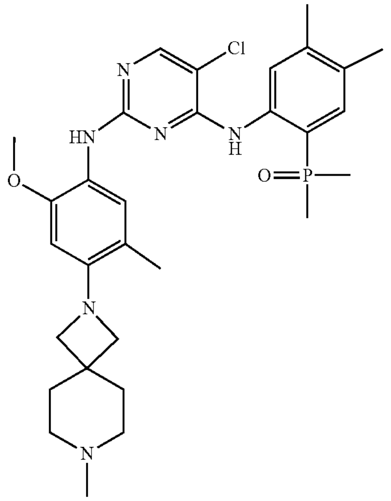 [SMILES: COc1cc(N2CC3(CCN(C)CC3)C2)c(C)cc1Nc1ncc(Cl)c(Nc2cc(C)c(C)cc2P(C)(C)=O)n1] |
| 6 | 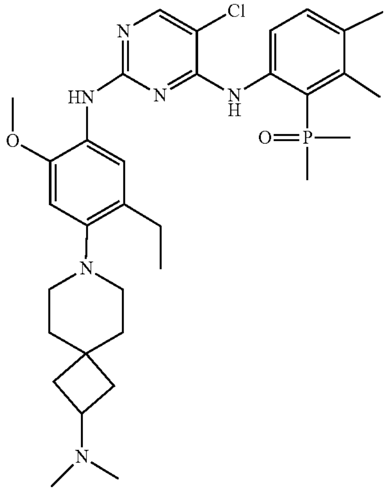 [SMILES: CCc1cc(Nc2ncc(Cl)c(Nc3ccc(C)c(C)c3P(C)(C)=O)n2)c(OC)cc1N1CCC2(CC1)CC(N(C)C)C2] |
-continued
| Compound No. | Structural formula |
| --- | --- |
| 7 | 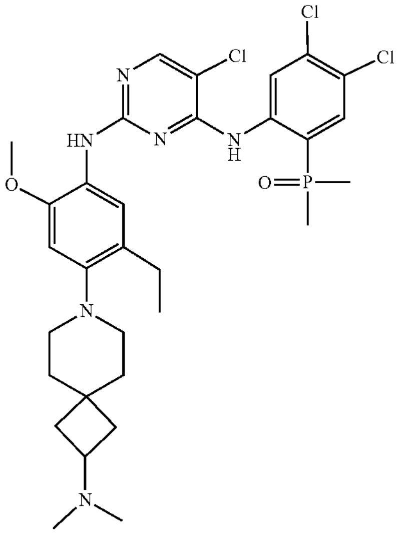 [SMILES: CCc1cc(Nc2ncc(Cl)c(Nc3cc(Cl)c(Cl)cc3P(C)(C)=O)n2)c(OC)cc1N1CCC2(CC1)CC(N(C)C)C2] |
| 8 | 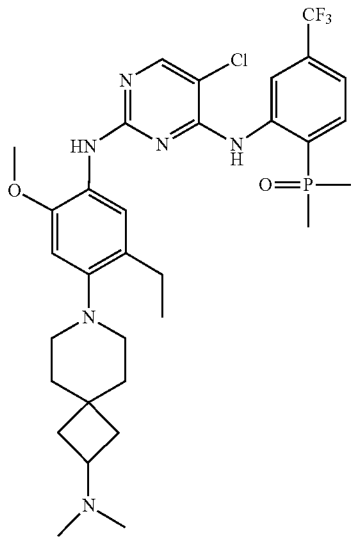 [SMILES: CCc1cc(Nc2ncc(Cl)c(Nc3cc(C(F)(F)F)ccc3P(C)(C)=O)n2)c(OC)cc1N1CCC2(CC1)CC(N(C)C)C2] |
| 9 | 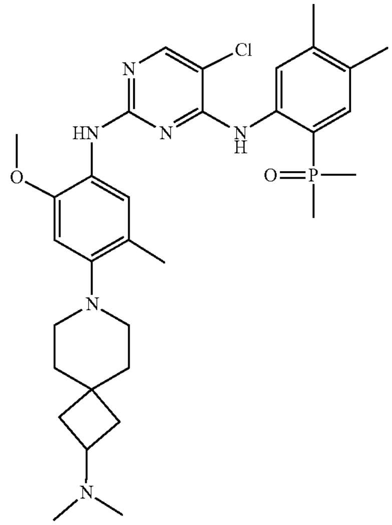 [SMILES: COc1cc(N2CCC3(CC2)CC(N(C)C)C3)c(C)cc1Nc1ncc(Cl)c(Nc2cc(C)c(C)cc2P(C)(C)=O)n1] |

-continued
| Compound No. | Structural formula |
|---|---|
| 10 | 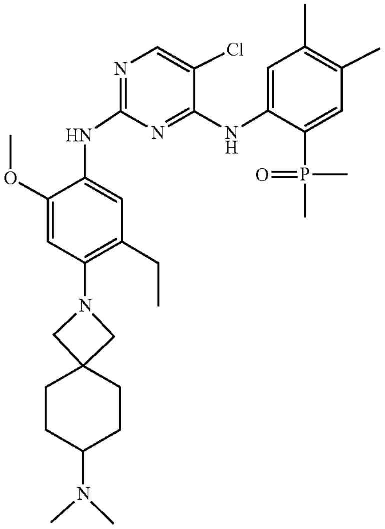 [SMILES: CCc1cc(Nc2ncc(Cl)c(Nc3cc(C)c(C)cc3P(C)(C)=O)n2)c(OC)cc1N1CC2(CCC(N(C)C)CC2)C1] |
| 11 | 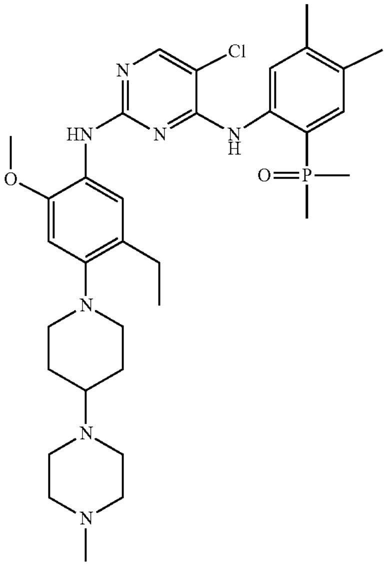 [SMILES: CCc1cc(Nc2ncc(Cl)c(Nc3cc(C)c(C)cc3P(C)(C)=O)n2)c(OC)cc1N1CCC(N2CCN(C)CC2)CC1] |
-continued
| Compound No. | Structural formula |
|---|---|
| 12 | 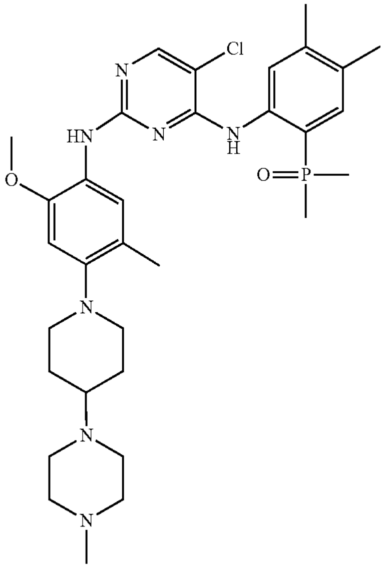 [SMILES: COc1cc(N2CCC(N3CCN(C)CC3)CC2)c(C)cc1Nc1ncc(Cl)c(Nc2cc(C)c(C)cc2P(C)(C)=O)n1] |
| 13 | 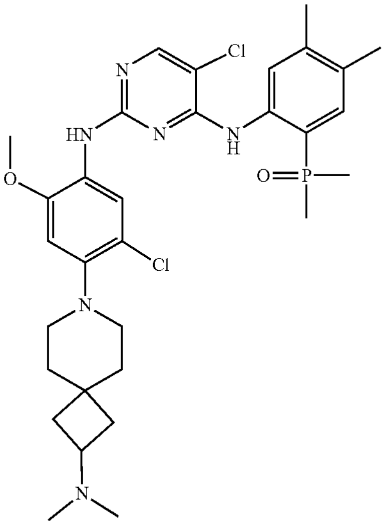 [SMILES: COc1cc(N2CCC3(CC2)CC(N(C)C)C3)c(Cl)cc1Nc1ncc(Cl)c(Nc2cc(C)c(C)cc2P(C)(C)=O)n1] |

-continued
| Compound No. | Structural formula |
|---|---|
| 14 | 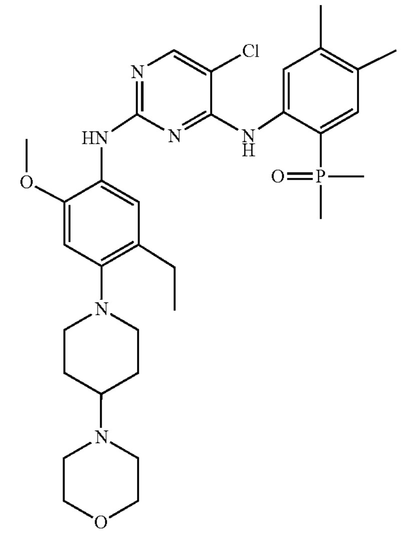 [SMILES: CCc1cc(Nc2ncc(Cl)c(Nc3cc(C)c(C)cc3P(C)(C)=O)n2)c(OC)cc1N1CCC(N2CCOCC2)CC1] |
| 15 | 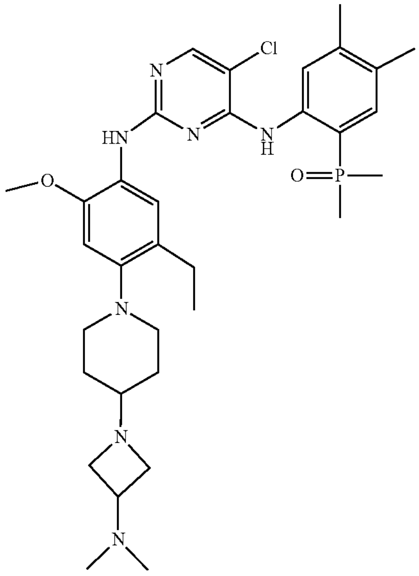 |
-continued
| Compound No. | Structural formula |
|---|---|
| 16 | 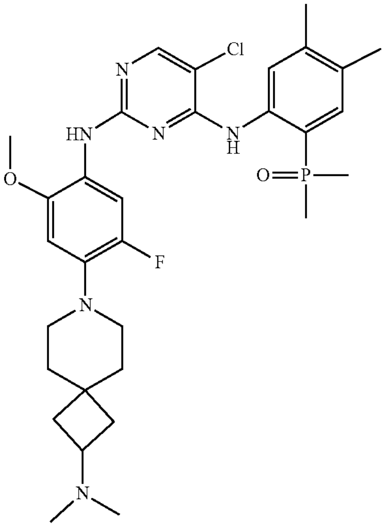 [SMILES: COc1cc(N2CCC3(CC2)CC(N(C)C)C3)c(F)cc1Nc1ncc(Cl)c(Nc2cc(C)c(C)cc2P(C)(C)=O)n1] |
| 17 | 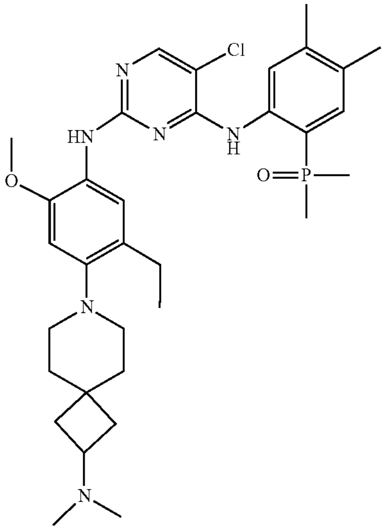 [SMILES: CCc1cc(Nc2ncc(Cl)c(Nc3cc(C)c(C)cc3P(C)(C)=O)n2)c(OC)cc1N1CCC2(CC1)CC(N(C)C)C2] |
| 18 | 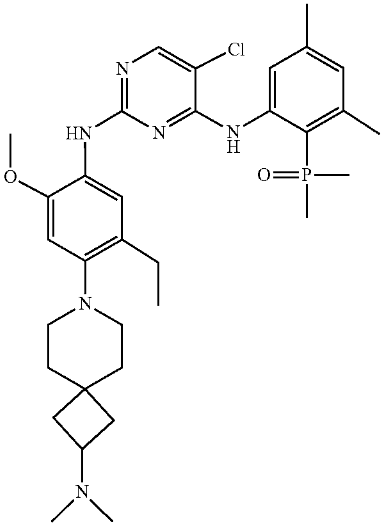 [SMILES: CCc1cc(Nc2ncc(Cl)c(Nc3cc(C)cc(C)c3P(C)(C)=O)n2)c(OC)cc1N1CCC2(CC1)CC(N(C)C)C2] |

-continued
| Compound No. | Structural formula |
| --- | --- |
| 19 | 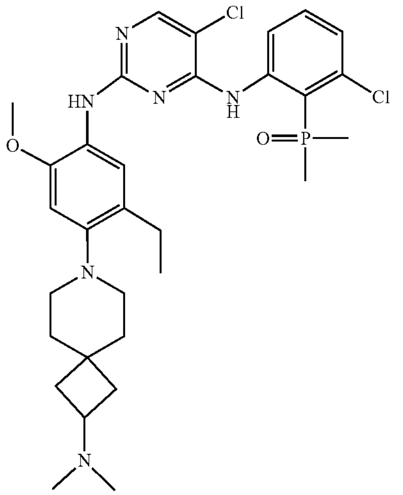 [SMILES: CCc1cc(Nc2ncc(Cl)c(Nc3cccc(Cl)c3P(C)(C)=O)n2)c(OC)cc1N1CCC2(CC1)CC(N(C)C)C2] |
| 20 | 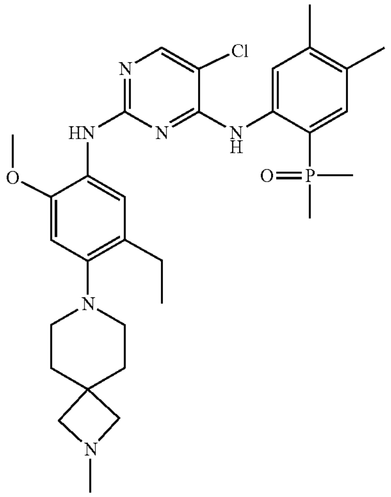 [SMILES: CCc1cc(Nc2ncc(Cl)c(Nc3cc(C)c(C)cc3P(C)(C)=O)n2)c(OC)cc1N1CCC2(CC1)CN(C)C2] |
| 21 | 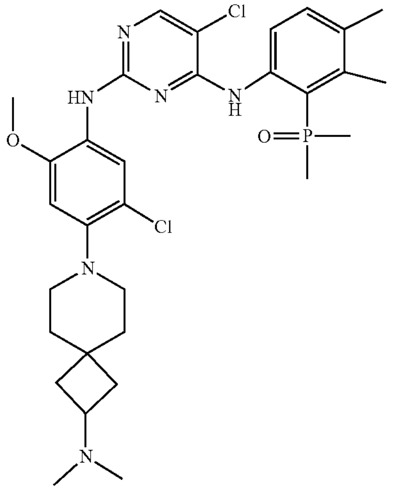 [SMILES: COc1cc(N2CCC3(CC2)CC(N(C)C)C3)c(Cl)cc1Nc1ncc(Cl)c(Nc2ccc(C)c(C)c2P(C)(C)=O)n1] |
-continued
| Compound No. | Structural formula |
| --- | --- |
| 22 | 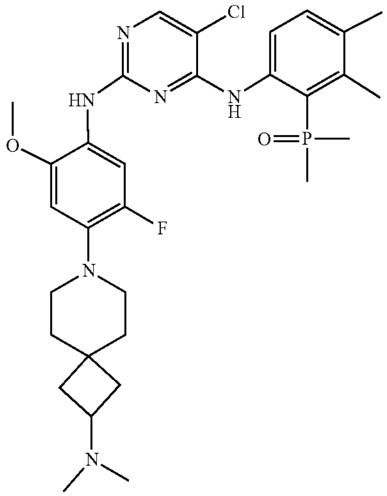 [SMILES: COc1cc(N2CCC3(CC2)CC(N(C)C)C3)c(F)cc1Nc1ncc(Cl)c(Nc2ccc(C)c(C)c2P(C)(C)=O)n1] |
| 23 | 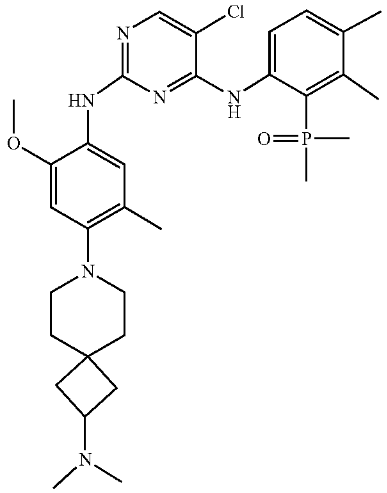 [SMILES: COc1cc(N2CCC3(CC2)CC(N(C)C)C3)c(C)cc1Nc1ncc(Cl)c(Nc2ccc(C)c(C)c2P(C)(C)=O)n1] |
| 24 | 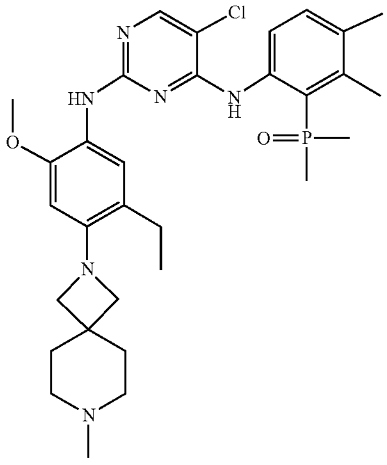 [SMILES: CCc1cc(Nc2ncc(Cl)c(Nc3ccc(C)c(C)c3P(C)(C)=O)n2)c(OC)cc1N1CC2(CCN(C)CC2)C1] |

-continued
| Compound No. | Structural formula |
| --- | --- |
| 25 | 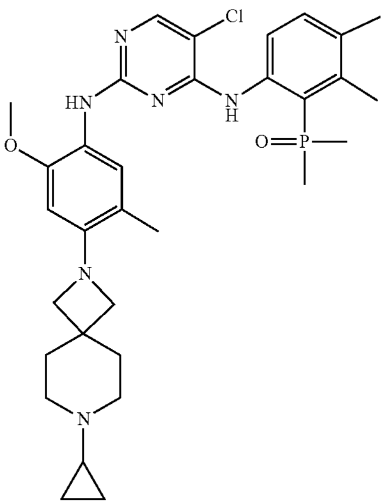 [SMILES: COc1cc(N2CC3(CCN(C4CC4)CC3)C2)c(C)cc1Nc1ncc(Cl)c(Nc2ccc(C)c(C)c2P(C)(C)=O)n1] |
| 26 | 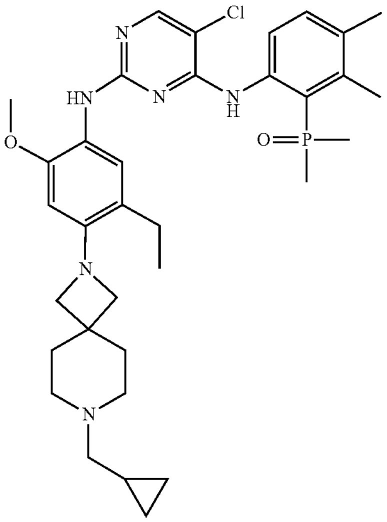 [SMILES: CCc1cc(Nc2ncc(Cl)c(Nc3ccc(C)c(C)c3P(C)(C)=O)n2)c(OC)cc1N1CC2(CCN(CC3CC3)CC2)C1] |
| 27 | 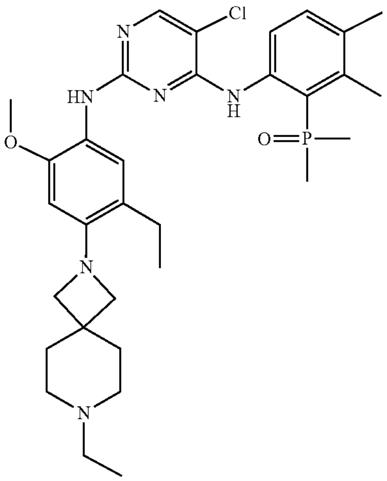 [SMILES: CCc1cc(Nc2ncc(Cl)c(Nc3ccc(C)c(C)c3P(C)(C)=O)n2)c(OC)cc1N1CC2(CCN(CC)CC2)C1] |
-continued
| Compound No. | Structural formula |
| --- | --- |
| 28 | 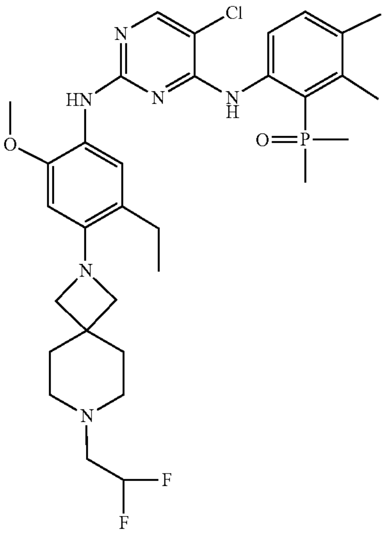 [SMILES: CCc1cc(Nc2ncc(Cl)c(Nc3ccc(C)c(C)c3P(C)(C)=O)n2)c(OC)cc1N1CC2(CCN(CC(F)F)CC2)C1] |
| 29 | 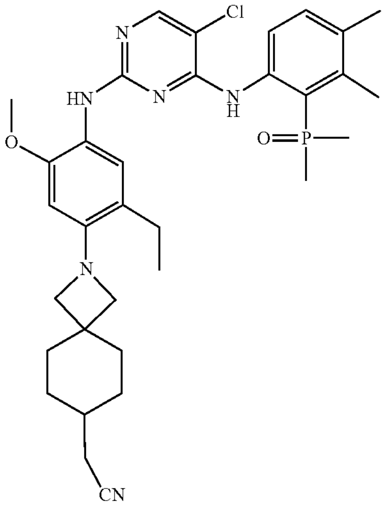 [SMILES: CCc1cc(Nc2ncc(Cl)c(Nc3ccc(C)c(C)c3P(C)(C)=O)n2)c(OC)cc1N1CC2(CCC(CC#N)CC2)C1] |
| 30 | 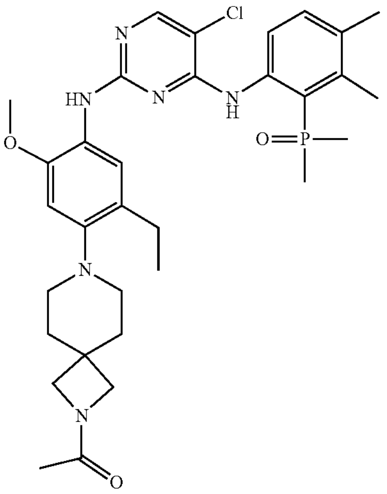 [SMILES: CCc1cc(Nc2ncc(Cl)c(Nc3ccc(C)c(C)c3P(C)(C)=O)n2)c(OC)cc1N1CCC2(CC1)CN(C(C)=O)C2] |

| Compound No. | Structural formula |
|---|---|
| 31 | 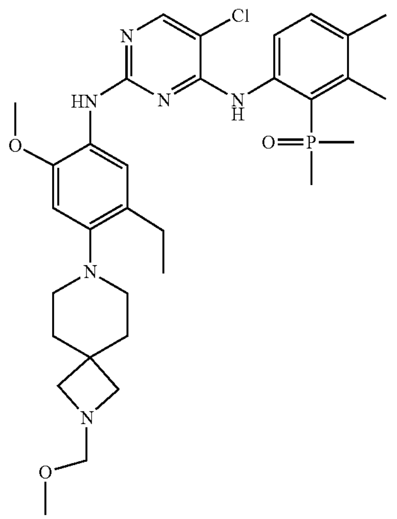 [SMILES: CCc1cc(Nc2ncc(Cl)c(Nc3ccc(C)c(C)c3P(C)(C)=O)n2)c(OC)cc1N1CCC2(CC1)CN(COC)C2] |
| 32 | 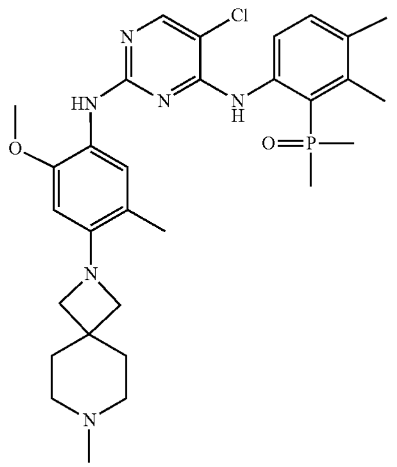 [SMILES: COc1cc(N2CC3(CCN(C)CC3)C2)c(C)cc1Nc1ncc(Cl)c(Nc2ccc(C)c(C)c2P(C)(C)=O)n1] |
| 33 | 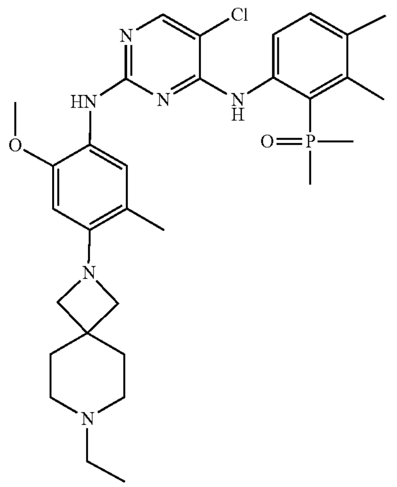 [SMILES: CCN1CCC2(CC1)CN(c1cc(OC)c(Nc3ncc(Cl)c(Nc4ccc(C)c(C)c4P(C)(C)=O)n3)cc1C)C2] |
| Compound No. | Structural formula |
|---|---|
| 34 | 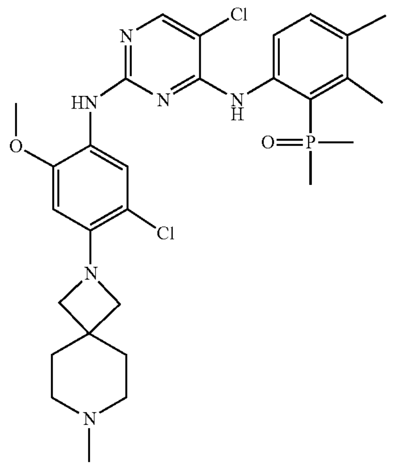 |
| 35 | 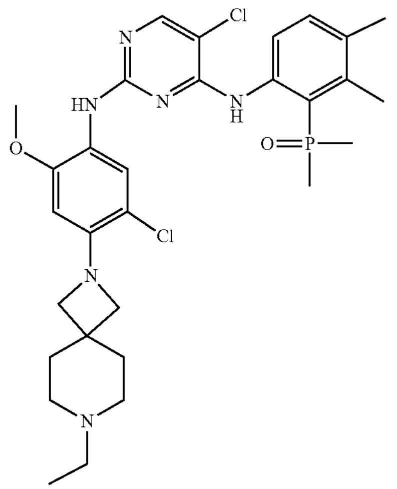 [SMILES: CCN1CCC2(CC1)CN(c1cc(OC)c(Nc3ncc(Cl)c(Nc4ccc(C)c(C)c4P(C)(C)=O)n3)cc1Cl)C2] |
| 36 | 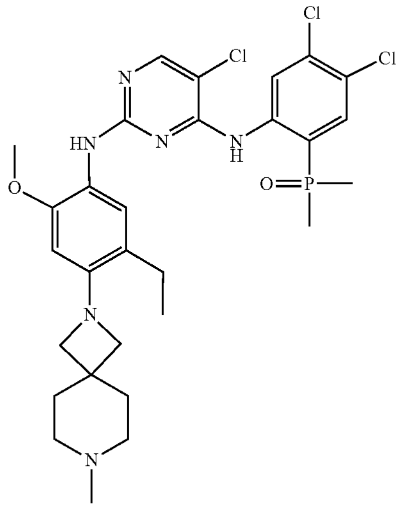 [SMILES: CCc1cc(Nc2ncc(Cl)c(Nc3cc(Cl)c(Cl)cc3P(C)(C)=O)n2)c(OC)cc1N1CC2(CCN(C)CC2)C1] |

-continued
| Compound No. | Structural formula |
|---|---|
| 37 | 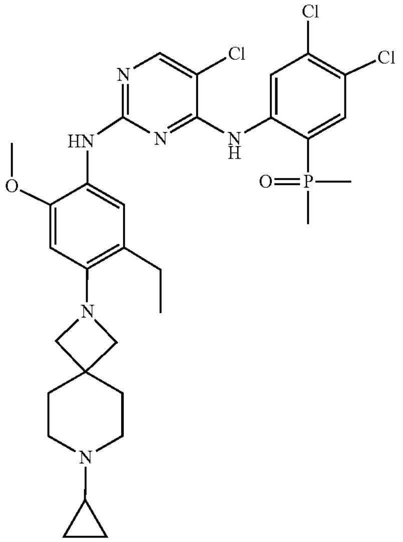 [SMILES: CCc1cc(Nc2ncc(Cl)c(Nc3cc(Cl)c(Cl)cc3P(C)(C)=O)n2)c(OC)cc1N1CC2(CCN(C3CC3)CC2)C1] |
| 38 | 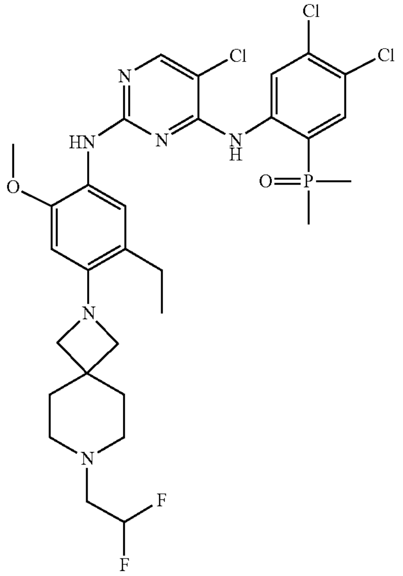 [SMILES: CCc1cc(Nc2ncc(Cl)c(Nc3cc(Cl)c(Cl)cc3P(C)(C)=O)n2)c(OC)cc1N1CC2(CCN(CC(F)F)CC2)C1] |
| 39 | 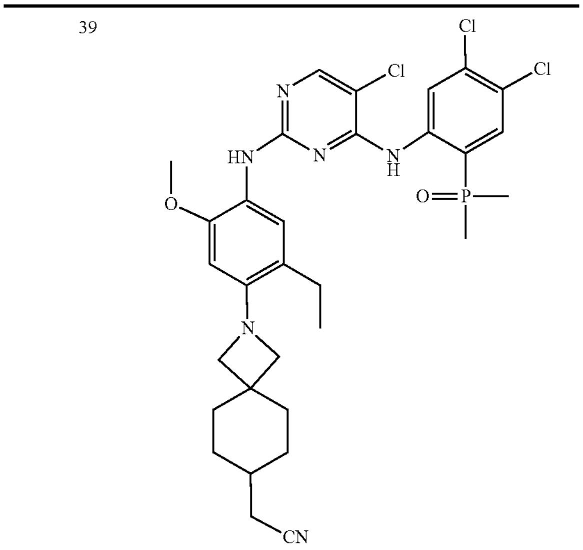 |
| 40 | 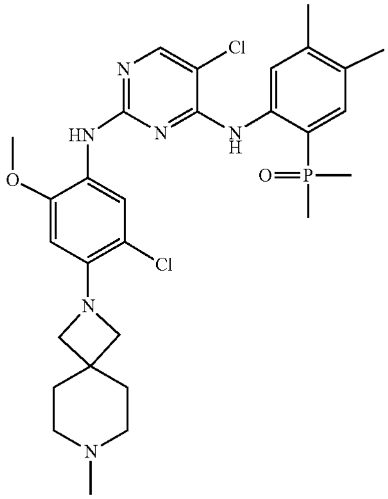 [SMILES: COc1cc(N2CC3(CCN(C)CC3)C2)c(Cl)cc1Nc1ncc(Cl)c(Nc2cc(C)c(C)cc2P(C)(C)=O)n1] |
| 41 | 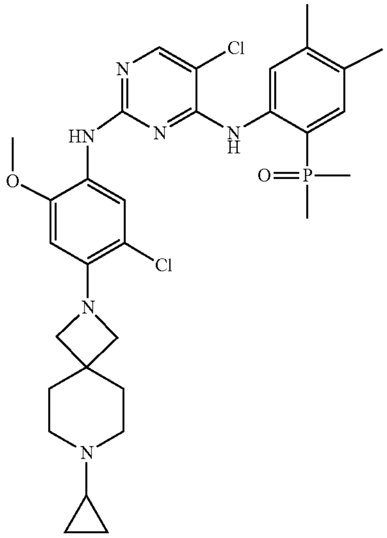 [SMILES: COc1cc(N2CC3(CCN(C4CC4)CC3)C2)c(Cl)cc1Nc1ncc(Cl)c(Nc2cc(C)c(C)cc2P(C)(C)=O)n1] |

-continued
| Compound No. | Structural formula |
| --- | --- |
| 42 | 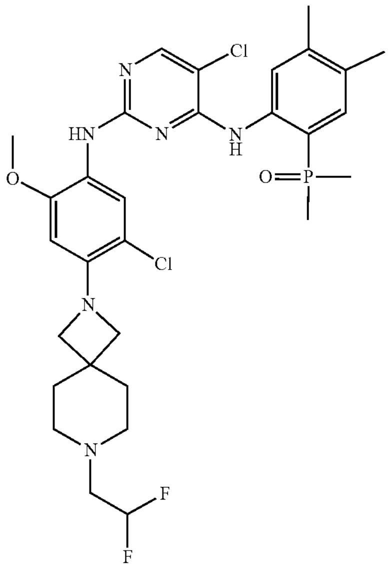 [SMILES: COc1cc(N2CC3(CCN(CC(F)F)CC3)C2)c(Cl)cc1Nc1ncc(Cl)c(Nc2cc(C)c(C)cc2P(C)(C)=O)n1] |
| 43 | 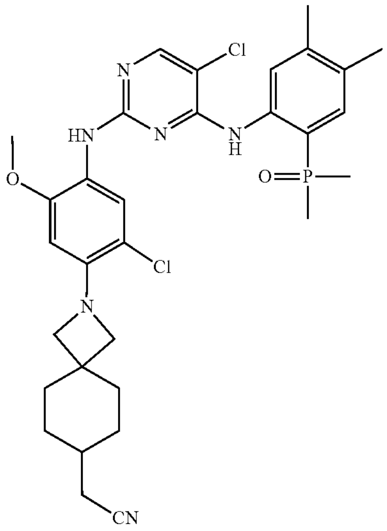 |
| 44 | 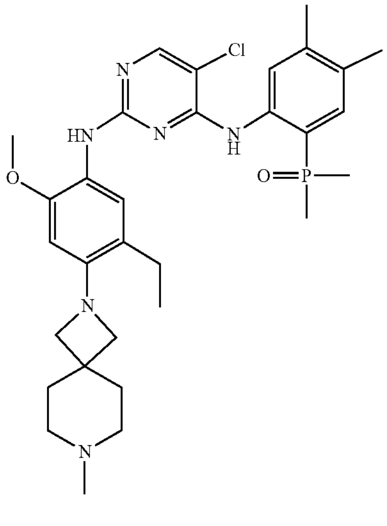 |
-continued
| Compound No. | Structural formula |
| --- | --- |
| 45 | 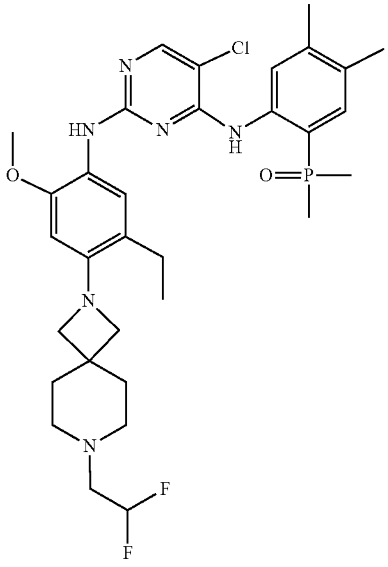 [SMILES: CCc1cc(Nc2ncc(Cl)c(Nc3cc(C)c(C)cc3P(C)(C)=O)n2)c(OC)cc1N1CC2(CCN(CC(F)F)CC2)C1] |
| 46 | 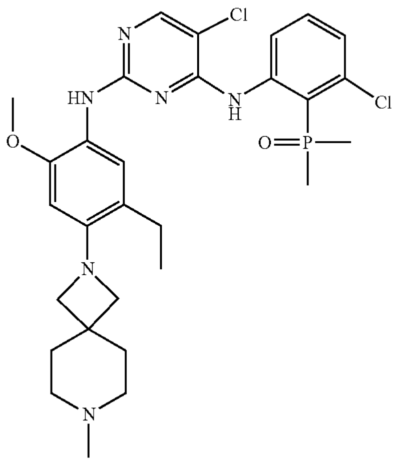 [SMILES: CCc1cc(Nc2ncc(Cl)c(Nc3cccc(Cl)c3P(C)(C)=O)n2)c(OC)cc1N1CC2(CCN(C)CC2)C1] |
| 47 | 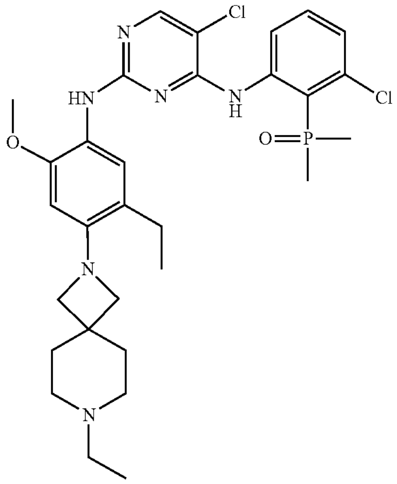 [SMILES: CCc1cc(Nc2ncc(Cl)c(Nc3cccc(Cl)c3P(C)(C)=O)n2)c(OC)cc1N1CC2(CCN(CC)CC2)C1] |

-continued
| Compound No. | Structural formula |
|---|---|
| 48 | 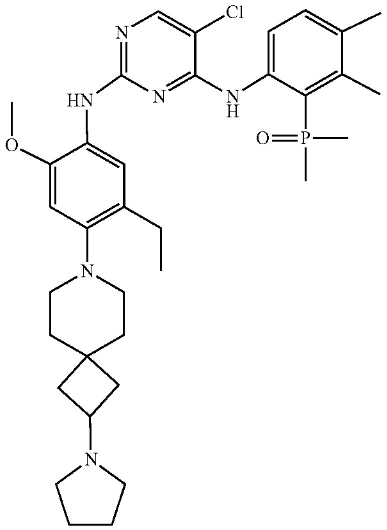 [SMILES: CCc1cc(Nc2ncc(Cl)c(Nc3ccc(C)c(C)c3P(C)(C)=O)n2)c(OC)cc1N1CCC2(CC1)CC(N1CCCC1)C2] |
| 49 | 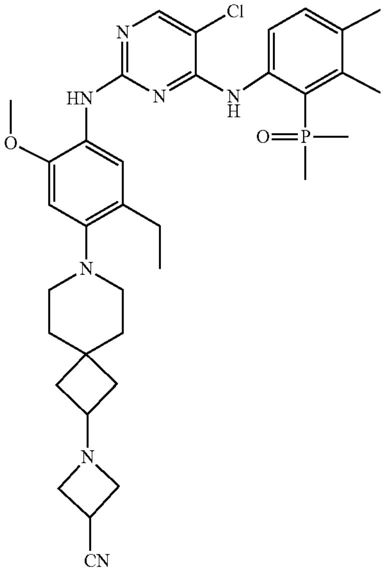 [SMILES: CCc1cc(Nc2ncc(Cl)c(Nc3ccc(C)c(C)c3P(C)(C)=O)n2)c(OC)cc1N1CCC2(CC1)CC(N1CC(C#N)C1)C2] |
-continued
| Compound No. | Structural formula |
|---|---|
| 50 | 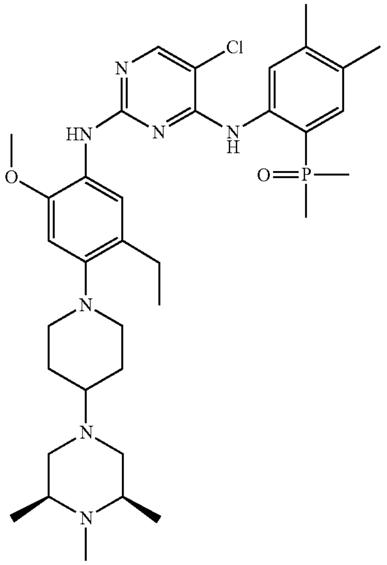 [SMILES: CCc1cc(Nc2ncc(Cl)c(Nc3cc(C)c(C)cc3P(C)(C)=O)n2)c(OC)cc1N1CCC(N2C[C@@H](C)N(C)[C@@H](C)C2)CC1] |
| 51 | 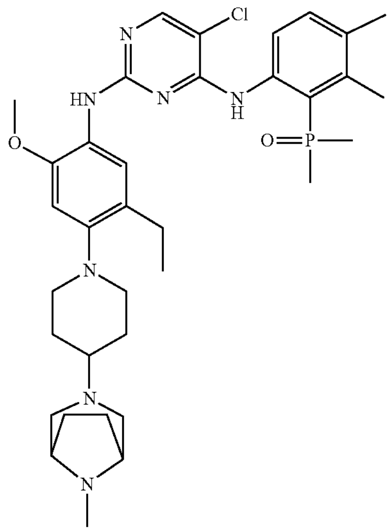 [SMILES: CCc1cc(Nc2ncc(Cl)c(Nc3ccc(C)c(C)c3P(C)(C)=O)n2)c(OC)cc1N1CCC(N2CC3CCC(C2)N3C)CC1] |

-continued
| Compound No. | Structural formula |
|---|---|
| 52 | 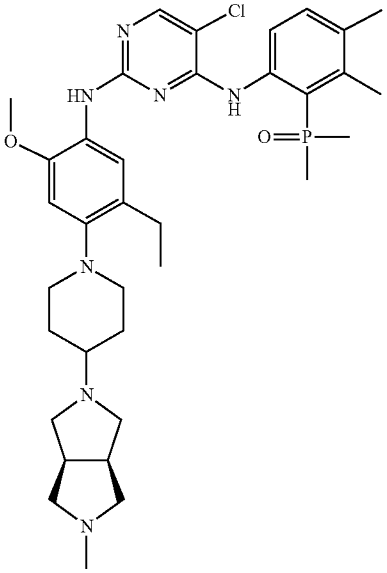 [SMILES: CCc1cc(Nc2ncc(Cl)c(Nc3ccc(C)c(C)c3P(C)(C)=O)n2)c(OC)cc1N1CCC(N2C[C@H]3CN(C)C[C@H]3C2)CC1] |
| 53 | 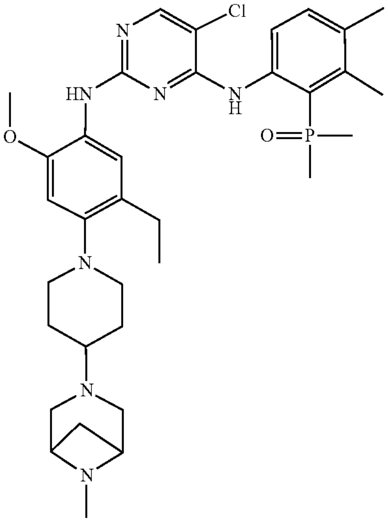 [SMILES: CCc1cc(Nc2ncc(Cl)c(Nc3ccc(C)c(C)c3P(C)(C)=O)n2)c(OC)cc1N1CCC(N2CC3CC(C2)N3C)CC1] |
-continued
| Compound No. | Structural formula |
|---|---|
| 54 | 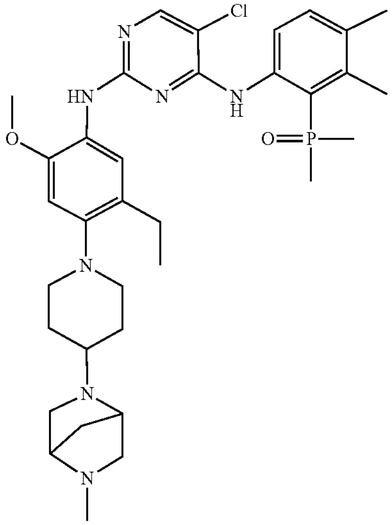 [SMILES: CCc1cc(Nc2ncc(Cl)c(Nc3ccc(C)c(C)c3P(C)(C)=O)n2)c(OC)cc1N1CCC(N2CC3CC2CN3C)CC1] |
| 55 | 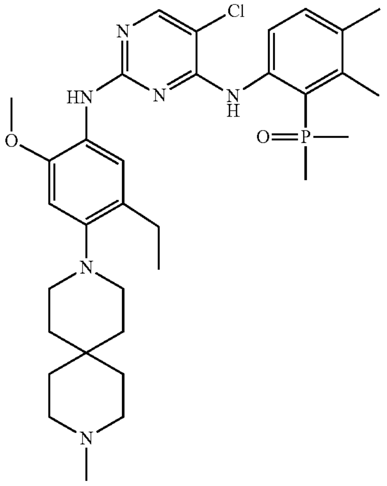 [SMILES: CCc1cc(Nc2ncc(Cl)c(Nc3ccc(C)c(C)c3P(C)(C)=O)n2)c(OC)cc1N1CCC2(CCN(C)CC2)CC1] |
Preparative Embodiment 1
(6(5-chloro-2-(4-(2-(dimethylamino)-7-azaspiro[3.5]nonan-7-yl)-5-ethyl-2-methoxyphenyl)amino)pyrimidin-4-yl)amino)-2,3-dimethylphenyl)dimethylphosphine Oxide (compound 6)
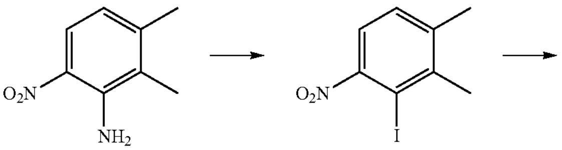
1-1 1-2

-continued

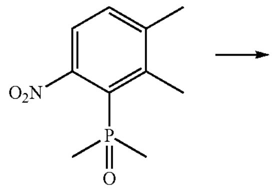
1-3

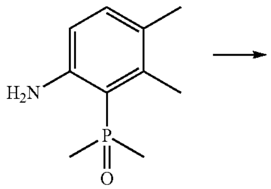
1-4

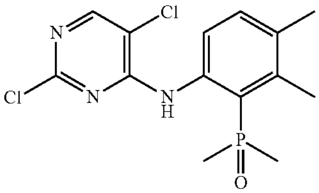
1-5

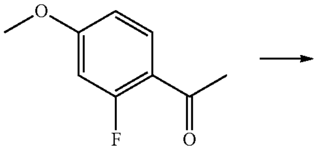
1-6

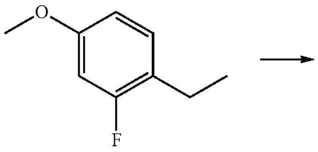
1-7

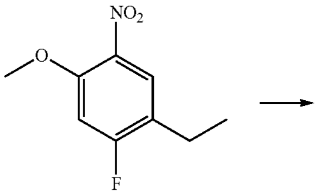
1-8

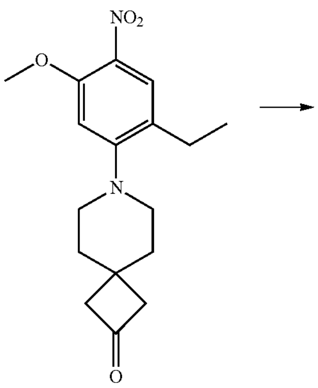
1-9

-continued

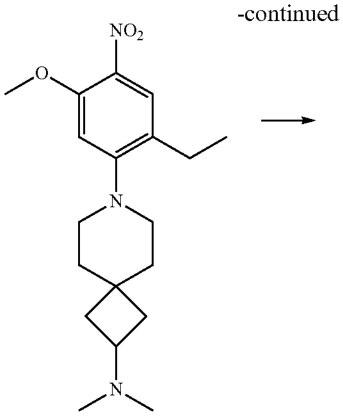
1-10

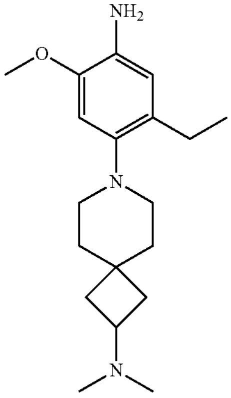
1-11

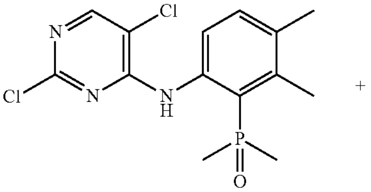
1-5

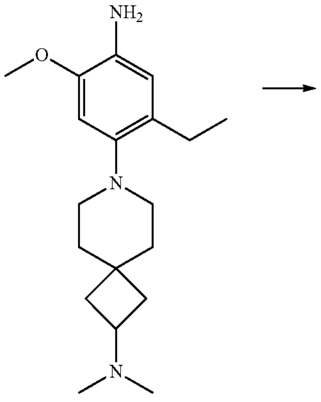
1-11

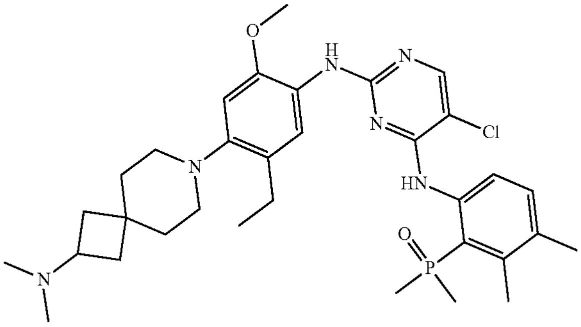
Compound 6

Step 1. 2-Iodo-3,4-dimethyl-1-nitrobenzene (1-2)

2,3-Dimethyl-6-nitroaniline (2 g, 12 mmol) was dissolved in HCl (10 mL). At 0° C., a water (5 mL) solution of $NaNO_2$ (1 g, 14.5 mmol) was slowly added. Stirring was conducted for 1 hour. A water (10 mL) solution of KI (3 g, 18 mmol) was added. Then Stirring was conducted for 1 hour at room temperature. After the reaction was completed, water (20 ml) was added to the reaction solution. Extraction was conducted with EA (ethyl acetate, 3×20 ml). The organic phase was washed with sodium thiosulfate (3×20 ml) and a saturated salt solution (3×20 ml), dried with anhydrous sodium sulfate, and purified with column chromatography (PE:EA=6:1) to obtain a product, a yellow solid (1-2).

Step 2. (2,3-Dimethyl-6-nitrophenyl)dimethylphosphine Oxide (1-3)

The intermediate 1-2 (3.0 g, 10.8 mmol) was dissolved in dioxane (20 mL). Dimethylphosphine oxide (1.27 g, 16.2 mmol), $K_3PO_4$ (4.60 g, 21.6 mmol), Pd(OAC) 2 (242 mg, 1.1 mmol), and Xantphos (4,5-bis(diphenylphosphino)-9,9-dimethylxanthene, 1.25 g, 2.2 mmol) were added in sequence. Nitrogen displacement was conducted three times. Reflux) stirring was conducted for 12 hours. After the reaction was completed, water (50 ml) was added to the reaction solution. Extraction was conducted with dichloromethane (3×50 ml). The organic phase was washed with a saturated salt solution (3×30 ml), dried with anhydrous sodium sulfate, and purified with silica gel column chromatography using DCM:MeOH (15:1) as an eluent to obtain a brown solid (1-3); ESI-MS: m/z=228 $[M+H]^+$.

Step 3. (2,3-Dimethyl-6-aminophenyl)dimethylphosphine Oxide (1-4)

The intermediate 1-3 (2.0 g) was dissolved in methanol (30 ml). 10% Palladium on carbon (55% water) (500 mg) was added. $H_2$ was introduced for displacement three times. Stirring was conducted at 40° C. for 2 hours. After the reaction was completed, suction filtration was conducted to collect the organic phase, which was subjected to rotary evaporation to remove the solvent to obtain a product (1-4); ESI-MS: m/z=198 $[M+H]^+$.

Step 4. (6-((2,5-Dichloropyrimidin-4-yl)amino)-2,3-dimethylphenyl)dimethylphosphine Oxide (1-5)

The intermediate 1-4 (1 g, 5 mmol) was dissolved in DMF (20 ml). 2,4,5-Trichloropyrimidine (1.4 g, 7.7 mmol) and $K_2CO_3$ (1.4 g, 10 mmol) were added in sequence. Heating was conducted to 100° C., and stirring was conducted for 12 hours. After the reaction was completed, water (50 ml) was added to the reaction solution. Extraction was conducted with dichloromethane (3×50 ml). Washing was conducted with a saturated salt solution, drying was conducted with anhydrous sodium sulfate, and purification was conducted with silica gel column chromatography using DCM:MeOH (15:1) as an eluent to obtain a yellow solid (1-5); ESI-MS: m/z=344 $[M+H]^+$.

Step 5. 1-Ethyl-2-fluoro-4-methoxybenzene (1-7)

Triethylsilane (2 g, 18 mmol) was dissolved in DCM. A boron trifluoride ether solution was slowly added under an ice bath until white smoke appears at the bottle mouth. 1-(2-Fluoro-4-methoxyphenyl)ethan-1-one (1-6) (1 g, 6 mmol) was dissolve in DCM (dichloromethane), and dropwise added into the above reaction solution at a constant pressure. After dropwise adding was completed, the reaction solution was transferred to a room temperature for reaction for 20 minutes. The reaction process was detected with TLC. After the reaction was completed, the reaction solution was transferred to an ice bath, a saturated salt solution was added for quenching, extraction was conducted with DCM, and the solvent was removed to obtain a white solid (1-7).

Step 6. 1-Ethyl-2-fluoro-4-methoxy-5-nitrobenzene (1-8)

The intermediate 1-7 (1 g, 6.5 mmol) was dissolved in DCM. Concentrated nitric acid (5 ml) was slowly added under an ice bath. After dropwise adding was completed, the reaction solution was transferred to a room temperature for reaction for 2 hours. The reaction process was detected with LCMS. After the reaction was completed, saturated $NaHCO_3$ was added for neutralization. Extraction was conducted with DCM, drying was conducted with anhydrous sodium sulfate, and purification was conducted with silica gel column chromatography using PE:EA=6:1 as an eluent to obtain a yellow solid (1-8). ESI-MS: m/z=200 $[M+H]^+$.

Step 7. 7-(2-Ethyl-5-methoxy-4-nitrophenyl)-7-azaspiro[3.5]nonan-2-one (1-9)

The intermediate 1-8 (400 mg, 2 mmol) was dissolved in DMSO (10 ml). 7-Azaspiro[3.5]non-2-one (350 mg, 2.5 mmol) and $K_2CO_3$ (830 mg, 6 mmol) were added in sequence. Heating was conducted to 120° C. for reaction for 12 hours. The reaction process was detected with LC-MS. After the reaction was completed, concentrated nitric acid (5 ml) was slowly added under an ice bath. After dropwise adding was completed, the reaction solution was transferred to a room temperature for reaction for 2 hours. The reaction process was detected with LC-MS. After the reaction was completed, water (30 ml) was added. Extraction was conducted with ethyl acetate (3×30 ml), washing was conducted with a saturated salt solution, drying was conducted with anhydrous sodium sulfate, and purification was conducted with silica gel column chromatography using PE:EA=1:1 as an eluent to obtain a yellow solid (1-9). ESI-MS: m/z=319 $[M+H]^+$.

Step 8. 7-(2-Ethyl-5-methoxy-4-nitrophenyl)-N,N-dimethyl-7-azaspiro[3.5]nonan-2-amine (1-10)

The intermediate 1-9 (320 mg, 1 mmol) was dissolved in DCM (10 ml). Dimethylamine (2N in THF, 2 ml) (350 mg, 2.5 mmol) and glacial acetic acid (200 μL) were added in sequence. Heating was conducted to 40° C. for reaction for 1 hour. The reaction solution was then transferred to a room temperature. Sodium triacetoxyborohydride (616 mg, 3 mmol) was added. Stirring was conducted for 1 hour. The reaction process was detected with LC-MS. After the reaction was completed, saturated $NaHCO_3$ was added for neutralization. Extraction was conducted with DCM. Washing was conducted with a saturated salt solution, drying was conducted with anhydrous sodium sulfate, and separation and purification were conducted with silica gel column chromatography using DCM:MeOH=30:1 as an eluent to obtain a light yellow solid (1-10). ESI-MS: m/z=348 $[M+H]^+$.

Step 9. 7-(2-Ethyl-5-methoxy-4-aminophenyl)-N,N-dimethyl-7-azaspiro[3.5]nonan-2-amine (1-11)

The intermediate 1-10 (350 mg, 1 mmol) was dissolved in methanol (10 ml). 10% Palladium on carbon (55% water) (35 mg) was added. $H_2$ was introduced for displacement three times. Stirring was conducted at 40° C. for 2 hours. After the reaction was completed, suction filtration was conducted to collect the organic phase, which was subjected to rotary evaporation to remove the solvent to obtain a product (1-11); ESI-MS: m/z=318 [M+H]+.

Step 10. (6-((5-chloro-2-((4-(2-(dimethylamino)-7-azaspiro[3.5]nonan-7-yl)-5-ethyl-2-methoxyphenyl) amino)pyrimidin-amino)pyrimidin-4-yl)amino)-2,3-dimethylphenyl)dimethylphosphine oxide (compound 6)

Dioxane (20 mL) was added to a mixture of the intermediate 1-5 (380 mg, 1.1 mmol), the intermediate 1-11 (320 mg, 1 mmol), palladium acetate (23 mg, 0.1 mmol), 1.1'-binaphthyl-2.2'-diphenyl phosphine (63 mg, 0.1 mmol), and cesium carbonate (1 mg, 3 mmol). Nitrogen displacement was conducted three times. Reflux stirring was conducted overnight. The solvent was recovered under reduced pressure to obtain a residue. The residue was purified with silica gel column chromatography using DCM:MeOH (25:1) as an eluent to obtain a crude product, which was purified with a silica gel preparation plate using DCM:MeOH (30:1) as a developing solvent to obtain a white solid; ESI-MS: m/z=625 [M+H]+. $^1$H NMR (400 MHz, DMSO-$d_6$) δ 11.91 (s, 1H), 8.04 (s, 1H), 7.96 (dd, J=8.8, 4.0 Hz, 1H), 7.84 (s, 1H), 7.49 (s, 1H), 7.16 (d, J=8.5 Hz, 1H), 6.74 (s, 1H), 3.76 (s, 3H), 2.74 (t, J=5.0 Hz, 2H), 2.68 (dd, J=7.0, 3.4 Hz, 2H), 2.46 (t, J=7.4 Hz, 5H), 2.39 (s, 6H), 2.29 (s, 3H), 2.20 (s, 3H), 2.11 (s, 2H), 1.89 (s, 6H), 1.68 (q, J=5.1 Hz, 4H), 0.99 (t, J=7.4 Hz, 3H).

Preparative Embodiment 2. (6-((5-Chloro-2-((4-(2-(dimethylamino)-7-azaspiro[3.5]nonan-7-yl)-2-methoxyphenyl)amino)pyrimidin-4-yl)amino)-3,4-dimethylphenyl)dimethylphosphine Oxide (compound 1)

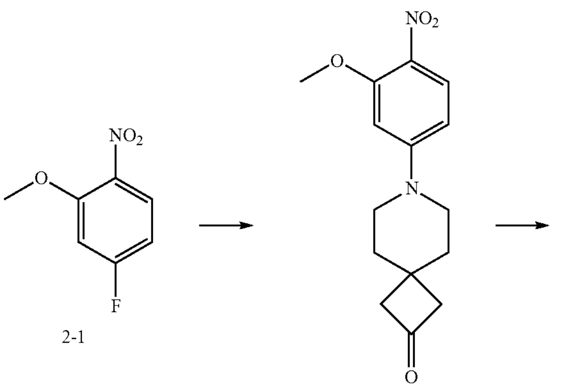

2-1

2-2

-continued

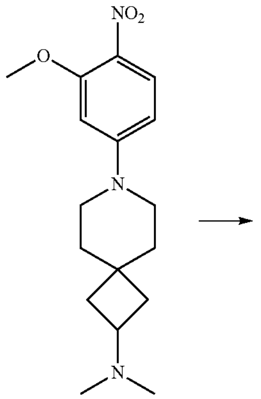

2-3

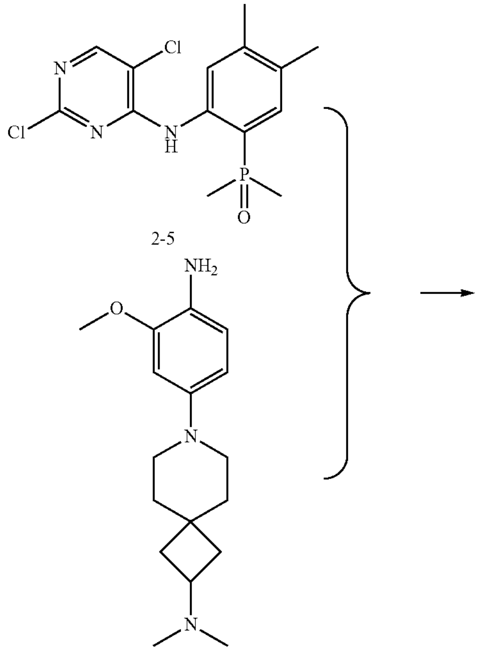

2-5

2-4

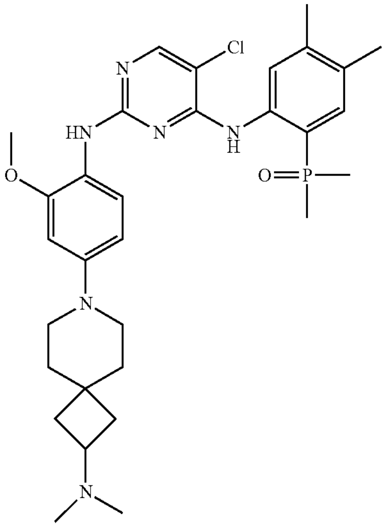

Compound 1

Step 1. 7-(3-Methoxy-4-nitrophenyl)-7-azaspiro[3.5]nonan-2-one (2-2)

The synthesis steps refer to step 7 of Preparative Embodiment 1. Compound 2-2 was prepared by replacing the intermediate 1-8 with 4-fluoro-2-methoxy-1-nitrobenzene; ESI-MS: m/z=291 $[M+1]^+$.

Step 2. 7-(3-Methoxy-4-nitrophenyl)-N,N-dimethyl-7-azaspiro[3.5]nonan-2-amine (2-3)

The synthesis steps refer to step 8 of Preparative Embodiment 1. Compound 2-3 was prepared by replacing compound 1-9 with compound 2-2; ESI-MS: m/z=320 $[M+1]^+$.

Step 3. 7-(3-Methoxy-4-aminophenyl)-N,N-dimethyl-7-azaspiro[3.5]nonan-2-amine (2-4)

The synthesis steps refer to step 9 of Preparative Embodiment 1. Compound (2-4) was prepared by replacing compound 1-10 with compound 2-3; ESI-MS: m/z=290 $[M+1]^+$.

Step 4. (2-((2,5-Dichloropyrimidin-4-yl)amino)-4,5-dimethylphenyl)dimethylphosphine oxide (2-5)

The synthesis steps refer to steps 1-4 of Preparative Embodiment 1. Compound 2-5 was prepared by replacing 2,3-dimethyl-6-nitroaniline with 4,5-dimethyl-2-nitroaniline; ESI-MS: m/z=344 $[M+1]^+$.

Step 5. (6-((5-Chloro-2-((4-(2-(dimethylamino)-7-azaspiro[3.5]nonan-7-yl)-2-methoxyphenyl)amino)pyrimidin-4-yl)amino)-3,4-dimethylphenyl)dimethylphosphine oxide (compound 1)

The synthesis steps refer to step 10 of Preparative Embodiment 1. Compound 1 was prepared by replacing compound 1-11 with compound 2-4 and replacing compound 1-5 with compound 2-5; ESI-MS: m/z=597 $[M+1]^+$. $^1H$ NMR (400 MHz, Chloroform-d) δ 10.65 (s, 1H), 8.34 (d, J=4.5 Hz, 1H), 8.10 (d, J=8.7 Hz, 1H), 8.02 (s, 1H), 7.42 (s, 1H), 7.00 (d, J=14.1 Hz, 1H), 6.57 (s, 1H), 6.44 (dd, J=8.9, 2.5 Hz, 1H), 3.85 (s, 3H), 3.40 (p, J=8.2 Hz, 1H), 3.08-2.96 (m, 4H), 2.69 (s, 6H), 2.63-2.53 (m, 2H), 2.27 (d, J=7.6 Hz, 8H), 2.00-1.96 (m, 2H), 1.80 (d, J=13.1 Hz, 8H).

Preparative Embodiment 3. 2-((5-Chloro-2-((2-methoxy-5-methyl-4-(7-methyl-2,7-diazaspiro[3.5]nonan-2-yl)phenyl)amino)pyrimidin-4-yl)amino)-4,5-dimethylphenyl)dimethylphosphine Oxide (compound 5)

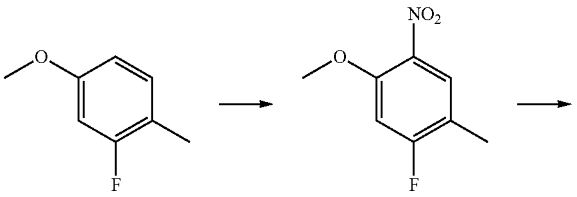

3-1 3-2

-continued

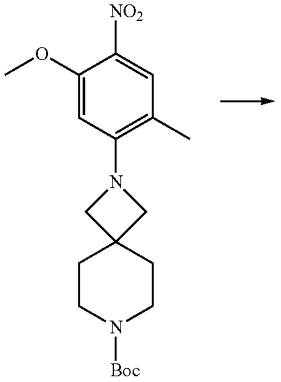

3-3

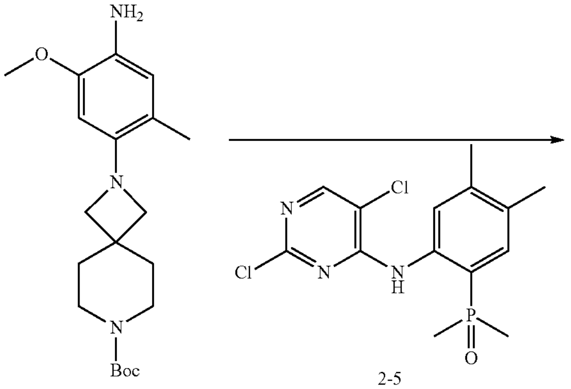

3-4 2-5

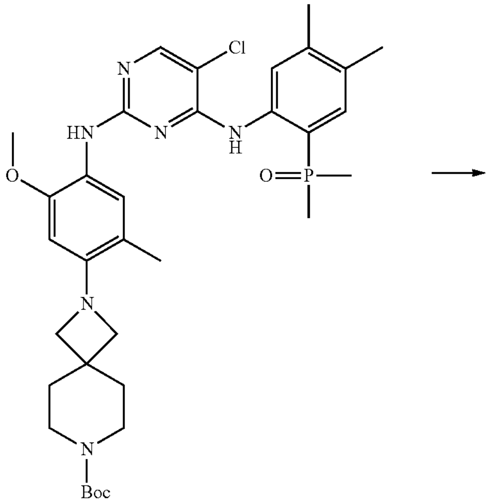

3-5

-continued

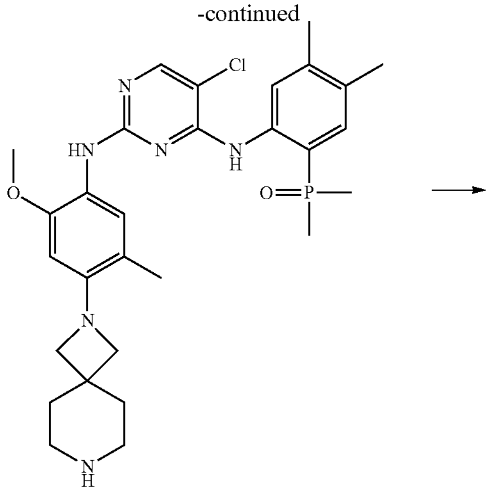

3-6

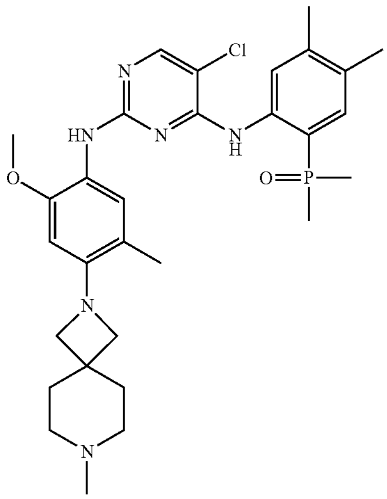

Compound 5

Step 1. 1-Fluoro-5-methoxy-2-methyl-4-nitrobenzene (3-2)

The synthesis steps refer to step 6 of Preparative Embodiment 1. Compound 3-2 was prepared by replacing compound 1-7 with 2-fluoro-4-methoxy-1-toluene; ESI-MS: m/z=186 [M+1]$^+$.

Step 2. Tert-butyl 2-(5-methoxy-2-methyl-4-nitrophenyl)-2,7-diazaspiro[3.5]nonane-7-carboxylate (3-3)

The synthesis steps refer to step 7 of Preparative Embodiment 1. Compound 3-3 was prepared by replacing 7-azaspiro[3.5]nonane-2-one with tert-butyl 2,7-diazaspiro[3.5]nonane-7-carboxylate; ESI-MS: m/z=392 [M+1]$^+$.

Step 3. Tert-Butyl 2-(5-methoxy-2-methyl-4-aminophenyl)-2,7-diazaspiro[3.5]nonane-7-carboxylate (3-4)

The synthesis steps refer to step 9 of Preparative Embodiment 1. Compound 3-4 was prepared by replacing compound 1-10 with compound 3-3. ESI-MS: m/z=362[M+1]$^+$.

Step 4. Tert-Butyl 2-(4-((5-chloro-4-((2-(dimethylphosphoryl)-4,5-dimethylphenyl)amino)pyrimidin-2-yl)amino)-5-methoxy-2-methylphenyl)-2,7-diazaspiro[3.5]nonane-7-carboxylate (3-5)

The synthesis steps refer to step 10 of Preparative Embodiment 1. Compound 3-5 was prepared by replacing compound 1-11 with compound 3-4 and replacing compound 1-5 with compound 2-5; ESI-MS: m/z=669 [M+1]$^+$.

Step 5. (2-((5-Chloro-2-((2-methoxy-5-methyl-4-(2,7-diazaspiro[3.5]non-2-yl)phenyl)amino)pyrimidin-4-yl)amino)-4,5-dimethylphenyl)dimethylphosphine oxide (3-6)

The intermediate 3-5 (200 mg) was dissolved in dichloromethane (4 ml). Trifluoroacetic acid (2 ml) was dropwise added under an ice bath. Stirring was conducted for 1 hour. The reaction was detected with LC-MS. After the reaction was completed, the solvent was removed to obtain a white solid; ESI-MS: m/z=569 [M+1]$^+$.

Step 6. (2-((5-Chloro-2-((2-methoxy-5-methyl-4-(7-methyl-2,7-diazaspiro[3.5]nonan-2-yl)phenyl)amino)pyrimidin-4-yl)amino)-4,5-dimethylphenyl)dimethylphosphine oxide (compound 5)

The synthesis steps refer to step 8 of Preparative Embodiment 1. Compound 5 was prepared by replacing compound 1-9 with compound 3-6 and replacing dimethylamine with paraformaldehyde; ESI-MS: m/z=583 [M+1]$^+$. $^1$H NMR (400 MHz, Chloroform-d) δ 10.48 (s, 1H), 8.32 (d, J=4.5 Hz, 1H), 8.04 (s, 1H), 7.84 (s, 1H), 7.13 (s, 1H), 7.00 (d, J=14.1 Hz, 1H), 6.07 (s, 1H), 3.84 (s, 3H), 3.67 (d, J=3.5 Hz, 4H), 2.90 (s, 4H), 2.63 (s, 3H), 2.23 (d, J=16.5 Hz, 10H), 2.02 (s, 3H), 1.80 (d, J=13.1 Hz, 6H).

Preparative Embodiment 4. (4,5-Dichloro-2-((5-chloro-2-((4-(2-(dimethylamino)-7-azaspiro[3.5]nonan-7-yl)-5-ethyl-2-methoxyphenyl)amino)pyrimidin-4-yl)amino)phenyl)dimethylphosphine Oxide (compound 7)

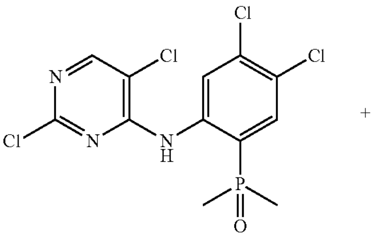

4-1

-continued

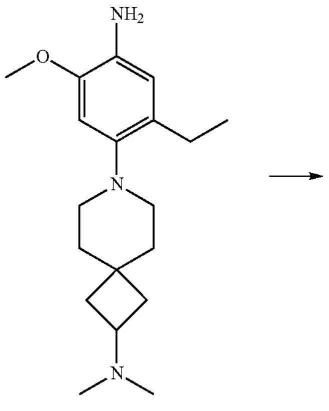

1-11

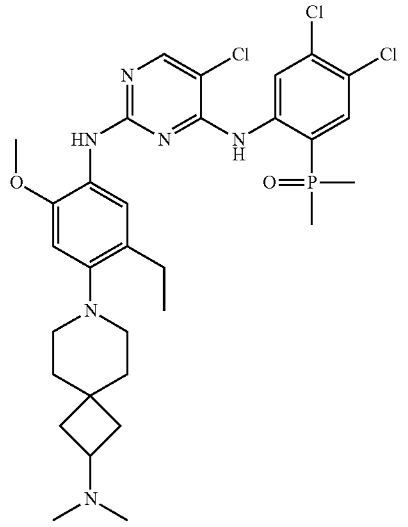

Compound 7

Step 1. (4,5-Dichloro-2-((2,5-dichloropyrimidin-4-yl)amino)phenyl)dimethylphosphine Oxide (4-1)

The synthesis steps refer to steps 1 to 4 of Preparative Embodiment 1. Compound 4-1 was prepared by replacing 2,3-dimethyl-6-nitroaniline with 4,5-dichloro-2-nitroaniline; ESI-MS: m/z=384 $[M+1]^+$.

Step 2. (4,5-Dichloro-2-((5-chloro-2-((4-(2-(dimethylamino)-7-azaspiro[3.5]nonan-7-yl)-5-ethyl-2-methoxyphenyl)amino)pyrimidin-4-yl)amino)phenyl)dimethylphosphine Oxide (compound 7)

The synthesis steps refer to step 10 of Preparative Embodiment 1. Compound 7 was prepared by replacing compound 1-5 with compound 4-1; ESI-MS: m/z=665 $[M+1]^+$. $^1H$ NMR (400 MHz, Chloroform-d) δ 10.82 (s, 1H), 8.83 (d, J=4.2 Hz, 1H), 8.12 (s, 1H), 7.91 (s, 1H), 7.29 (s, 1H), 7.24 (s, 1H), 6.63 (s, 1H), 3.85 (s, 3H), 3.03 (t, J=8.1 Hz, 1H), 2.75 (dt, J=18.2, 5.3 Hz, 4H), 2.58 (q, J=7.5 Hz, 2H), 2.43 (s, 6H), 2.22-2.09 (m, 4H), 1.84 (d, J=13.2 Hz, 6H), 1.83-1.71 (m, 4H), 1.04 (t, J=7.5 Hz, 3H).

Preparative Embodiment 5. (2-((5-Chloro-2-((4-(2-(dimethylamino)-7-azaspiro[3.5]nonan-7-yl)-5-ethyl-2-methoxyphenyl)amino)pyrimidin-4-yl)amino)-4-(trifluoromethyl)phenyl)dimethylphosphine Oxide (Compound 8)

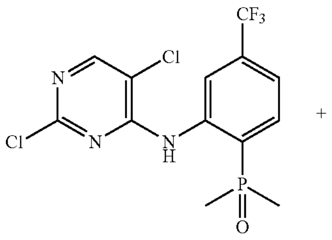

5-1

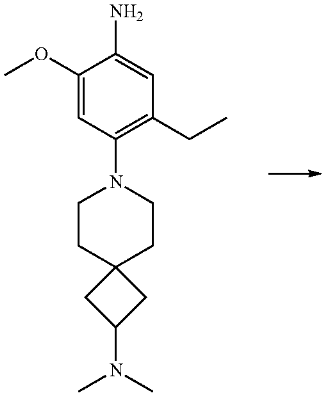

1-11

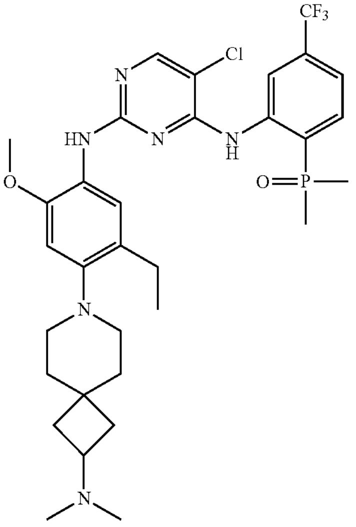

Compound 8

Step 1. (5-Chloro-2-((2,5-dichloropyrimidin-4-yl)amino)phenyl)dimethylphosphine Oxide (5-1)

The synthesis steps refer to steps 1 to 4 of Preparative Embodiment 1. Compound 5-1 was prepared by replacing 2,3-dimethyl-6-nitroaniline with 4-trifluoromethyl-2-nitroaniline; ESI-MS: m/z=384 $[M+1]^+$.

Step 2. (2-((5-Chloro-2-((4-(2-(dimethylamino)-7-azaspiro[3.5]nonan-7-yl)-5-ethyl-2-methoxyphenyl)amino)pyrimidin-4-yl)amino)-4-(trifluoromethyl)phenyl)dimethylphosphine Oxide (Compound 8)

The synthesis steps refer to step 10 of Preparative Embodiment 1. Compound 8 was prepared by replacing compound 1-5 with compound 5-1; ESI-MS: m/z=665 $[M+1]^+$. $^1H$ NMR (400 MHz, Chloroform-d) δ 10.96 (s, 1H), 9.00 (s, 1H), 8.15 (s, 1H), 8.01 (s, 1H), 7.42-7.26 (m, 3H), 6.61 (s, 1H), 3.85 (s, 3H), 3.23 (t, J=8.3 Hz, 1H), 2.74 (dt, J=14.6, 5.5 Hz, 4H), 2.56 (d, J=13.5 Hz, 8H), 2.42-2.17 (m, 4H), 1.87 (d, J=13.2 Hz, 6H), 1.85-1.70 (m, 4H), 1.06 (t, J=7.5 Hz, 3H).

Preparative Embodiment 6. (6-((5-Chloro-2-((2-methoxy-5-methyl-4-(4-(4-methylpiperazin-1-yl)piperidin-1-yl)phenyl)amino)pyrimidin-4-yl)amino)-2,3-dimethylphenyl)dimethylphosphine Oxide (Compound BD-2)

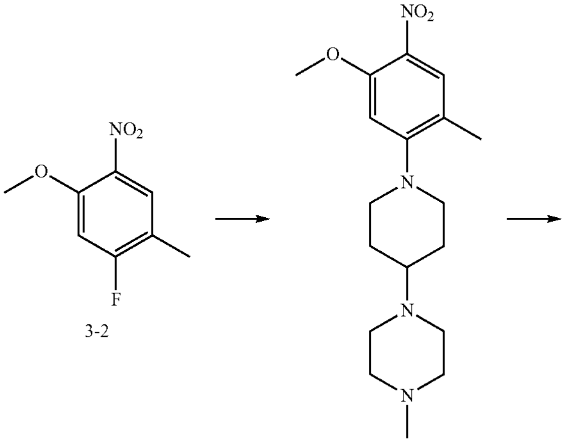

3-2

6-1

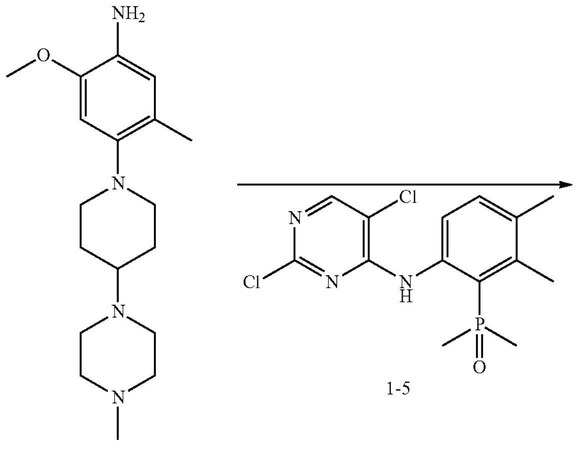

6-2

1-5

-continued

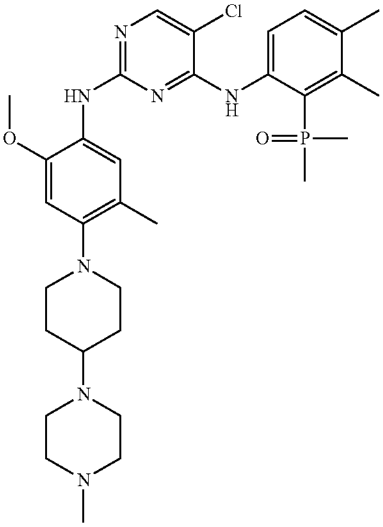

BD-2

Step 1. 1-(1-(5-methoxy-2-methyl-4-nitrophenyl)piperidin-4-yl)-4-methylpiperazine (6-1)

The synthesis steps refer to step 7 of Preparative Embodiment 1. Compound 6-1 was prepared by replacing compound 1-8 with compound 3-2 and replacing 7-azaspiro[3.5]nonane-2-one with 1-methyl-4-(piperidin-4-yl) piperazine. ESI-MS: m/z=349 $[M+1]^+$.

Step 2. 1-(1-(5-Methoxy-2-methyl-4-aminophenyl)piperidin-4-yl)-4-methylpiperazine (6-2)

The synthesis steps refer to step 9 of Preparative Embodiment 1. Compound 6-2 was prepared by replacing compound 1-10 with compound 6-1. ESI-MS: m/z=319 $[M+1]^+$.

Step 3. (6-((5-Chloro-2-((2-methoxy-5-methyl-4-(4-(4-methylpiperazin-1-yl) piperidin-1-yl)phenyl)amino)pyrimidin-4-yl)amino)-2,3-dimethylphenyl)dimethylphosphine Oxide (compound BD-2)

The synthesis steps refer to step 10 of Preparative Embodiment 1. Compound BD-2 was prepared by replacing compound 1-11 with compound 6-2. ESI-MS: m/z=626 $[M+1]^+$. $^1H$ NMR (400 MHz, DMSO-$d_6$) δ 10.65 (s, 1H), 8.06 (s, 1H), 7.97 (dd, J=8.8, 4.0 Hz, 1H), 7.85 (s, 1H), 7.47 (s, 1H), 7.15 (d, J=8.5 Hz, 1H), 6.73 (s, 1H), 3.75 (s, 3H), 3.08 (d, J=11.5 Hz, 2H), 2.73-2.51 (m, 6H), 2.43-2.21 (m, 5H), 2.17 (s, 3H), 2.16 (s, 3H), 2.05 (s, 3H), 2.01 (s, 3H), 1.86 (d, J=12.6 Hz, 2H), 1.73 (d, J=13.5 Hz, 6H), 1.60-1.48 (m, 2H).

Preparative Embodiment 7. (2-((5-Chloro-2-((2-methoxy-5-methyl-4-(4-(4-methylpiperazin-1-yl) piperidin-1-yl)phenyl)amino)pyrimidin-4-yl)amino)-4,5-dimethylphenyl)dimethylphosphine Oxide (Compound 12)

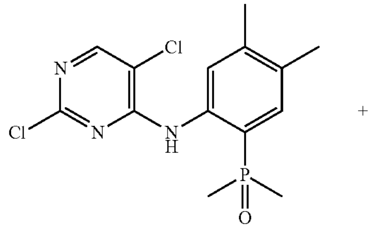

2-5

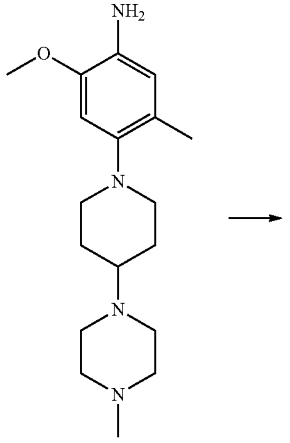

6-2

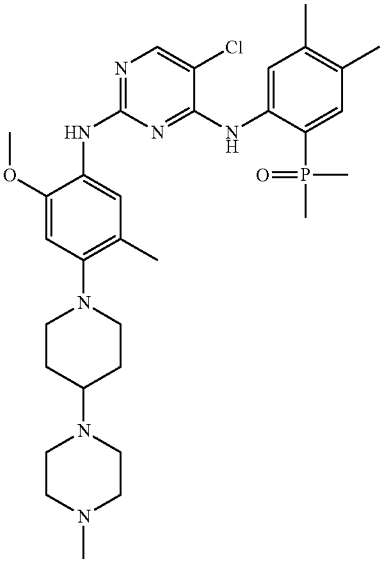

Compound 12

Step 1. (2-((5-Chloro-2-((2-methoxy-5-methyl-4-(4-(4-methylpiperazin-1-yl) piperidin-1-yl)phenyl) amino)pyrimidin-4-yl)amino)-4,5-dimethylphenyl) dimethylphosphine Oxide (Compound 12)

The synthesis steps refer to step 10 of Preparative Embodiment 1. Compound 12 was prepared by replacing compound 1-11 with compound 6-2 and replacing compound 1-5 with compound 2-5. ESI-MS: m/z=626 $[M+1]^+$. $^1H$ NMR (400 MHz, DMSO-$d_6$) δ 10.95 (s, 1H), 8.23 (d, J=4.3 Hz, 1H), 8.05 (s, 1H), 8.00 (s, 1H), 7.36 (s, 1H), 7.30 (d, J=14.1 Hz, 1H), 6.69 (s, 1H), 3.74 (s, 3H), 3.07 (d, J=11.5 Hz, 2H), 2.72-2.52 (m, 6H), 2.42-2.22 (m, 5H), 2.18 (s, 3H), 2.17 (s, 3H), 2.06 (s, 3H), 2.03 (s, 3H), 1.85 (d, J=12.6 Hz, 2H), 1.72 (d, J=13.5 Hz, 6H), 1.61-1.50 (m, 2H).

Preparative Embodiment 8. (2-((5-chloro-2-((5-ethyl-2-methoxy-4-(4-(4-methylpiperazin-1-yl) piperidin-1-yl)phenyl)amino)pyrimidin-4-yl)amino)-4,5-dimethylphenyl)dimethylphosphine Oxide (Compound 11)

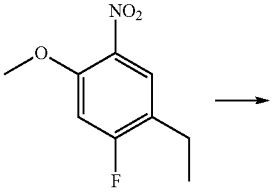

1-8

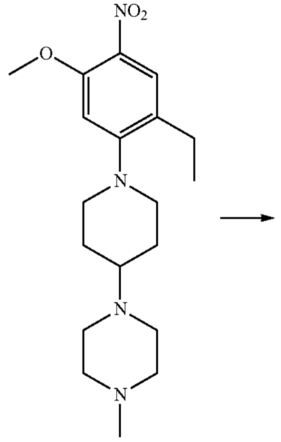

8-1

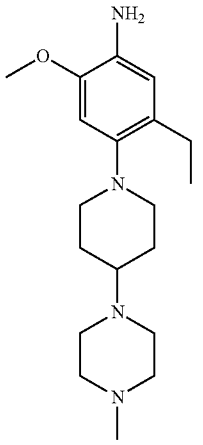

8-2

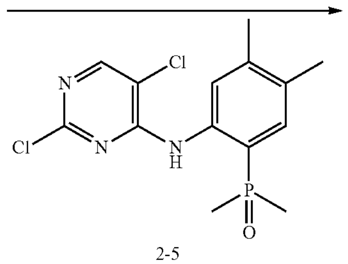

2-5

-continued

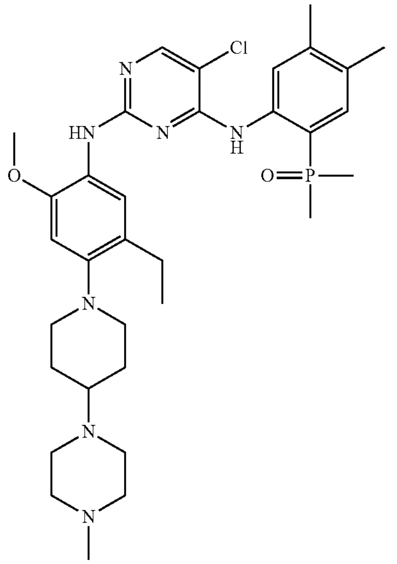

Compound 11

Step 1. 1-(1-(5-methoxy-2-ethyl-4-nitrophenyl) piperidin-4-yl)-4-methylpiperazine (8-1)

The synthesis steps refer to step 7 of Preparative Embodiment 1. Compound 8-1 was prepared by replacing 7-azaspiro[3.5]nonane-2-one with 1-methyl-4-(piperidin-4-yl) piperazine. ESI-MS: m/z=363 $[M+1]^+$.

Step 2. 1-(1-(5-Methoxy-2-ethyl-4-aminophenyl) piperidin-4-yl)-4-methylpiperazine (8-2)

The synthesis steps refer to step 9 of Preparative Embodiment 1. Compound 6-3 was prepared by replacing compound 1-10 with compound 8-1. ESI-MS: m/z=333 $[M+1]^+$.

Step 3. (2-((5-chloro-2-((5-ethyl-2-methoxy-4-(4-(4-methylpiperazin-1-yl) piperidin-1-yl)phenyl)amino) pyrimidin-4-yl)amino)-4,5-dimethylphenyl)dimethylphosphine Oxide (Compound 11)

The synthesis steps refer to step 10 of Preparative Embodiment 1. Compound 11 was prepared by replacing compound 1-11 with compound 8-2. ESI-MS: m/z=640 $[M+1]^+$. $^1H$ NMR (400 MHz, Chloroform-d) δ 10.39 (s, 1H), 8.23 (s, 1H), 8.06 (s, 1H), 8.02 (s, 1H), 7.31 (s, 1H), 7.01 (d, J=14.1 Hz, 1H), 6.61 (s, 1H), 3.83 (s, 3H), 3.48 (s, 2H), 3.09 (d, J=12.8 Hz, 9H), 2.67 (dd, J=27.0, 13.2 Hz, 6H), 2.47 (s, 2H), 2.22 (d, J=30.6 Hz, 6H), 2.05 (s, 2H), 1.79 (d, J=13.2 Hz, 6H), 0.96 (s, 3H).

Preparative Embodiment 9. (2-((5-Chloro-2-((4-(2-(dimethylamino)-7-azaspiro[3.5]nonane-7-yl)-5-ethyl-2-methoxyphenyl)amino)pyrimidin-4-yl) amino)-4,5-dimethylphenyl)dimethylphosphine Oxide (Compound 17)

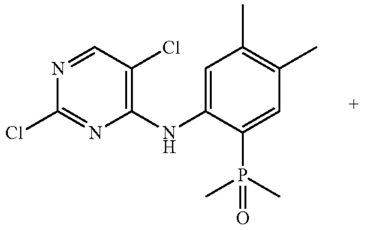

2-5

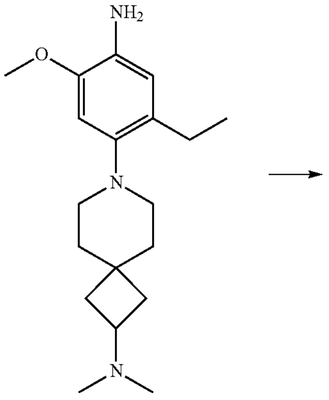

1-11

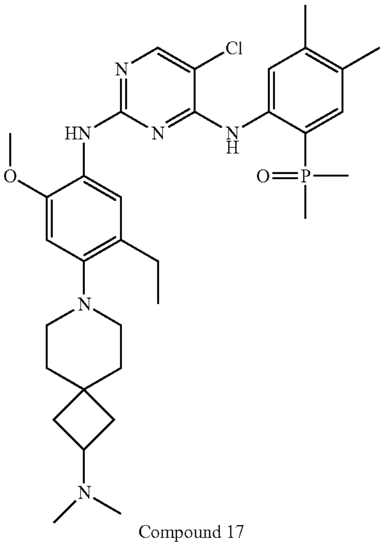

Compound 17

Step 1. (2-((5-Chloro-2-((4-(2-(dimethylamino)-7-azaspiro[3.5]nonane-7-yl)-5-ethyl-2-methoxyphenyl) amino)pyrimidin-4-yl)amino)-4,5-dimethylphenyl) dimethylphosphine Oxide (Compound 17)

The synthesis steps refer to step 10 of Preparative Embodiment 1. Compound 17 was prepared by replacing compound 1-5 with compound 2-5; ESI-MS: m/z=625 $[M+1]^+$. $^1H$ NMR (400 MHz, Chloroform-d) δ 10.38 (s, 1H), 8.25 (s, 1H), 8.07 (s, 1H), 8.00 (s, 1H), 7.26 (s, 1H), 7.00 (d, J=13.9 Hz, 1H), 6.62 (s, 1H), 3.84 (s, 3H), 2.81 (s, 1H), 2.72 (d, J=23.3 Hz, 4H), 2.53-2.46 (m, 2H), 2.28 (s, 6H), 2.11 (s, 2H), 1.87 (dd, J=11.6, 8.4 Hz, 2H), 1.79 (d, J=13.1 Hz, 6H), 1.73 (s, 4H), 1.26 (d, J=12.7 Hz, 6H), 0.97 (s, 3H).

Preparative Embodiment 10. (2-((5-Chloro-2-((4-(2-(dimethylamino)-7-azaspiro[3.5]non-7-yl)-5-ethyl-2-methoxyphenyl)amino)pyrimidin-4-yl)amino)-4,6-dimethylphenyl)dimethylphosphine Oxide (Compound 18)

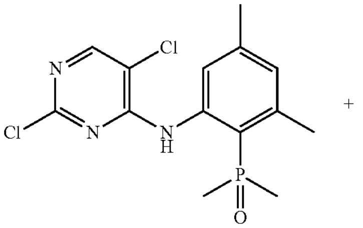

10-1

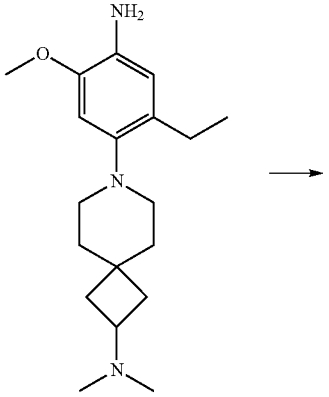

1-11

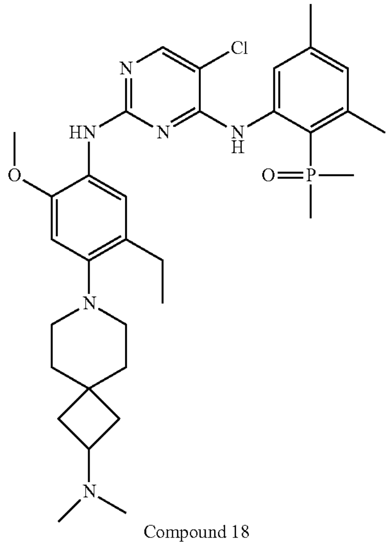

Compound 18

Step 1. (2-((2,5-dichloropyrimidin-4-yl)amino)-4,6-dimethylphenyl)dimethylphosphine Oxide (10-1)

The synthesis steps refer to steps 1 to 4 of Preparative Embodiment 1. Compound 10-1 was prepared by replacing 2,3-dimethyl-6-nitroaniline with 2,4-dimethyl-6-nitroaniline; ESI-MS: m/z=344 [M+1]$^+$.

Step 2. (2-((5-Chloro-2-((4-(2-(dimethylamino)-7-azaspiro[3.5]nonane-7-yl)-5-ethyl-2-methoxyphenyl)amino)pyrimidin-4-yl)amino)-4,6-dimethylphenyl)dimethylphosphine Oxide (Compound 18)

The synthesis steps refer to step 10 of Preparative Embodiment 1. Compound 18 was prepared by replacing compound 1-5 with compound 10-1; ESI-MS: m/z=625 [M+1]$^+$. $^1$H NMR (400 MHz, Chloroform-d) δ 11.83 (s, 1H), 8.07 (s, 1H), 8.01 (s, 1H), 7.91 (s, 1H), 7.52 (s, 1H), 6.74 (s, 1H), 6.58 (s, 1H), 3.82 (s, 3H), 3.41 (s, 1H), 2.74 (d, J=10.8 Hz, 2H), 2.69 (s, 6H), 2.55 (d, J=3.5 Hz, 2H), 2.45 (d, J=11.4 Hz, 2H), 2.40 (s, 3H), 2.25 (d, J=3.5 Hz, 2H), 2.15 (s, 3H), 2.05 (s, 2H), 1.91 (d, J=11.9 Hz, 8H), 1.73 (s, 2H), 0.95 (s, 3H).

Preparative Embodiment 11. (2-((5-Chloro-2-((5-ethyl-2-methoxy-4-(2-methyl-2,7-diazaspiro[3.5]nonane-7-yl)phenyl)amino)pyrimidin-4-yl)amino)-4,5-dimethylphenyl)dimethylphosphine Oxide (Compound 20)

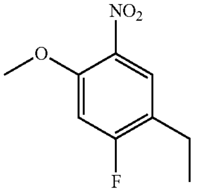

1-8

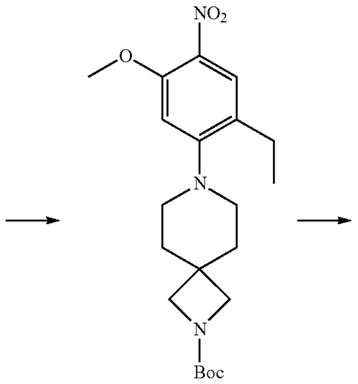

11-1

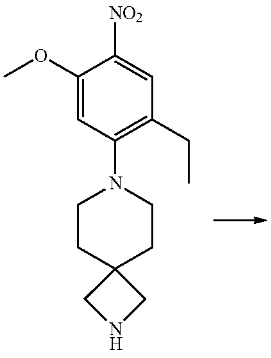

11-2

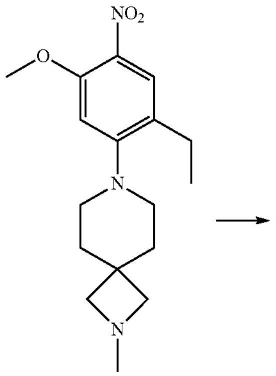

11-3

-continued

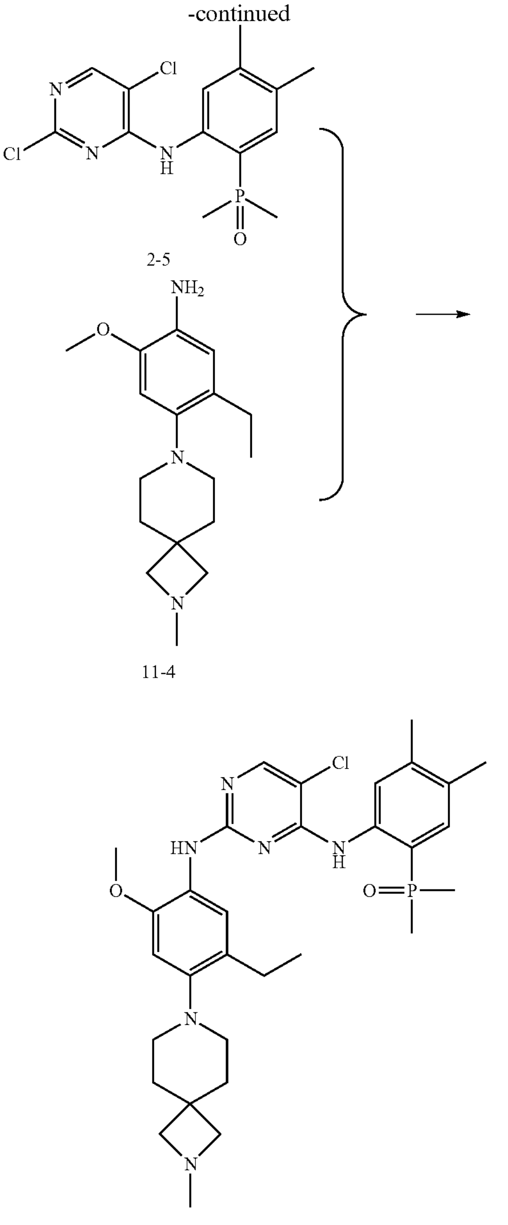

2-5

11-4

Compound 20

Step 1. Tert-butyl 7-(2-ethyl-5-methoxy-4-nitrophenyl)-2,7-diazaspiro[3.5]nonane-2-carboxylate (11-1)

The synthesis steps refer to step 7 of Preparative Embodiment 1. Compound 11-1 was prepared by replacing 7-azaspiro[3.5]nonane-2-one with tert-butyl 2,7-diazaspiro[3.5]nonane-2-carboxylate; ESI-MS: m/z=406 $[M+1]^+$.

Step 2. 7-(2-Ethyl-5-methoxy-4-nitrophenyl)-2,7-diazaspiro[3.5]nonane (11-2)

The synthesis steps refer to step 5 of Preparative Embodiment 3. Compound 11-2 was prepared by replacing the intermediate 3-5 with the intermediate 11-1; ESI-MS: m/z=306 $[M+1]^+$.

Step 3. 7-(2-Ethyl-5-methoxy-4-nitrophenyl)-2-methyl-2,7-diazaspiro[3.5]nonane (11-3)

The synthesis steps refer to step 8 of Preparative Embodiment 1. Compound 11-3 was prepared by replacing dimethylamine with paraformaldehyde; ESI-MS: m/z=320 $[M+1]^+$.

Step 4. 7-(2-Ethyl-5-methoxy-4-aminophenyl)-2-methyl-2,7-diazaspiro[3.5]nonane (11-4)

The synthesis steps refer to step 9 of Preparative Embodiment 1. Compound 11-4 was prepared by replacing the intermediate 1-10 with the intermediate 11-3; ESI-MS: m/z=290 $[M+1]^+$.

Step 5. (2-((5-Chloro-2-((5-ethyl-2-methoxy-4-(2-methyl-2,7-diazaspiro[3.5]nonane-7-yl)phenyl)amino)pyrimidin-4-yl)amino)-4,5-dimethylphenyl)dimethylphosphine Oxide (Compound 20)

The synthesis steps refer to step 10 of Preparative Embodiment 1. Compound 20 was prepared by replacing compound 1-11 with compound 11-4 and replacing compound 1-5 with compound 2-5; ESI-MS: m/z=597 $[M+1]^+$. $^1H$ NMR (400 MHz, Chloroform-d) δ 10.44 (s, 1H), 8.24 (s, 1H), 8.03 (d, J=19.3 Hz, 2H), 7.36 (s, 1H), 7.01 (d, J=13.9 Hz, 1H), 6.55 (s, 1H), 3.83 (s, 3H), 2.91 (s, 3H), 2.75 (s, 4H), 2.47 (d, J=10.6 Hz, 2H), 2.25 (s, 3H), 2.17 (s, 3H), 1.95 (dd, J=30.0, 17.5 Hz, 8H), 1.81 (s, 3H), 1.78 (s, 3H), 0.98-0.93 (m, 3H).

Preparative Embodiment 12. (6-((5-chloro-2-((4-(2-(dimethylamino)-7-azaspiro[3.5]nonan-7-yl)-2-methoxyphenyl)amino)pyrimidin-4-yl)amino)-2,3-dimethylphenyl)dimethylphosphine Oxide (Compound 22)

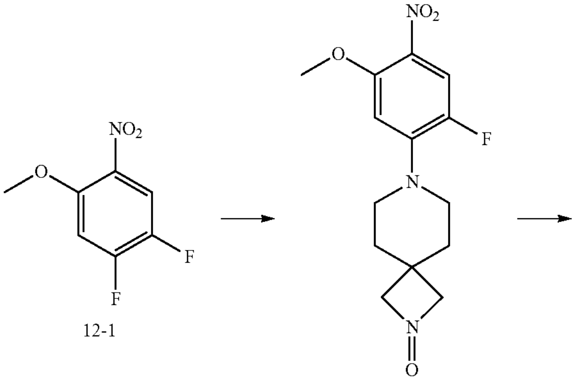

12-1

12-2

-continued

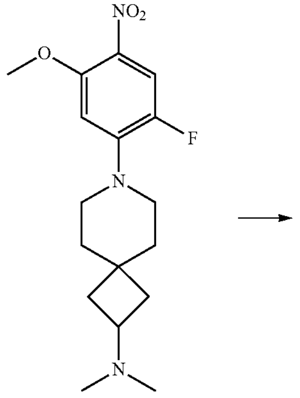

12-3

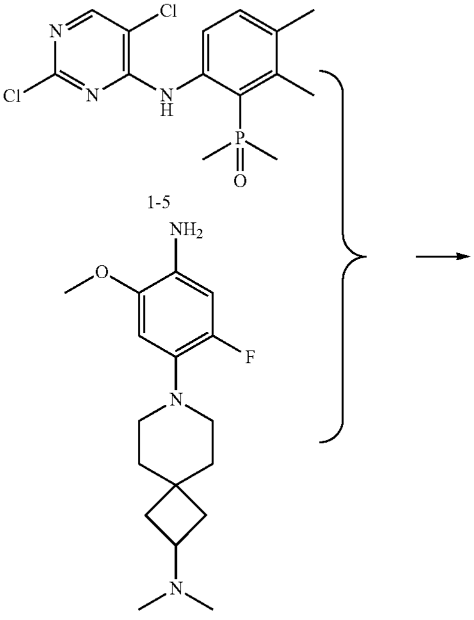

1-5

12-4

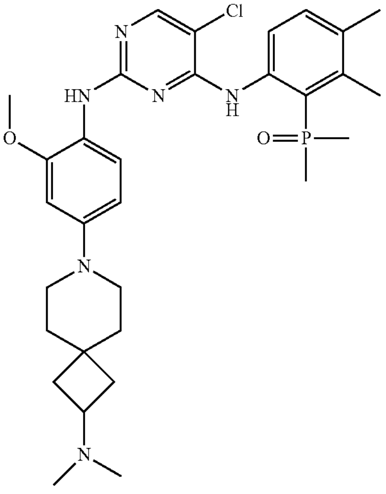

Compound 22

Step 1. 7-(2-fluoro-5-methoxy-4-nitrophenyl)-7-azaspiro[3.5]nonan-2-one (12-2)

The synthesis steps refer to step 7 of Preparative Embodiment 1. Compound 12-2 was prepared by replacing the intermediate 1-8 with 4,5-difluoro-2-methoxy-1-nitrobenzene; ESI-MS: m/z=309 $[M+1]^+$.

Step 2.

7-(2-fluoro-5-methoxy-4-nitrophenyl)-N,N-dimethyl-7-azaspiro[3.5]nonan-2-amine (12-3)

The synthesis steps refer to step 8 of Preparative Embodiment 1. Compound 12-3 was prepared by replacing the intermediate 1-9 with the intermediate 12-2; ESI-MS: m/z=338 $[M+1]^+$.

Step 3. 7-(4-amino-2-fluoro-5-methoxyphenyl)-N,N-dimethyl-7-azaspiro[3.5]nonan-2-amine (12-4)

The synthesis steps refer to step 9 of Preparative Embodiment 1. Compound 12-4 was prepared by replacing the intermediate 1-10 with the intermediate 12-3; ESI-MS: m/z=308 $[M+1]^+$.

Step 5. (6-((5-chloro-2-((4-(2-(dimethylamino)-7-azaspiro[3.5]nonan-7-yl)-2-methoxyphenyl)amino)pyrimidin-4-yl)amino)-2,3-dimethylphenyl)dimethylphosphine oxide (compound 22)

The synthesis steps refer to step 10 of Preparative Embodiment 1. Compound 22 was prepared by replacing the intermediate 1-11 with the intermediate 12-4; ESI-MS: m/z=615 $[M+1]^+$. $^1$H NMR (400 MHz, Chloroform-d) δ 11.85 (s, 1H), 8.15 (d, J=12.2 Hz, 2H), 8.02 (s, 1H), 7.39 (s, 2H), 6.50 (d, J=7.5 Hz, 1H), 3.82 (s, 3H), 2.90 (d, J=29.8 Hz, 4H), 2.63 (d, J=10.1 Hz, 1H), 2.28 (t, J=6.0 Hz, 6H), 2.14 (s, 6H), 2.06 (s, 4H), 1.96 (d, J=12.7 Hz, 6H), 1.75 (d, J=18.0 Hz, 4H).

Preparative Embodiment 13. (6-((5-Chloro-2-((5-ethyl-2-methoxy-4-(7-methyl-2,7-diazaspiro[3.5]non-2-yl)phenyl)amino)pyrimidin-4-yl)amino)-2,3-dimethylphenyl)dimethylphosphine oxide (compound 24)

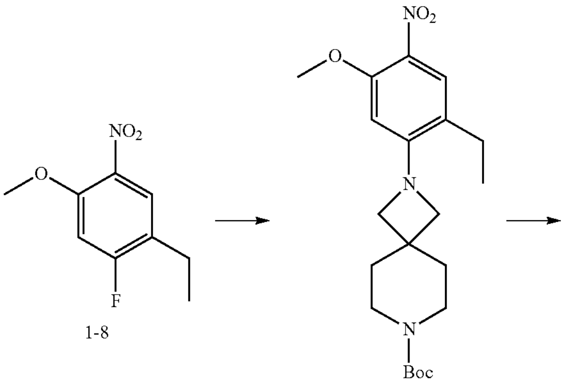

1-8

13-1

-continued

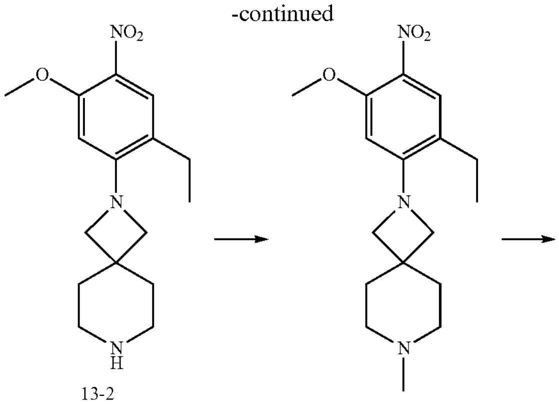

13-2

13-3

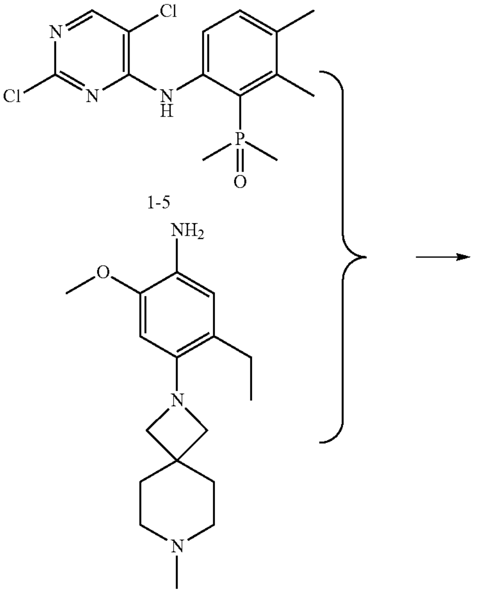

1-5

13-4

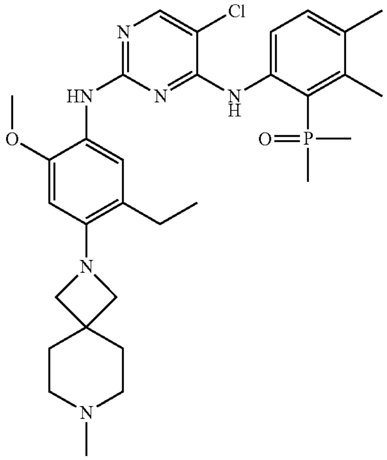

Compound 24

Step 1. Tert-butyl 2-(5-methoxy-2-ethyl-4-nitrophenyl)-2,7-diazaspiro[3.5]nonane-7-carboxylate (13-1)

The synthesis steps refer to step 7 of Embodiment 1. Compound 13-1 was prepared by replacing 7-azaspiro[3.5]nonane-2-one with tert-butyl 2,7-diazaspiro[3.5]nonane-7-carboxylate; ESI-MS: m/z=406 $[M+1]^+$.

Step 2. 2-(2-Ethyl-5-methoxy-4-nitrophenyl)-2,7-diazaspiro[3.5]nonane (12-2)

The synthesis steps refer to step 5 of Preparative Embodiment 3. Compound 12-2 was prepared by replacing the intermediate 3-5 with the intermediate 11-1; ESI-MS: m/z=306 $[M+1]^+$.

Step 3. 2-(2-Ethyl-5-methoxy-4-nitrophenyl)-7-methyl-2,7-diazaspiro[3.5]nonane (13-3)

The synthesis steps refer to step 8 of Embodiment 1. Compound 13-3 was prepared by replacing dimethylamine with paraformaldehyde; ESI-MS: m/z=320 $[M+1]^+$.

Step 4. 2-(2-Ethyl-5-methoxy-4-aminophenyl)-7-methyl-2,7-diazaspiro[3.5]nonane (13-4)

The synthesis steps refer to step 9 of Preparative Embodiment 1. Compound 11-4 was prepared by replacing the intermediate 1-10 with the intermediate 13-3; ESI-MS: m/z=290 $[M+1]^+$.

Step 5. (6-((5-Chloro-2-((5-ethyl-2-methoxy-4-(7-methyl-2,7-diazaspiro[3.5]nonane-2-yl)phenyl)amino)pyrimidin-4-yl)amino)-2,3-dimethylphenyl)dimethylphosphine Oxide (Compound 24)

The synthesis steps refer to step 10 of Preparative Embodiment 1. Compound 24 was prepared by replacing the intermediate 1-11 with the intermediate 13-4; ESI-MS: m/z=597 $[M+1]^+$. $^1H$ NMR (400 MHz, Chloroform-d) δ 11.79 (s, 1H), 8.22 (s, 1H), 8.01 (s, 1H), 7.87 (s, 1H), 7.23 (s, 1H), 7.17 (s, 1H), 6.06 (s, 1H), 3.83 (s, 3H), 3.67 (s, 4H), 2.74 (s, 3H), 2.56-2.11 (m, 16H), 1.97 (d, J=12.9 Hz, 6H), 1.04 (s, 3H).

Preparative Embodiment 14. (6-((5-Chloro-2-((4-(7-(dimethylamino)-2-azaspiro[3.5]nonane-2-yl)-2-methoxyphenyl)amino)pyrimidin-4-yl)amino)-2,3-dimethylphenyl)dimethylphosphine Oxide (Compound 2)

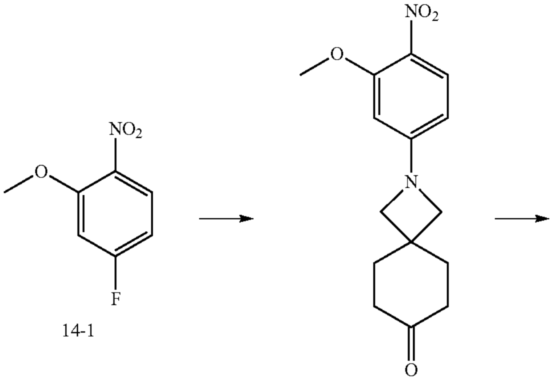

14-1

14-2

-continued

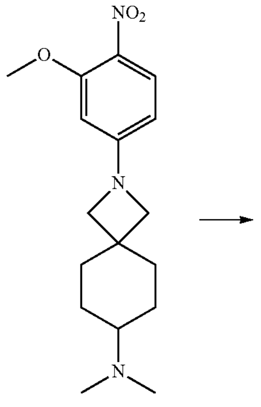

14-3

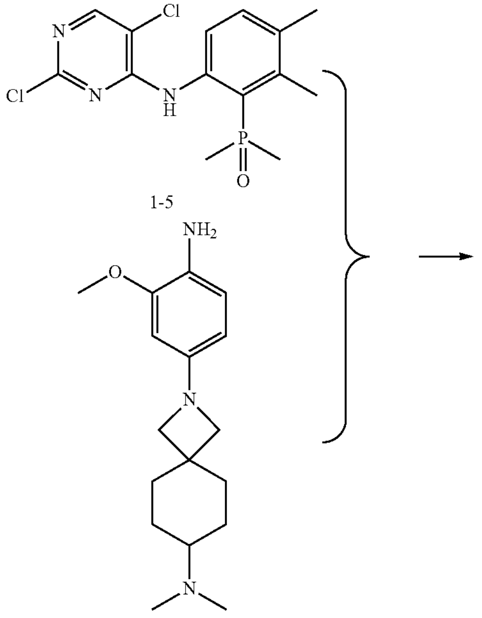

1-5

14-4

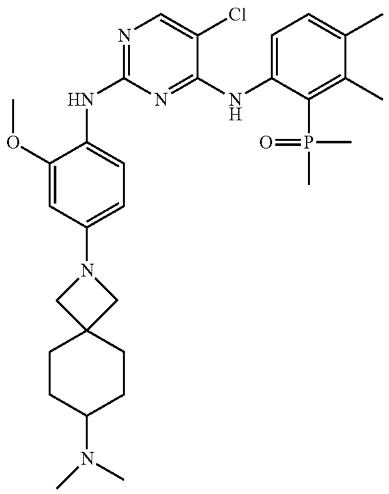

Compound 2

Step 1. 2-(3-methoxy-4-nitrophenyl)-2-azaspiro[3.5]nonan-7-one (14-2)

The synthesis steps refer to step 7 of Preparative Embodiment 1. The intermediate 14-2 was prepared by replacing the intermediate 1-7 with compound 14-1 and replacing 7-azaspiro[3.5]nonan-2-one with 2-azaspiro[3.5]nonan-7-one; ESI-MS: m/z=291 $[M+1]^+$.

Step 2. 2-(3-Methoxy-4-nitrophenyl)-N,N-dimethyl-2-azaspiro[3.5]nonan-7-amine (14-3)

The synthesis steps refer to step 8 of Preparative Embodiment 1. Compound 14-3 was prepared by replacing the intermediate 1-9 with the intermediate 14-2; ESI-MS: m/z=320 $[M+1]^+$.

Step 3. 2-(4-Amino-3-methoxyphenyl)-N,N-dimethyl-2-azaspiro[3.5]nonan-7-amine (14-4)

The synthesis steps refer to step 9 of Embodiment 1. Compound 14-4 was prepared by replacing the intermediate 1-10 with the intermediate 14-3; ESI-MS: m/z=290 $[M+1]^+$.

Step 4. (6-((5-Chloro-2-((4-(7-(dimethylamino)-2-azaspiro[3.5]nonane-2-yl)-2-methoxyphenyl)amino)pyrimidin-4-yl)amino)-2,3-dimethylphenyl)dimethylphosphine Oxide (Compound 2)

The synthesis steps refer to step 10 of Preparative Embodiment 1. Compound 2 was prepared by replacing the intermediate 1-11 with the compound 14-4; ESI-MS: m/z=597 $[M+1]^+$.

Preparative Embodiment 15. (6-((5-Chloro-2-((4-(7-(dimethylamino)-2-azaspiro[3.5]nonan-2-yl)-2-methoxy-5-methylphenyl)amino)pyrimidin-4-yl)amino)-2,3-dimethylphenyl)dimethylphosphine Oxide (Compound 3)

The synthesis steps refer to Preparative Embodiment 14. Compound 3 was prepared by replacing the intermediate 14-1 with the intermediate 3-2; ESI-MS: m/z=611 $[M+1]^+$.

Preparative Embodiment 16. (6-((5-Chloro-2-((2-methoxy-4-(9-methyl-3,9-diazaspiro[5.5]undecan-3-yl)phenyl)amino)pyrimidin-4-yl)amino)-2,3-dimethylphenyl)dimethylphosphine Oxide (Compound 4)

The synthesis steps refer to Preparative Embodiment 13. The compound 4 was prepared by replacing the intermediate 1-5 with compound 14-1 and replacing tert-butyl 2,7-diazaspiro[3.5]nonane-7-carboxylate with tert-butyl 3,9-diazaspiro[5.5]undecan-3-formate; ESI-MS: m/z=597 $[M+1]^+$.

Preparative Embodiment 17. (2-((5-Chloro-2-((4-(2-(dimethylamino)-7-azaspiro[3.5]nonan-7-yl)-2-methoxy-5-methylphenyl)amino)pyrimidin-4-yl)amino)-4,5-dimethylphenyl)dimethylphosphine oxide (compound 9)

The synthesis steps refer to Preparative Embodiment 2. Compound 9 was prepared by replacing the intermediate 2-1 with the intermediate 3-2; ESI-MS: m/z=611 $[M+1]^+$.

Preparative Embodiment 18. (2-((5-Chloro-2-((4-(7-(dimethylamino)-2-azaspiro[3.5]nonan-2-yl)-5-ethyl-2-methoxyphenyl)amino)pyrimidin-4-yl)amino)-4,5-dimethylphenyl)dimethylphosphine oxide (compound 10)

The synthesis steps refer to Preparative Embodiment 9. The compound 10 was prepared by replacing 7-azaspiro[3.5]nonan-2-one with 2-azaspiro[3.5]nonan-7-one; ESI-MS: m/z=625 $[M+1]^+$.

Preparative Embodiment 19. (2-((5-Chloro-2-((5-chloro-4-(2-(dimethylamino)-7-azaspiro[3.5]nonan-7-yl)-2-methoxyphen yl)amino)pyrimidin-4-yl)amino)-4,5-dimethylphenyl)dimethylphosphine oxide (compound 13)

The synthesis steps refer to Preparative Embodiment 12. The compound 13 was prepared by replacing the intermediate 12-1 with 1-chloro-2-fluoro-4-methoxy-5-nitrobenzene and replacing compound 1-5 with compound 2-5; ESI-MS: m/z=631 $[M+1]^+$.

Preparative Embodiment 20. (2-((5-chloro-2-((5-ethyl-2-methoxy-4-(4-morpholinopiperidin-1-yl)phenyl)amino)pyrimidin-4-yl)amino)-4,5-dimethylphenyl)dimethylphosphine Oxide (Compound 14)

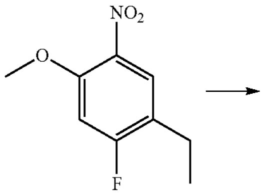

1-8

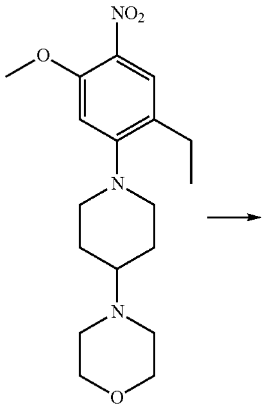

20-1

-continued

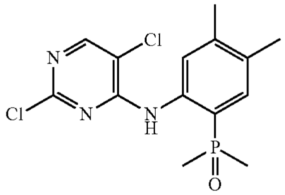

2-5

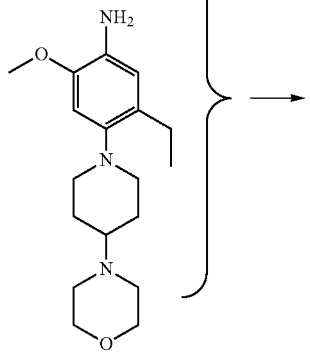

20-2

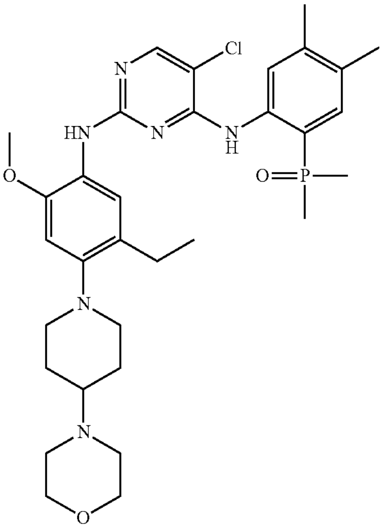

Compound 14

The synthesis steps refer to Preparative Embodiment 8. The compound 14 was prepared by replacing 1-methyl-4-(piperidin-4-yl) piperazine with 4-(4-piperidyl) morpholine; ESI-MS: m/z=627 $[M+1]^+$.

Preparative Embodiment 21. (2-((5-chloro-2-((4-(4-(3-(dimethylamino) azetidin-1-yl) piperidine-1-yl)-5-ethyl-2-methoxyphenyl)amino)pyrimidin-4-yl) amino)-4,5-dimethylphenyl)dimethylphosphine Oxide (Compound 15)

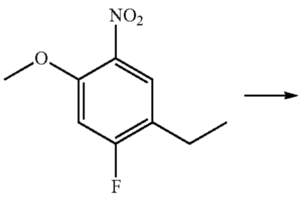

1-8

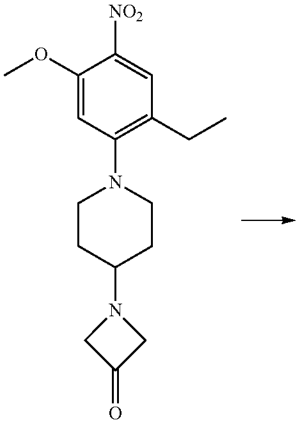

21-1

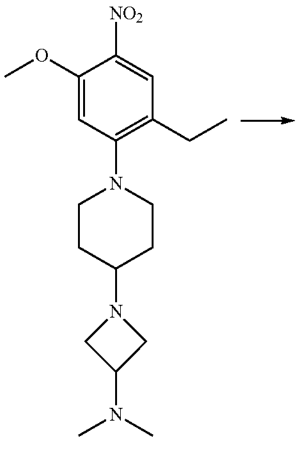

21-2

-continued

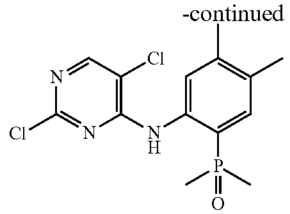

2-5

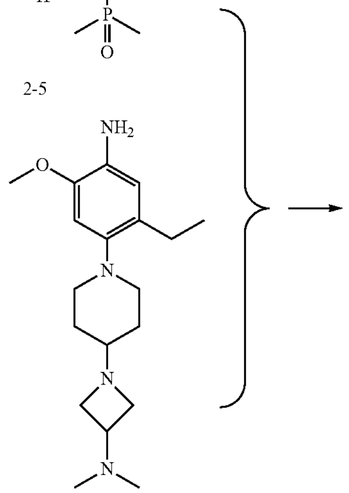

21-3

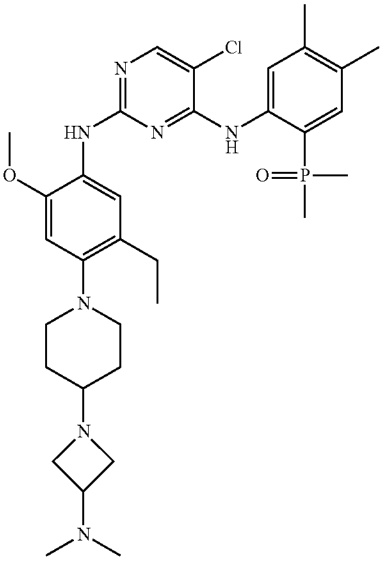

Compound 15

Step 1. 1-(1-(2-ethyl-5-methoxy-4-nitrophenyl) piperidin-4-yl) azetidin-3-one (21-1)

The synthesis steps refer to step 7 of Preparative Embodiment 1. The intermediate 21-1 was prepared by replacing 7-azaspiro[3.5]nonan-2-one with 1-(piperidin-4-yl)azetidin-3-one; ESI-MS: m/z=334 $[M+1]^+$.

Step 2. 1-(1-(2-ethyl-5-methoxy-4-nitrophenyl)piperidin-4-yl)-N,N-dimethylazetidin-3-amine (21-2)

The synthesis steps refer to step 8 of Preparative Embodiment 1. Compound 21-2 was prepared by replacing the intermediate 1-9 with the intermediate 21-1; ESI-MS: m/z=363 $[M+1]^+$.

Step 3. 1-(1-(4-amino-2-ethyl-5-methoxyphenyl)piperidin-4-yl)-N,N-dimethylazetidin-3-amine (21-3)

The synthesis steps refer to step 9 of Preparative Embodiment 1. Compound 21-3 was prepared by replacing the intermediate 1-10 with the intermediate 21-2; ESI-MS: m/z=333 $[M+1]^+$.

Step 4. (2-((5-chloro-2-((4-(4-(3-(dimethylamino)azetidin-1-yl)piperidine-1-yl)-5-ethyl-2-methoxyphenyl)amino)pyrimidin-4-yl)amino)-4,5-dimethylphenyl)dimethylphosphine oxide (compound 15)

The synthesis steps refer to step 10 of Preparative Embodiment 1. Compound 15 was prepared by replacing compound 1-5 with compound 2-5 and replacing compound 1-11 with compound 21-3; ESI-MS: m/z=640 $[M+1]^+$.

Preparative Embodiment 22. (2-((5-chloro-2-((4-(2-(dimethylamino)-7-azaspiro[3.5]nonan-7-yl)-5-fluoro-2-methoxyphenyl)amino)pyrimidin-4-yl)amino)-4,5-dimethylphenyl)dimethylphosphine oxide (compound 16)

The synthesis steps refer to Preparative Embodiment 12. Compound 16 was prepared by replacing the intermediate 1-5 with the intermediate 2-5; ESI-MS: m/z=615 $[M+1]^+$.

Preparative Embodiment 23. (2-chloro-6-((5-chloro-2-((4-(2-(dimethylamino)-7-azaspiro[3.5]nonan-7-yl)-5-ethyl-2-methoxyphenyl)amino)pyrimidin-4-yl)amino)phenyl)dimethylphosphine Oxide (Compound 19)

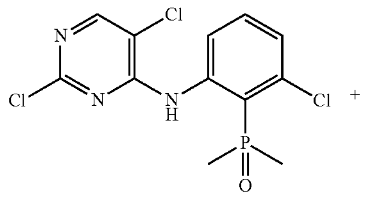

23-1

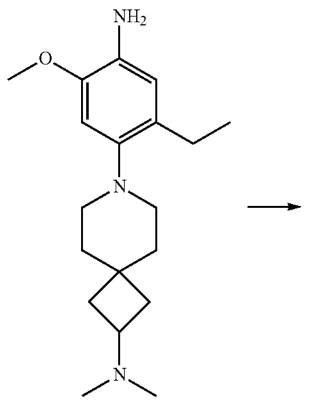

1-11

-continued

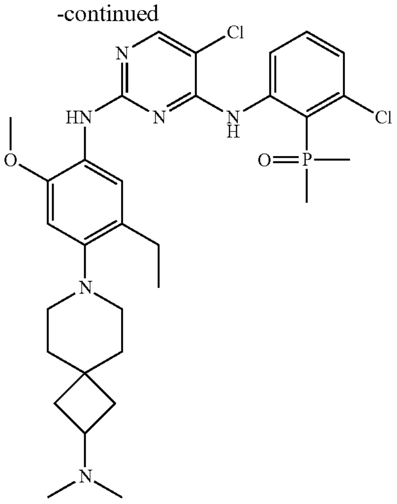

Compound 19

Step 1. (2-chloro-6-((2,5-dichloropyrimidin-4-yl)amino)phenyl)dimethylphosphine oxide (23-1)

The synthesis steps refer to steps 1 to 4 of Preparative Embodiment 1. Compound 23-1 was prepared by replacing the intermediate 1-1 with compound 2-chloro-6-nitroaniline; ESI-MS: m/z=350 $[M+1]^+$.

Step 2. (2-chloro-6-((5-chloro-2-((4-(2-(dimethylamino)-7-azaspiro[3.5]nonane-7-yl)-5-ethyl-2-methoxyphenyl)amino)pyrimidin-4-yl)amino)phenyl)dimethylphosphine Oxide (Compound 19)

The synthesis steps refer to step 10 of Preparative Embodiment 1. Compound 19 was prepared by replacing the intermediate 1-5 with the intermediate 23-1; ESI-MS: m/z=631 $[M+1]^+$.

Preparative Embodiment 24. (6-((5-chloro-2-((5-chloro-4-(2-(dimethylamino)-7-azaspiro[3.5]nonan-7-yl)-2-methoxyphen yl)amino)pyrimidin-4-yl)amino)-2,3-dimethylphenyl)dimethylphosphine Oxide (Compound 21)

The synthesis steps refer to Preparative Embodiment 12. Compound 21 was prepared by replacing the intermediate 12-1 with 1-chloro-2-fluoro-4-methoxy-5-nitrobenzene; ESI-MS: m/z=631 $[M+1]^+$.

Preparative Embodiment 25. (6-((5-chloro-2-((4-(2-(dimethylamino)-7-azaspiro[3.5]nonan-7-yl)-2-methoxy-5-methylphen yl)amino)pyrimidin-4-yl)amino)-2,3-dimethylphenyl)dimethylphosphine oxide (compound 23)

The synthesis steps refer to Preparative Embodiment 2. Compound 23 was prepared by replacing compound 2-5 with compound 1-5 and replacing compound 2-1 with compound 3-2; ESI-MS: m/z=611 $[M+1]^+$.

Preparative Embodiment 26

Referring to Preparative Embodiment 13, Replace Paraformaldehyde with Different Aldehydes to Synthesize the Following Compounds.

| Compound No. | Aldehydes after replacement | ESI-MS: m/z |
|---|---|---|
| Compound 25 | Cyclopropanone | 623 |
| Compound 26 | Cyclopropanecarboxaldehyde | 637 |
| Compound 27 | Acetaldehyde | 611 |
| Compound 28 | 2,2-Difluoroacetaldehyde | 647 |
| Compound 31 | Methyl formate | 627 |

Preparative Embodiment 27

Referring to Preparative Embodiment 13, replace compound 1-6 with compound 3-2 and replace paraformaldehyde with different aldehydes to synthesize the following compounds.

| Compound No. | Aldehydes after replacement | ESI-MS: m/z |
|---|---|---|
| Compound 32 | Paraformaldehyde | 583 |
| Compound 33 | Acetaldehyde | 597 |

Preparative Embodiment 28

Referring to Preparative Embodiment 13, replace compound 1-6 with 1-chloro-2-fluoro-4-methoxy-5-nitrobenzene and replace paraformaldehyde with different aldehydes to synthesize the following compounds.

| Compound No. | Aldehydes after replacement | ESI-MS: m/z |
|---|---|---|
| Compound 34 | Paraformaldehyde | 603 |
| Compound 35 | Acetaldehyde | 617 |

Preparative Embodiment 29

Referring to Preparative Embodiment 13, replace compound 1-5 with compound 4-1 and replace paraformaldehyde with different aldehydes to synthesize the following compounds.

| Compound No. | Aldehydes after replacement | ESI-MS: m/z |
|---|---|---|
| Compound 36 | Paraformaldehyde | 637 |
| Compound 37 | Cyclopropanone | 663 |
| Compound 38 | 2,2-Difluoroacetaldehyde | 687 |

Preparative Embodiment 30

Referring to Preparative Embodiment 13, replace compound 1-5 with compound 2-5, replace compound 1-6 with 1-chloro-2-fluoro-4-methoxy-5-nitrobenzene, and replace paraformaldehyde with different aldehydes to synthesize the following compounds.

| Compound No. | Aldehydes after replacement | ESI-MS: m/z |
|---|---|---|
| Compound 40 | Paraformaldehyde | 603 |
| Compound 41 | Cyclopropanone | 629 |

-continued

| Compound No. | Aldehydes after replacement | ESI-MS: m/z |
|---|---|---|
| Compound 42 | 2,2-Difluoroacetaldehyde | 653 |

Preparative Embodiment 31

Referring to Preparative Embodiment 13, replace compound 1-5 with compound 2-5 and replace paraformaldehyde with different aldehydes to synthesize the following compounds.

| Compound No. | Aldehydes after replacement | ESI-MS: m/z |
|---|---|---|
| Compound 44 | Paraformaldehyde | 597 |
| Compound 45 | 2,2-Difluoroacetaldehyde | 647 |

Preparative Embodiment 32

Referring to Preparative Embodiment 13, replace compound 1-5 with compound 23-1 and replace paraformaldehyde with different aldehydes to synthesize the following compounds.

| Compound No. | ESI-MS: m/z |
|---|---|
| Compound 46 | 603 |
| Compound 47 | 617 |

Preparative Embodiment 33 2-(2-(4-((5-chloro-4-((2-(dimethylphosphoryl)-3,4-dimethylphenyl)amino)pyrimidin-2-yl)amino)-2-ethyl-5-methoxyphenyl)-2-azaspiro[3.5]nonane-7-yl)acetonitrile (compound 29

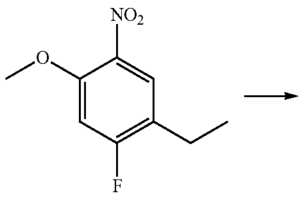

1-8

-continued

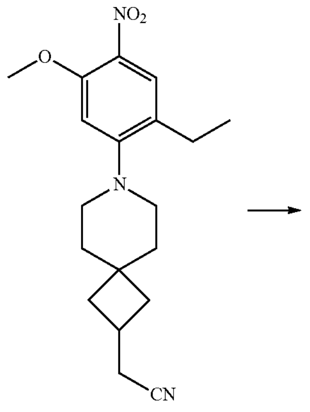

33-1

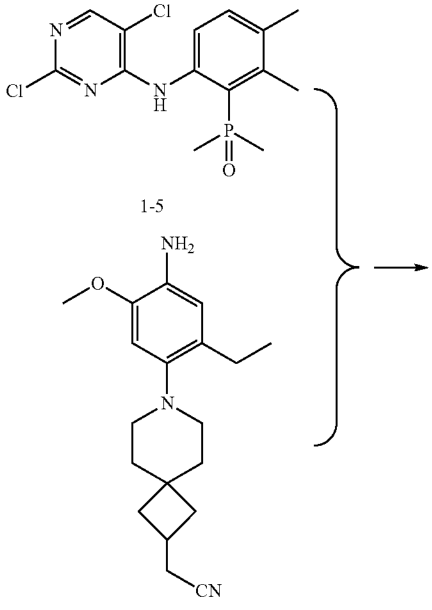

1-5

33-2

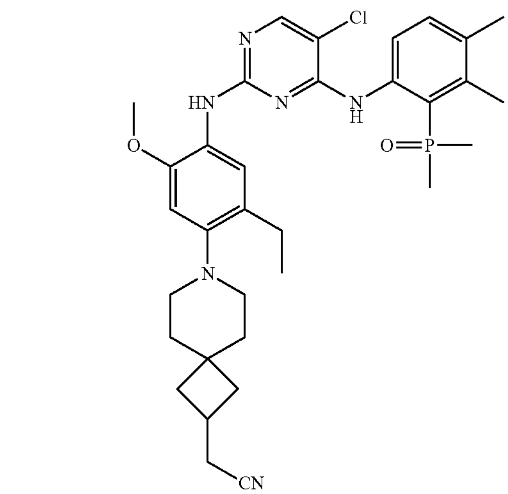

Step 1. 2-(7-(2-ethyl-5-methoxy-4-nitrophenyl)-7-azaspiro[3.5]nonane-2-yl)acetonitrile (33-1)

Referring to step 7 of Preparative Embodiment 1, replace 7-azaspiro[3.5]nonan-2-one with 2-(7-azaspiro[3.5]nonan-2-yl)acetonitrile to obtain the intermediate 33-1; ESI-MS: m/z=344 $[M+1]^+$.

Step 2. 2-(7-(4-amino-2-ethyl-5-methoxyphenyl)-7-azaspiro[3.5]nonan-2-yl)acetonitrile (33-2)

Referring to step 9 of Preparative Embodiment 1, replace compound 1-10 with compound 33-1 to obtain the intermediate 33-2; ESI-MS: m/z=314 $[M+1]^+$.

Step 3. 2-(7-(4-((5-chloro-4-((2-(dimethylphosphoryl)-3,4-dimethylphenyl)amino)pyrimidin-2-yl)amino)-2-ethyl-5-methoxyphenyl)-7-azaspiro[3.5]nonan-2-yl)acetonitrile (compound 29)

Referring to step 10 of Preparative Embodiment 1, replace compound 1-11 with compound 33-2 to obtain compound 29; ESI-MS: m/z=621 $[M+1]^+$.

Preparative Embodiment 34. 1-(7-(4-((5-chloro-4-((2-(dimethylphosphoryl)-3,4-dimethylphenyl)amino)pyrimidin-2-yl)amino)-2-ethyl-5-methoxyphenyl)-2,7-diazaspiro[3.5]nonan-2-yl)ethan-1-one (compound 30)

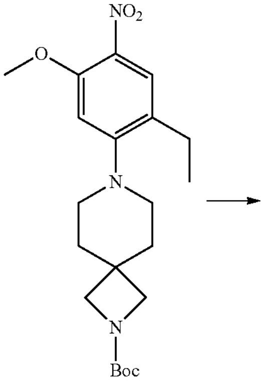

11-1

-continued

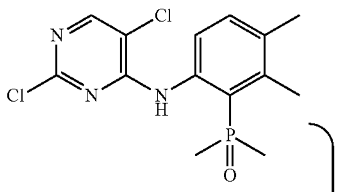

1-5

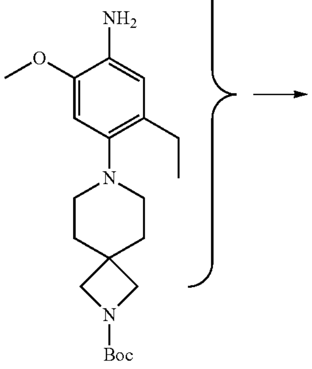

34-1

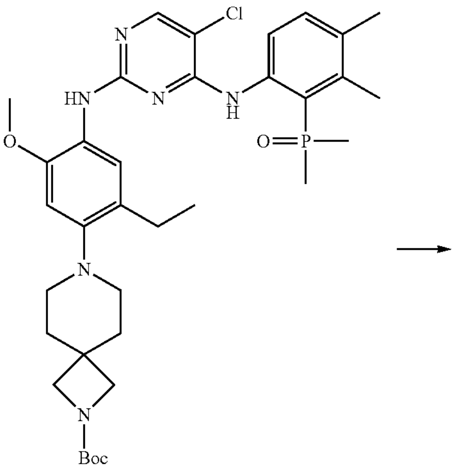

34-2

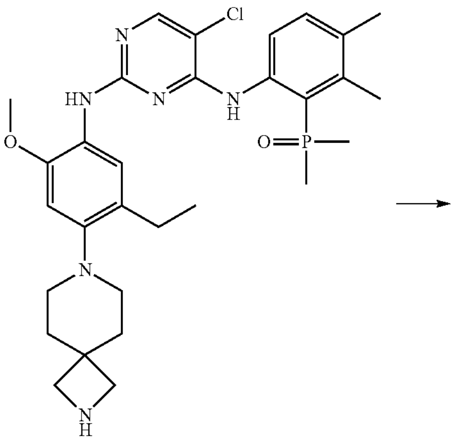

34-3

-continued

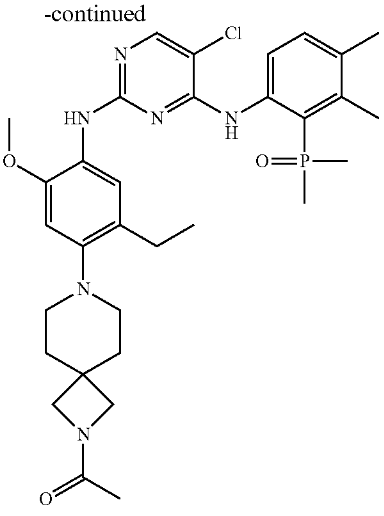

Step 1. Tert-butyl 7-(4-amino-2-ethyl-5-methoxyphenyl)-2,7-diazaspiro[3.5]nonane-2-carboxylate (34-1)

The synthesis steps refer to step 9 of Preparative Embodiment 1. The intermediate 34-1 was prepared by replacing compound 1-10 with compound 11-1; ESI-MS: m/z=376 $[M+1]^+$.

Step 2. Tert-butyl 7-(4-((5-chloro-4-((2-(dimethylphosphoryl)-3,4-dimethylphenyl)amino)pyrimidin-2-yl)amino)-2-ethyl-5-methoxyphenyl)-2,7-diazaspiro[3.5]nonane-2-carboxylate (34-2)

The synthesis steps refer to step 10 of Preparative Embodiment 1. The intermediate 34-2 was prepared by replacing compound 1-11 with compound 34-1; ESI-MS: m/z=683 $[M+1]^+$.

Step 3. (6-((5-chloro-2-((5-ethyl-2-methoxy-4-(2,7-diazaspiro[3.5]nonan-7-yl)phenyl)amino)pyrimidin-4-yl)amino)-2,3-dimethylphenyl)dimethylphosphine oxide (34-3)

The synthesis steps refer to step 5 of Preparative Embodiment 3. The intermediate 34-3 was prepared by replacing compound 3-5 with compound 34-2; ESI-MS: m/z=583 $[M+1]^+$.

Step 4. 1-(7-(4-((5-chloro-4-((2-(dimethylphosphoryl)-3,4-dimethylphenyl)amino)pyrimidin-2-yl)amino)-2-ethyl-5-methoxyphenyl)-2,7-diazaspiro[3.5]nonan-2-yl)ethan-1-one (compound 30)

The intermediate 34-3 (200 mg) was dissolved in dichloromethane (5 ml). Triethylamine (70 mg) was added. acetylchloride (32 mg) was slowly added under an ice bath. Stirring was conducted for 1 hour. After the reaction was detected with TLC, the solvent was recovered under reduced pressure to obtain a residue. The residue was purified with silica gel column chromatography using DCM:MeOH (25:1) as an eluent to obtain a crude product, which was purified with a silica gel preparation plate using DCM:MeOH (30:1) as a developing solvent to obtain a white solid; ESI-MS: m/z=625 $[M+H]^+$.

Preparative Embodiment 35. 2-(2-(4-((5-chloro-4-((4,5-dichloro-2-(dimethylphosphoryl)phenyl)amino)pyrimidin-2-yl)amino)-2-ethyl-5-methoxyphenyl)-2-azaspiro[3.5]nonan-7-yl)acetonitrile (compound 39)

Referring to Preparative Embodiment 33, compound 39 was prepared by replacing compound 1-5 with compound 4-1; ESI-MS: m/z=661 $[M+H]^+$.

Preparative Embodiment 36. 2-(2-(2-chloro-4-((5-chloro-4-((2-(dimethylphosphoryl)-4,5-dimethylphenyl)amino)pyrimidin-2-yl)amino)-5-methoxyphenyl)-2-azaspiro[3.5]nonan-7-yl)acetonitrile (compound 43)

Referring to Preparative Embodiment 33, compound 43 was prepared by replacing compound 1-5 with compound 2-5 and replacing compound 1-6 with 1-chloro-2-fluoro-4-methoxy-5-nitrobenzene; ESI-MS: m/z=627 $[M+H]^+$.

Preparative Embodiment 37. (6-((5-chloro-2-((5-ethyl-2-methoxy-4-(2-(pyrrolidin-1-yl)-7-azaspiro[3.5]nonan-7-yl)phenyl)amino)pyrimidin-4-yl)amino)-2,3-dimethylphenyl)dimethylphosphine oxide (compound 48)

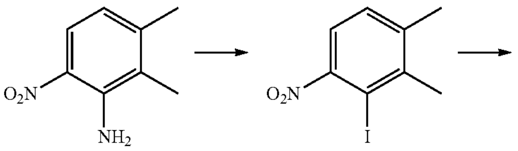

1-1 1-2

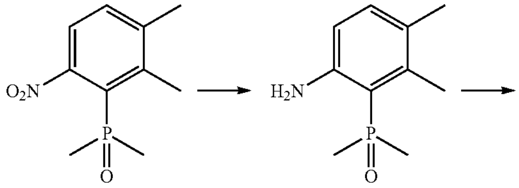

1-3 1-4

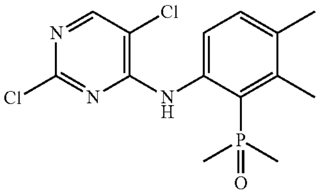

1-5

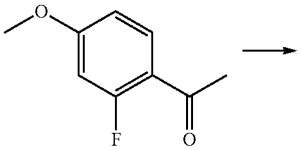

1-6

-continued

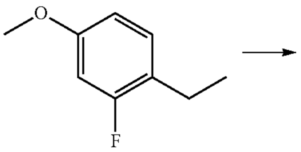

1-7

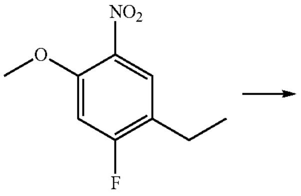

1-8

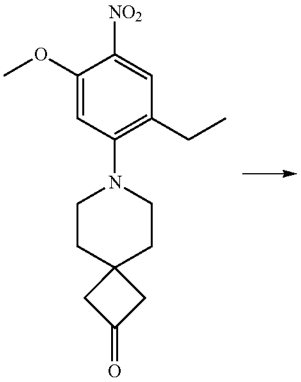

1-9

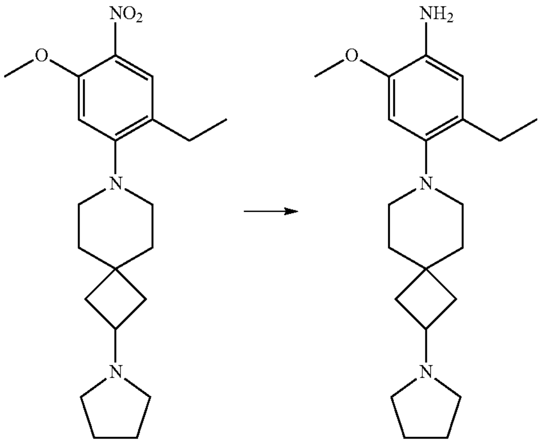

37-1 37-2

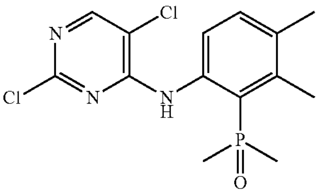

+

1-5

-continued

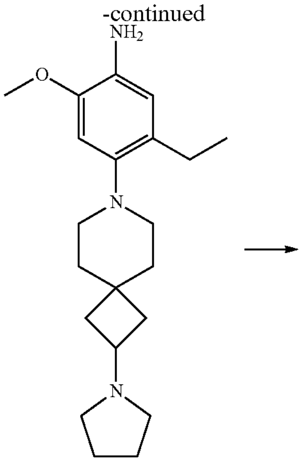

37-2

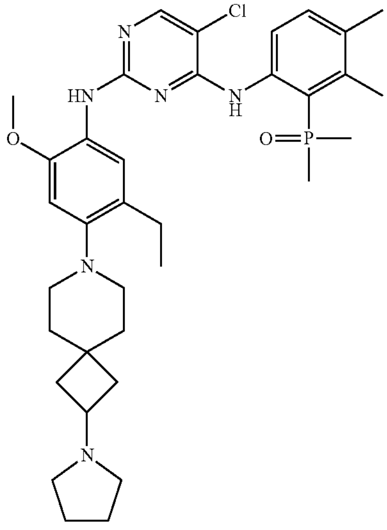

Step 1. 2-Iodo-3,4-dimethyl-1-nitrobenzene (1-2)

2,3-Dimethyl-6-nitroaniline (2 g, 12 mmol) was dissolved in HCl (10 mL). At 0° C., a water (5 mL) solution of $NaNO_2$ (1 g, 14.5 mmol) was slowly added. Stirring was conducted for 1 hour. A water (10 mL) solution of KI (3 g, 18 mmol) was added. Natural temperature returning and stirring were conducted for 1 hour. After the reaction was completed, water (20 ml) was added to the reaction solution. Extraction was conducted with EA (ethyl acetate, 3×20 ml). The organic phase was washed with sodium thiosulfate (3×20 ml) and a saturated salt solution (3×20 ml), dried with anhydrous sodium sulfate, and purified with column chromatography (PE:EA=6:1) to obtain the product as a yellow solid (1-2).

Step 2. (2,3-Dimethyl-6-nitrophenyl)dimethylphosphine oxide (1-3)

The intermediate 1-2 (3.0 g, 10.8 mmol) was dissolved in dioxane (20 mL). Dimethylphosphine oxide (1.27 g, 16.2 mmol), $K_3PO_4$ (4.60 g, 21.6 mmol), $Pd(OAC)_2$ (242 mg, 1.1 mmol), and Xantphos (4,5-bis(diphenylphosphino)-9,9-dimethylxanthene, 1.25 g, 2.2 mmol) were added in sequence. Nitrogen displacement was conducted three times. Reflux stirring was conducted for 12 hours. After the reaction was completed, water (50 ml) was added to the reaction solution. Extraction was conducted with dichloromethane (3×50 ml). The organic phase was washed with a saturated salt solution (3×30 ml), dried with anhydrous sodium sulfate, and purified with silica gel column chromatography using DCM: MeOH (15:1) as an eluent to obtain a brown solid (1-3); ESI-MS: m/z=228 $[M+H]^+$.

Step 3. (2,3-Dimethyl-6-aminophenyl)dimethylphosphine oxide (1-4)

The intermediate 1-3 (2.0 g) was dissolved in methanol (30 ml). 10% Palladium on carbon (55% water) (500 mg) was added. $H_2$ was introduced for displacement three times. Stirring was conducted at 40° C. for 2 hours. After the reaction was completed, suction filtration was conducted to collect the organic phase, which was subjected to rotary evaporation to remove the solvent to obtain a product (1-4); ESI-MS: m/z=198 $[M+H]^+$.

Step 4. (6-((2,5-Dichloropyrimidin-4-yl)amino)-2,3-dimethylphenyl)dimethylphosphine oxide (1-5)

The intermediate 1-4 (1 g, 5 mmol) was dissolved in DMF (20 ml). 2,4,5-Trichloropyrimidine (1.4 g, 7.7 mmol) and $K_2CO_3$ (1.4 g, 10 mmol) were added in sequence. Heating was conducted to 100° C., and stirring was conducted for 12 hours. After the reaction was completed, water (50 ml) was added to the reaction solution. Extraction was conducted with dichloromethane (3×50 ml). Washing was conducted with a saturated salt solution, drying was conducted with anhydrous sodium sulfate, and purification was conducted with silica gel column chromatography using DCM:MeOH (15:1) as an eluent to obtain a yellow solid (1-5); ESI-MS: m/z=344 $[M+H]^+$.

Step 5. 1-Ethyl-2-fluoro-4-methoxybenzene (1-7)

Triethylsilane (2 g, 18 mmol) was dissolved in DCM. A boron trifluoride ether solution was slowly added under an ice bath until white smoke appears at the bottle mouth. 1-(2-Fluoro-4-methoxyphenyl)ethan-1-one (1-6) (1 g, 6 mmol) was dissolve in DCM (dichloromethane), and dropwise added into the above reaction solution at a constant pressure. After dropwise adding was completed, the reaction solution was transferred to a room temperature for reaction for 20 minutes. The reaction process was detected with TLC. After the reaction was completed, the reaction solution was transferred to an ice bath, a saturated salt solution was added for quenching, extraction was conducted with DCM, and the solvent was removed to obtain a white solid (1-7).

Step 6. 1-Ethyl-2-fluoro-4-methoxy-5-nitrobenzene (1-8)

The intermediate 1-7 (1 g, 6.5 mmol) was dissolved in DCM. Concentrated nitric acid (5 ml) was slowly added under an ice bath. After dropwise adding was completed, the reaction solution was transferred to a room temperature for reaction for 2 hours. The reaction process was detected with LCMS. After the reaction was completed, saturated $NaHCO_3$ was added for neutralization. Extraction was conducted with DCM, drying was conducted with anhydrous sodium sulfate, and purification was conducted with silica gel column chromatography using PE:EA=6:1 as an eluent to obtain a yellow solid (1-8). ESI-MS: m/z=200 $[M+H]^+$.

Step 7. 7-(2-Ethyl-5-methoxy-4-nitrophenyl)-7-azaspiro[3.5]nonan-2-one (1-9)

The intermediate 1-8 (400 mg, 2 mmol) was dissolved in DMSO (10 ml). 7-Azaspiro[3.5]nonan-2-one (350 mg, 2.5 mmol) and $K_2CO_3$ (830 mg, 6 mmol) were added in sequence. Heating was conducted to 120° C. for reaction for 12 hours. The reaction process was detected with LC-MS. After the reaction was completed, concentrated nitric acid (5 ml) was slowly added under an ice bath. After dropwise adding was completed, the reaction solution was transferred to a room temperature for reaction for 2 hours. The reaction process was detected with LC-MS. After the reaction was completed, water (30 ml) was added. Extraction was conducted with ethyl acetate (3×30 ml), washing was conducted with a saturated salt solution, drying was conducted with anhydrous sodium sulfate, and purification was conducted with silica gel column chromatography using PE:EA=1:1 as an eluent to obtain a yellow solid (1-9). ESI-MS: m/z=319 $[M+H]^+$.

Step 8. 7-(2-Ethyl-5-methoxy-4-nitrophenyl)-2-(pyrrol-1-yl)-7-azaspiro[3.5]nonane (37-1)

The intermediate 1-9 (320 mg, 1 mmol) was dissolved in DCM (10 ml). Pyrrolidine (2.5 mmol) and glacial acetic acid (200 μL) were added in sequence. Heating was conducted to 40° C. for reaction for 1 hour. The reaction solution was then transferred to a room temperature. Sodium triacetoxyborohydride (616 mg, 3 mmol) was added. Stirring was conducted for 1 hour. The reaction process was detected with LC-MS. After the reaction was completed, saturated $NaHCO_3$ was added for neutralization. Extraction was conducted with DCM. Washing was conducted with a saturated salt solution, drying was conducted with anhydrous sodium sulfate, and separation and purification were conducted with silica gel column chromatography using DCM:MeOH=30:1 as an eluent to obtain a light yellow solid (37-1). ESI-MS: m/z=374 $[M+H]^+$.

Step 9. 5-Ethyl-2-methoxy-4-(2-(pyrrol-1-yl)-7-azaspiro[3.5]nonanyl-7-yl)aniline (37-2)

The intermediate 37-1 (373 mg, 1 mmol) was dissolved in methanol (10 ml). 10% Palladium on carbon (55% water) (35 mg) was added. $H_2$ was introduced for displacement three times. Stirring was conducted at 40° C. for 2 hours. After the reaction was completed, suction filtration was conducted to collect the organic phase, which was subjected to rotary evaporation to remove the solvent to obtain a product (37-2); ESI-MS: m/z=344 $[M+H]^+$.

Step 10. (6-((5-Chloro-2-((5-ethyl-2-methoxy-4-(2-(pyrrolidin-1-yl)-7-azaspiro[3.5]nonan-7-yl)phenyl)amino)pyrimidin-4-yl)amino)-2,3-dimethylphenyl)dimethylphosphine oxide (compound 48)

Dioxane (20 mL) was added to a mixture of the intermediate 1-5 (380 mg, 1.1 mmol), the intermediate 37-2 (343 mg, 1 mmol), palladium acetate (23 mg, 0.1 mmol), 1.1'-binaphthyl-2.2'-diphenyl phosphine (63 mg, 0.1 mmol), and cesium carbonate (1 mg, 3 mmol). Nitrogen displacement was conducted three times. Reflux stirring was conducted overnight. The solvent was recovered under reduced pressure to obtain a residue. The residue was purified with silica gel column chromatography using DCM:MeOH (25:1) as an eluent to obtain a crude product, which was purified with a silica gel preparation plate using DCM MeOH (30:1) as a developing solvent to obtain a white solid; ESI-MS: m/z=651 $[M+H]^+$. $^1H$ NMR (400 MHz, Chloroform-d) δ 11.74 (s, 1H), 8.16 (s, 1H), 8.04 (s, 2H), 7.32 (s, 1H), 6.59 (s, 1H), 3.82 (s, 3H), 3.39 (s, 1H), 3.09 (s, 2H), 2.72 (d, J=18.4 Hz, 4H), 2.53 (d, J=10.4 Hz, 2H), 2.41 (s, 2H), 2.29 (d, J=18.1 Hz, 6H), 2.22 (s, 2H), 2.08 (s, 6H), 1.97 (d, J=13.0 Hz, 6H), 1.89 (s, 2H), 1.73 (s, 2H), 1.00 (s, 3H).

Preparative Embodiment 38. 1-(7-(4-((5-chloro-4-((2-(dimethylphosphoryl)-3,4-dimethylphenyl)amino)pyrimidin-2-yl)amino)-2-ethyl-5-methoxyphenyl)-7-azaspiro[3.5]nonan-2-yl)azetidine-3-carbonitrile (compound 49)

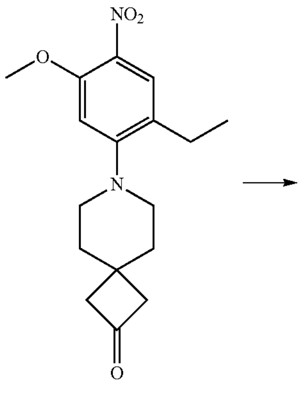

1-9

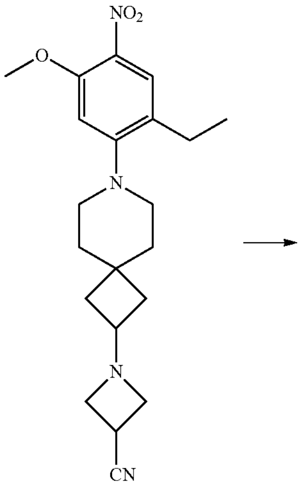

38-1

-continued

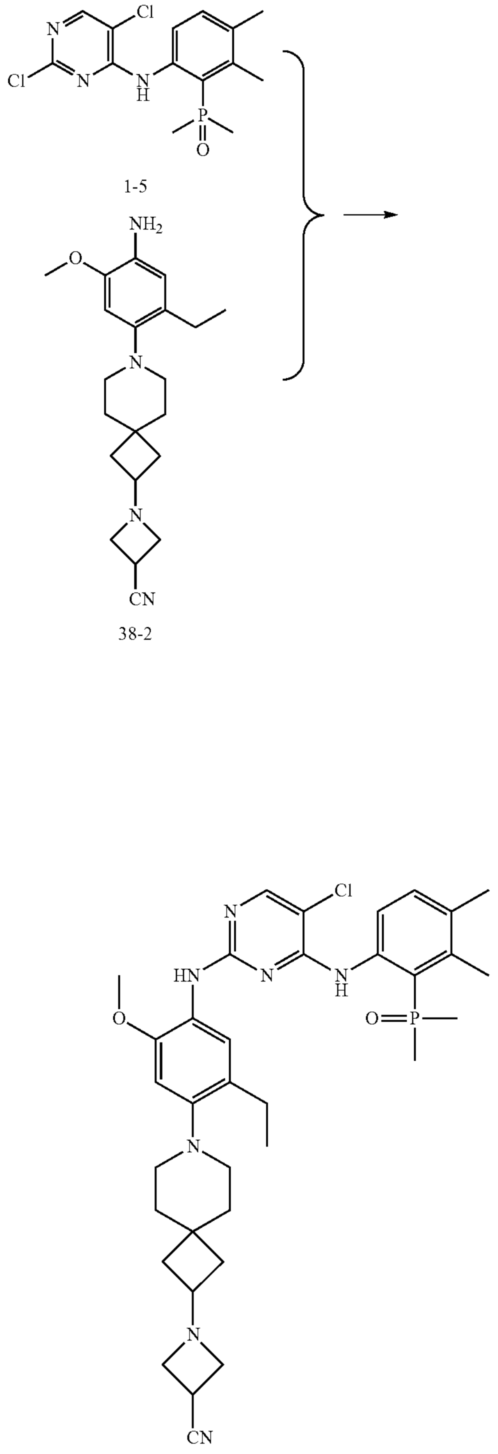

1-5

38-2

Referring to Preparative Embodiment 37, compound 49 was prepared by replacing pyrrolidine with 3-acetonitrile cyclobutylamine; ESI-MS: m/z=662 $[M+H]^+$. $^1H$ NMR (400 MHz, Chloroform-d) δ 11.75 (s, 1H), 8.17 (s, 1H), 8.04 (s, 2H), 7.32 (s, 2H), 6.61 (s, 1H), 3.82 (s, 3H), 3.53 (s, 2H), 3.26 (s, 3H), 3.11 (s, 1H), 2.70 (d, J=18.1 Hz, 4H), 2.53 (s, 2H), 2.28 (d, J=17.7 Hz, 6H), 1.96 (d, J=12.9 Hz, 8H), 1.69 (s, 4H), 1.65-1.53 (m, 2H), 1.01 (s, 3H).

Preparative Embodiment 39. (2-((5-chloro-2-((5-ethyl-2-methoxy-4-(4-((3S,5R)-3,4,5-trimethylpiperazine-1-yl)piperidin-1-yl)phenyl)amino)pyrimidin-4-yl)amino)-4,5-dimethylphenyl)dimethylphosphine oxide (compound 50)

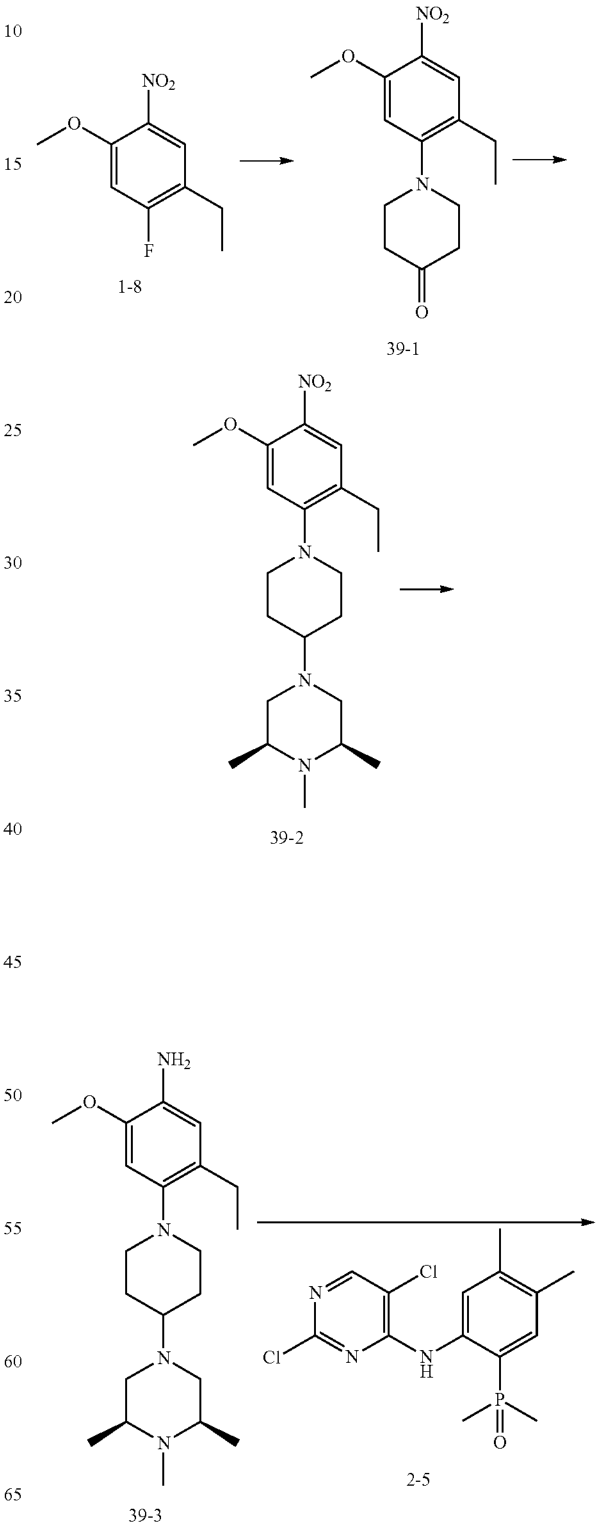

1-8

39-1

39-2

39-3

2-5

-continued

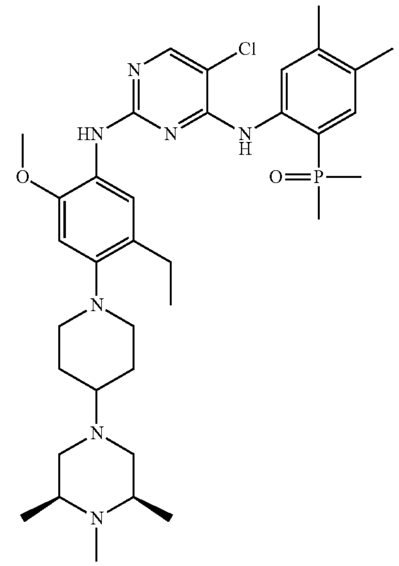

Referring to Preparative Embodiment 37, compound 50 was prepared by replacing pyrrolidine with (3S,5R)-3,4,5-trimethylpiperazine; ESI-MS: m/z=668 $[M+H]^+$. $^1H$ NMR (400 MHz, Chloroform-d) δ 10.37 (s, 1H), 8.24 (s, 1H), 8.06 (s, 1H), 8.00 (s, 1H), 7.01 (d, J=14.0 Hz, 1H), 6.64 (s, 1H), 3.84 (s, 3H), 2.95 (dd, J=75.9, 11.1 Hz, 4H), 2.65 (d, J=11.6 Hz, 2H), 2.48 (d, J=12.9 Hz, 2H), 2.29 (s, 4H), 2.22 (d, J=28.0 Hz, 6H), 2.13 (d, J=10.9 Hz, 2H), 1.92 (d, J=12.5 Hz, 4H), 1.79 (d, J=13.1 Hz, 6H), 1.68 (d, J=11.7 Hz, 2H), 1.12 (s, 6H), 0.96 (s, 3H).

Preparative Embodiment 40. (6-((5-chloro-2-((5-ethyl-2-methoxy-4-(4-((1R,5S)-8-methyl-3,8-diazabicyclo[3.2.1]octan-3-yl)piperidin-1-yl)phenyl)amino)pyrimidin-4-yl)amino)-2,3-dimethylphenyl)dimethylphosphine oxide (compound 51)

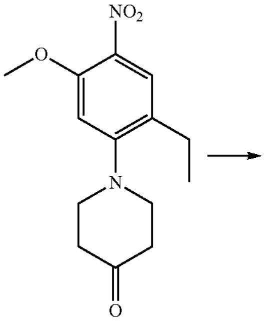

39-1

-continued

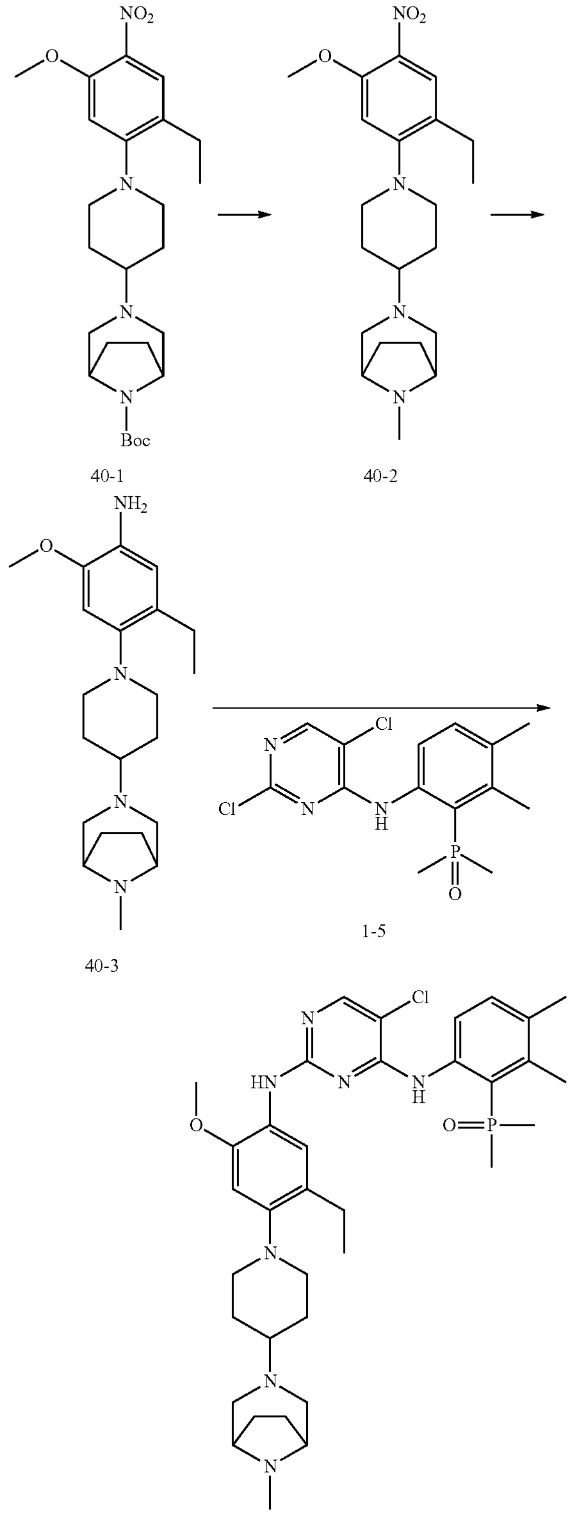

40-1

40-2

40-3

1-5

Referring to Preparative Embodiment 37, compound 51 was prepared by replacing pyrrolidine with 8-BOC-3,8-diazabicyclo[3.2.1]octane; ESI-MS: m/z=666 $[M+H]^+$. $^1H$ NMR (400 MHz, Chloroform-d) δ 11.75 (s, 1H), 8.16 (s, 1H), 8.05 (s, 2H), 7.32 (s, 2H), 6.62 (s, 1H), 3.82 (s, 3H), 3.03 (d, J=11.3 Hz, 4H), 2.74 (d, J=11.2 Hz, 2H), 2.68-2.48 (m, 8H), 2.38 (s, 1H), 2.29 (d, J=17.0 Hz, 6H), 2.03 (s, 5H), 1.97 (d, J=13.0 Hz, 6H), 1.86 (d, J=11.9 Hz, 2H), 1.65 (q, J=11.8 Hz, 2H), 1.00 (s, 3H).

Preparative Embodiment 41. (6-((5-Chloro-2-((5-ethyl-2-methoxy-4-(4-((3aR,6aS)-5-methyloctahydropyrrol[3,4-C]pyrrol-2(1H)-yl)piperidin-1-yl)phenyl)amino)pyrimidin-4-yl)amino)-2,3-dimethylphenyl)dimethylphosphine oxide (compound 52)

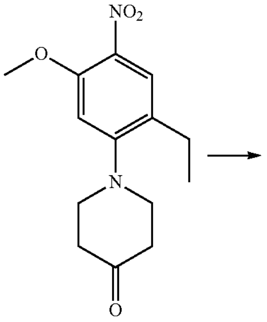

39-1

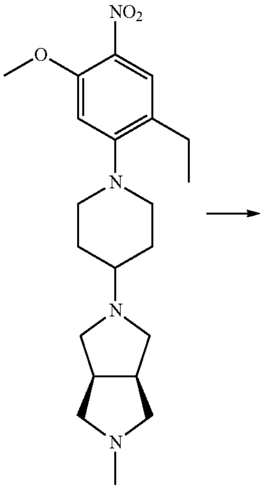

41-1

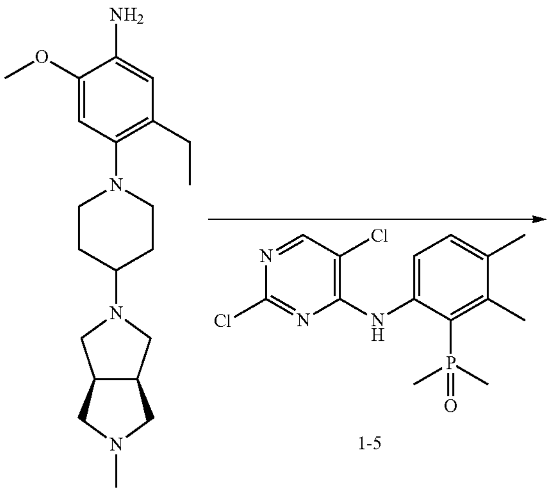

1-5

41-2

-continued

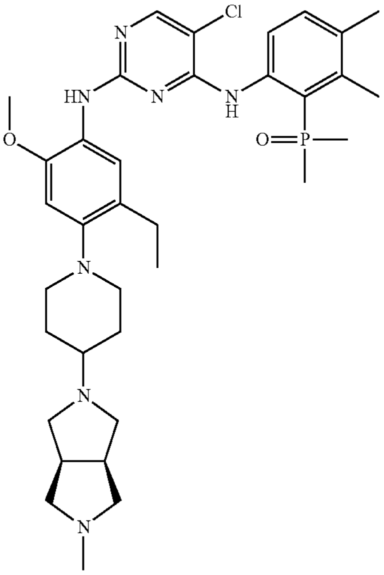 [SMILES: CCc1cc(Nc2ncc(Cl)c(Nc3ccc(C)c(C)c3P(C)(C)=O)n2)c(OC)cc1N1CCC(N2C[C@H]3CN(C)C[C@H]3C2)CC1]

Referring to Preparative Embodiment 37, compound 52 was prepared by replacing pyrrolidine with 2-methyl-octahydropyrrol[3,4-C]pyrrole; ESI-MS: m/z=666 $[M+H]^+$. $^1H$ NMR (400 MHz, Chloroform-d) δ 11.74 (s, 1H), 8.26-8.12 (m, 1H), 8.04 (s, 2H), 7.32 (s, 1H), 7.29 (s, 1H), 6.64 (s, 1H), 3.83 (s, 3H), 3.08-2.90 (m, 4H), 2.75 (s, 2H), 2.64 (t, J=11.9 Hz, 2H), 2.49 (s, 4H), 2.31 (s, 6H), 2.27 (s, 3H), 2.12 (t, J=11.0 Hz, 1H), 1.97 (d, J=12.6 Hz, 8H), 1.68 (s, 2H), 1.00 (s, 3H).

Preparative Embodiment 42. (6-((5-Chloro-2-((5-ethyl-2-methoxy-4-(4-(6-methyl-3,6-diazadicyclo [3.1.1]heptane-3-yl)piperidin-1-yl)phenyl)amino) pyrimidin-4-yl)amino)-2,3-dimethylphenyl) dimethylphosphine oxide (compound 53)

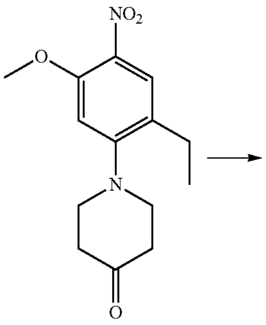

39-1

-continued
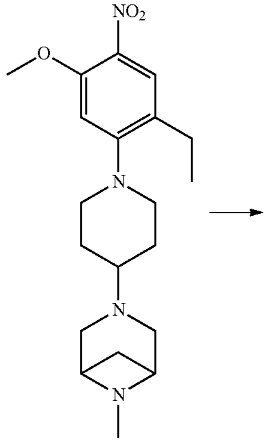
42-1
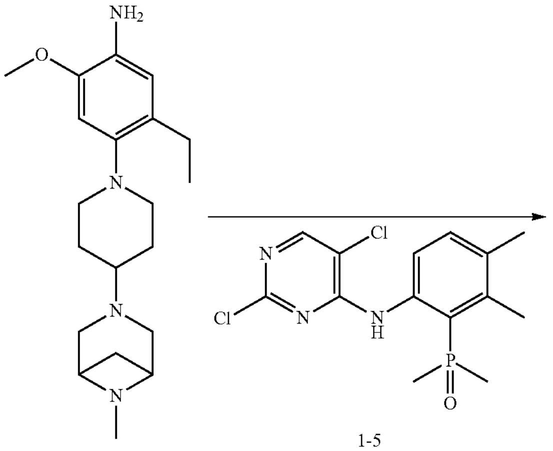
1-5
42-2
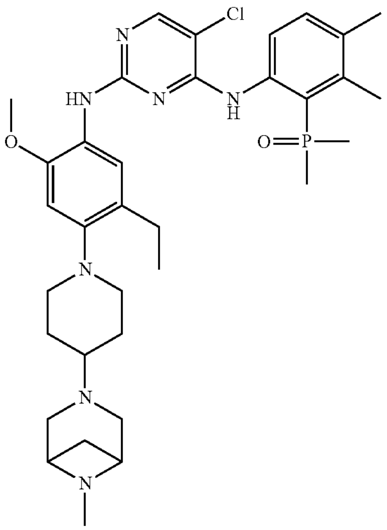 [SMILES: CCc1cc(Nc2ncc(Cl)c(Nc3ccc(C)c(C)c3P(C)(C)=O)n2)c(OC)cc1N1CCC(N2CC3CC(C2)N3C)CC1]
Referring to Preparative Embodiment 37, compound 53 was prepared by replacing pyrrolidine with 6-methyl-3,6-diazadicyclo[3.1.1]heptane; ESI-MS: m/z=652 $[M+H]^+$.
Preparative Embodiment 43. (6-((5-Chloro-2-((5-ethyl-2-methoxy-4-(4-(5-methyl-2,5-diazadicyclo[2.2.1]heptane-2-yl)piperidin-1-yl)phenyl)amino)pyrimidin-4-yl)amino)-2,3-dimethylphenyl)dimethylphosphine oxide (compound 54)
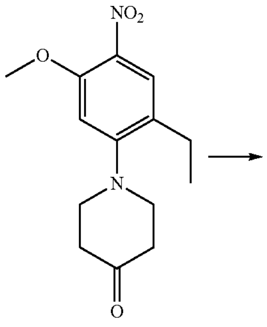
39-1
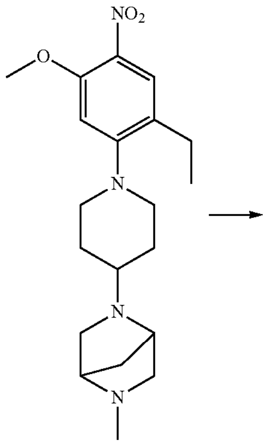
43-1
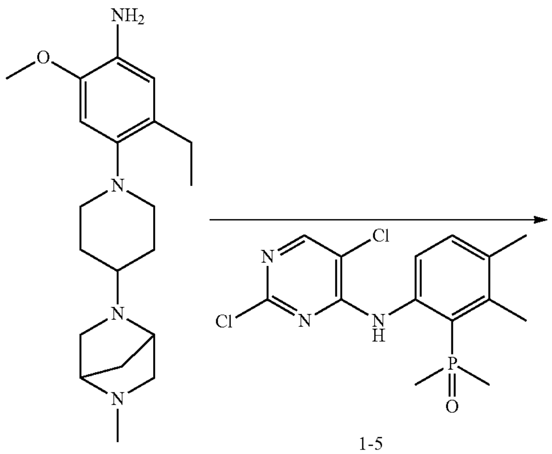
1-5
43-2

-continued

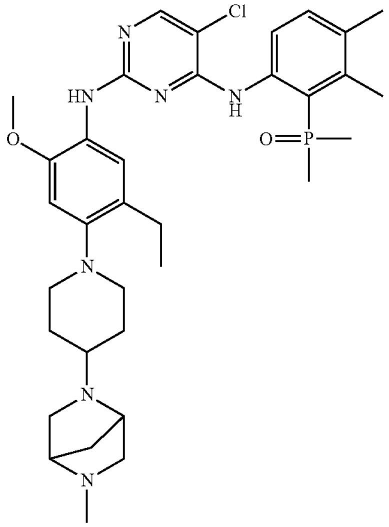 [SMILES: CCc1cc(Nc2ncc(Cl)c(Nc3ccc(C)c(C)c3P(C)(C)=O)n2)c(OC)cc1N1CCC(N2CC3CC2CN3C)CC1]

Referring to Preparative Embodiment 37, compound 54 was prepared by replacing pyrrolidine with 2-methyl-2,5-diazadicyclo[2.2.1]heptane; ESI-MS: m/z=652 $[M+H]^+$. $^1H$ NMR (400 MHz, DMSO-$d_6$) δ 11.91 (s, 1H), 7.96 (dd, J=8.7, 4.0 Hz, 1H), 7.86 (s, 1H), 7.48 (s, 1H), 7.16 (d, J=8.5 Hz, 1H), 6.75 (s, 1H), 3.76 (s, 3H), 2.96-2.88 (m, 2H), 2.81 (dt, J=13.8, 6.8 Hz, 2H), 2.69 (dt, J=12.6, 9.3 Hz, 2H), 2.54 (s, 1H), 2.46 (t, J=7.5 Hz, 4H), 2.32 (s, 3H), 2.29 (s, 3H), 2.20 (s, 3H), 1.87 (d, J=13.2 Hz, 6H), 1.80 (d, J=21.1 Hz, 4H), 1.68 (d, J=9.2 Hz, 1H), 1.57 (d, J=9.2 Hz, 1H), 1.54-1.43 (m, 2H), 1.00 (t, J=7.5 Hz, 3H).

Preparative Embodiment 44. (6-((5-Chloro-2-((5-ethyl-2-methoxy-4-(9-methyl-3,9-diazaspiro[5.5]undecan-3-yl)phenyl)amino)pyrimidin-4-yl)amino)-2,3-dimethylphenyl)dimethylphosphine oxide (compound 55)

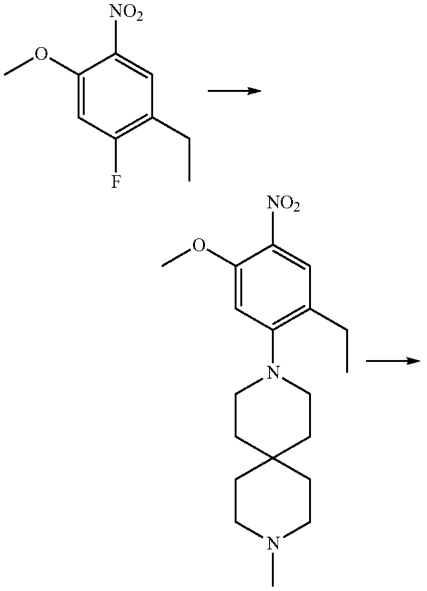

44-1

-continued

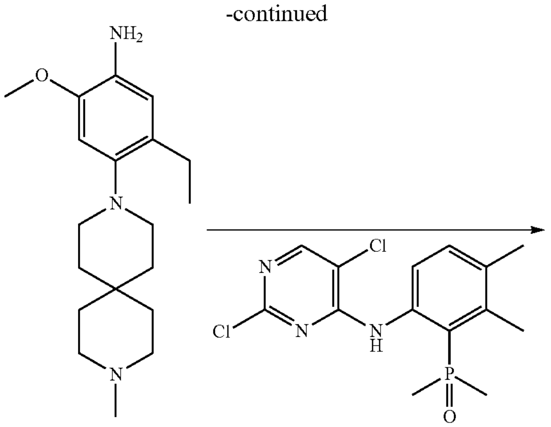

44-2

1-5

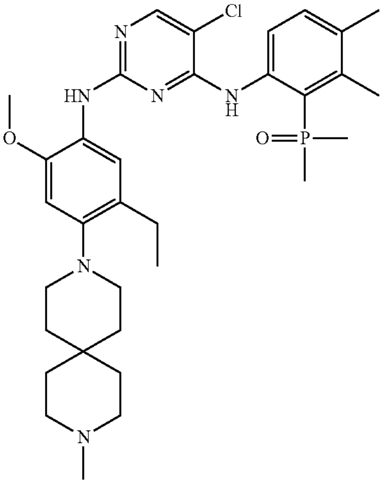

Referring to Preparative Embodiment 37, compound 55 was prepared by replacing 4-piperidone with 3-methyl-3,9-diazaspiro[5.5]undecane; ESI-MS: m/z=625 $[M+H]^+$. $^1H$ NMR (400 MHz, Chloroform-d) δ 11.77 (s, 1H), 8.17 (dd, J=8.5, 4.2 Hz, 1H), 8.05 (d, J=9.8 Hz, 2H), 7.30 (d, J=14.7 Hz, 2H), 6.65 (s, 1H), 3.83 (s, 3H), 2.78 (t, J=5.4 Hz, 4H), 2.62-2.50 (m, 6H), 2.40 (s, 3H), 2.31 (s, 3H), 2.26 (s, 3H), 1.97 (d, J=12.9 Hz, 6H), 1.70 (dq, J=5.8, 2.7 Hz, 4H), 1.64 (d, J=5.6 Hz, 4H), 1.02 (t, J=7.5 Hz, 3H).

Comparative Compound A

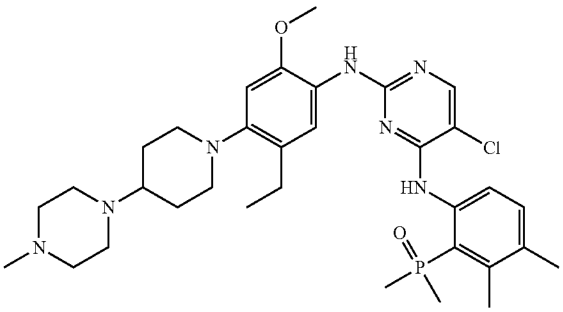

Comparative Compound A was prepared according to the method described in Embodiment 6 of WO2021018003A1. ESI-MS: m/z=640 $[M+H]^+$. $^1H$ NMR (400 MHz, Chloroform-d) δ 12.18 (s, 1H), 8.11 (s, 1H), 8.02 (s, 1H), 7.96 (s, 1H), 7.90 (s, 1H), 7.22 (s, 1H), 6.60 (s, 1H), 3.82 (s, 3H), 3.34 (s, 8H), 2.90 (s, 2H), 2.73 (s, 3H), 2.69 (s, 2H), 2.50 (s, 2H), 2.29 (d, J=18.7 Hz, 6H), 2.13 (d, J=11.7 Hz, 2H), 1.97 (d, J=13.1 Hz, 6H), 1.89 (d, J=11.6 Hz, 2H), 0.99 (s, 3H).

Comparative Compound B

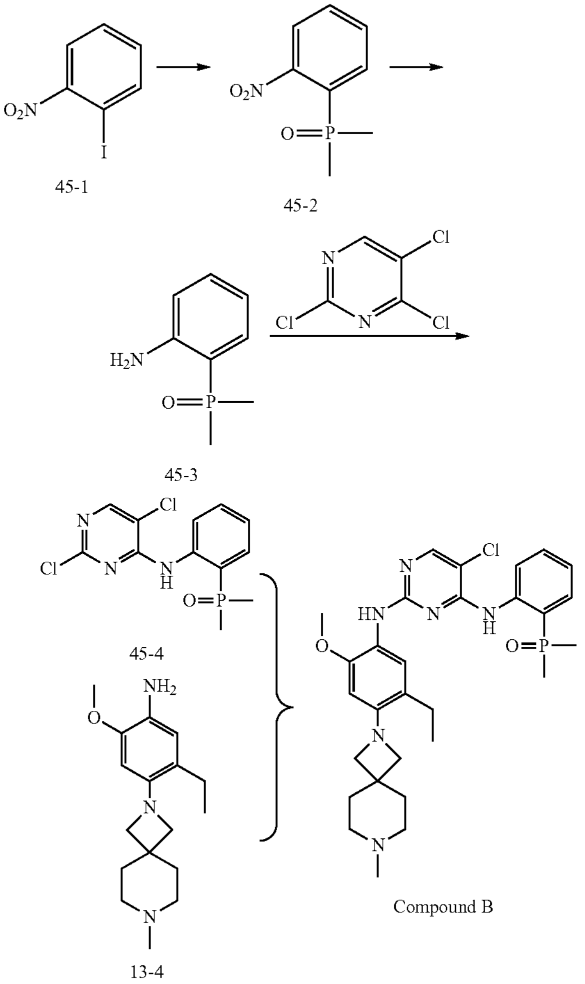

45-1 45-2 45-3 45-4 13-4 Compound B

Step 1. dimethyl (2-nitrophenyl)phosphine Oxide (45-2)

2-Nitroiodobenzene (2.69 g, 10.8 mmol) was dissolved in dioxane (20 mL). Dimethylphosphine oxide (1.27 g, 16.2 mmol), $K_3PO_4$ (4.60 g, 21.6 mmol), Pd(OAC) 2 (242 mg, 1.1 mmol), and Xantphos (4,5-bis(diphenylphosphino)-9,9-dimethylxanthene, 1.25 g, 2.2 mmol) were added in sequence. Nitrogen displacement was conducted three times. Reflux stirring was conducted for 12 hours. After the reaction was completed, water (50 ml) was added to the reaction solution. Extraction was conducted with dichloromethane (3×50 ml). The organic phase was washed with a saturated salt solution (3×30 ml), dried with anhydrous sodium sulfate, and purified with silica gel column chromatography using DCM:MeOH (15:1) as an eluent to obtain a brown solid (45-2); ESI-MS: m/z=200 $[M+H]^+$.

Step 2. (2-Aminophenyl)dimethylphosphine Oxide (45-3)

The intermediate 45-2 (2.0 g) was dissolved in methanol (30 ml). 10% Palladium on carbon (55% water) (500 mg) was added. $H_2$ was introduced for displacement three times. Stirring was conducted at 40° C. for 2 hours. After the reaction was completed, suction filtration was conducted to collect the organic phase, which was subjected to rotary evaporation to remove the solvent to obtain a product (45-3); ESI-MS: m/z=170 $[M+H]^+$.

Step 3. (2-((2,5-dichloropyrimidin-4-yl)amino)phenyl)dimethylphosphine Oxide (45-4)

The intermediate 45-3 (0.85 g, 5 mmol) was dissolved in DMF (20 ml). 2,4,5-Trichloropyrimidine (1.4 g, 7.7 mmol) and $K_2CO_3$ (1.4 g, 10 mmol) were added in sequence. Heating was conducted to 100° C., and stirring was conducted for 12 hours. After the reaction was completed, water (50 ml) was added to the reaction solution. Extraction was conducted with dichloromethane (3×50 ml). Washing was conducted with a saturated salt solution, drying was conducted with anhydrous sodium sulfate, and purification was conducted with silica gel column chromatography using DCM:MeOH (15:1) as an eluent to obtain a yellow solid (45-4); ESI-MS: m/z=316 $[M+H]^+$.

Step 4. (2-((5-Chloro-2-((5-ethyl-2-methoxy-4-(7-methyl-2,7-diazaspiro[3.5]nonan-2-yl)phenyl)amino) pyrimidin-4-yl)amino)phenyl)dimethylphosphine oxide (compound B)

Dioxane (20 mL) was added to a mixture of the intermediate 45-4 (348 mg, 1.1 mmol), the intermediate 13-4 (289 mg, 1 mmol), palladium acetate (23 mg, 0.1 mmol), 1.1'-binaphthyl-2.2'-diphenyl phosphine (63 mg, 0.1 mmol), and cesium carbonate (1 mg, 3 mmol). Nitrogen displacement was conducted three times. Reflux stirring was conducted overnight. The solvent was recovered under reduced pressure to obtain a residue. The residue was purified with silica gel column chromatography using DCM:MeOH (25:1) as an eluent to obtain a crude product, which was purified with a silica gel preparation plate using DCM MeOH (30:1) as a developing solvent to obtain a white solid; ESI-MS: m/z=569 $[M+H]^+$. $^1H$ NMR (400 MHz, Chloroform-d) δ 10.75 (s, 1H), 8.63-8.57 (m, 1H), 8.06 (s, 1H), 7.82 (s, 1H), 7.43 (ddt, J=8.7, 7.3, 1.4 Hz, 1H), 7.27 (dd, J=7.7, 1.6 Hz, 1H), 7.12-7.04 (m, 2H), 6.08 (s, 1H), 3.83 (s, 3H), 3.64 (s, 4H), 2.60 (s, 4H), 2.49-2.41 (m, 5H), 2.05-1.98 (m, 4H), 1.82 (d, J=13.1 Hz, 6H), 1.05 (t, J=7.5 Hz, 3H).

BIOLOGICAL EXPERIMENT

Embodiment 1

$EGFRL^{858R/T790M/C797S}$ kinase inhibitory activity experiment: The compounds of the present invention have excellent in-vitro inhibitory activity against $EGFR^{L858R/T790M/C797S}$ kinase Experimental Materials

| Name of reagent | Supplier | Article number | Batch number |
|---|---|---|---|
| $EGFR^{L858R/T790M/C797S}$ | Invitrogen | A33556 | 2030210 |
| Kinase substrate22 | GL | 112393 | P200403-CL112393 |
| DMSO | Sigma | D8418-1L | SHBG3288V |
| 384-well plate | Corning | 3573 | 12619003 |
| EAI045 | selleckchem | S8242 | S824201 |

Centrifuge (manufacturer: Eppendorf, model: 5430)

Microplate reader (manufacturer: Perkin Elmer, model: Caliper EZ ReaderII)

Echo 550 (manufacturer: Labcyte, model: Echo 550)

Experimental Method

Compound preparation:

A 10 mM storage solution was prepared.

Kinase Reaction Process (1) 1× Kinase buffer was prepared.

(2) Preparation of concentration gradient of compound: The tested compound has a test concentration starting from 1 μM, diluted 10 times, with 10 concentrations, and subjected to single-well or multi-well detection. The compound was diluted to a 100% DMSO solution with a final concentration of 100 times in a 384 source plate. 250 μL of the compound at a final concentration of 100 times was transferred to the target plate 384-well-plate using the pipette Echo 550.

(3) A kinase solution with a final concentration of 2.5 times was prepared using 1× Kinase buffer.

(4) 10 μL of the kinase solution with the final concentration of 2.5 times was added to a compound well and a positive control well, respectively; 10 μL of 1×Kinase buffer was added to a negative control well.

(5) Centrifugation was conducted at 1000 rpm for 30 seconds, and the reaction plate was shaken and mixed well, and incubated at a room temperature for 10 minutes.

(6) A mixed solution of ATP with a final concentration of 5/3 times and Kinase substrate 22 was prepared using 1×Kinase buffer.

(7) A mixed solution of 15 μL of ATP with a final concentration of 5/3 times and a substrate was added for initial reaction.

(8) The 384-well-plate was centrifuged at 1000 rpm for 30 seconds, shaken and mixed well, and incubated at a room temperature for 60 minutes.

(9) 30 μL of a termination detection solution was added to stop the kinase reaction. Centrifugation was conducted at 1000 rpm for 30 seconds. Shaking and mixing well were conducted.

(10) The conversion rate was read using Caliper EZ Reader.

Data Analysis

Calculation formula:

$$\%\,\text{Inhibition} = \frac{\text{Conversion\%\_max} - \text{Conversion\%\_sample}}{\text{Conversion\%\_max} - \text{Conversion\%\_min}} \times 100$$

where Conversion %_sample is the conversion rate reading of the sample; Conversion %_min: the average value of negative control wells, representing the conversion rate reading of wells without enzyme activity; Conversion %_max: the average value of positive control wells, representing the conversion rate reading of wells without compound inhibition; % Inhibition represents the inhibition rate.

Fitting of Dose-Response Curve

Using the log value of concentration as the X-axis and the percentage inhibition rate as the Y-axis, the dose-response curve was fitted using the log(inhibitor) vs. response—Variable slope of the analysis software GraphPad Prism 5 to obtain the $IC_{50}$ value of each compound on enzyme activity.

TABLE 1

In-vitro inhibitory activity of compounds of the present invention against EGFR L858R/T790M/C797S kinase

| Compound No. | $EGFR^{L858R/T790M/C797S}$ ($IC_{50}$ NM) | Compound No. | $EGFR^{L858R/T790M/C797S}$ ($IC_{50}$ NM) |
|---|---|---|---|
| 1 | 27 | 16 | 12 |
| 2 | 89 | 17 | 0.77 |
| 3 | 21 | 18 | 36 |
| 4 | 16 | 19 | 0.86 |
| 5 | 11 | 20 | 29 |
| 6 | 0.88 | 21 | 0.65 |
| 7 | 0.98 | 22 | 10 |
| 8 | 29 | 23 | 0.78 |
| 9 | 7.0 | 24 | 0.55 |
| 10 | 13 | 25 | 0.67 |
| 11 | 5.0 | 26 | 0.74 |
| 12 | 5.3 | 27 | 0.81 |
| 13 | 0.89 | 28 | 0.99 |
| 14 | 8.3 | 29 | 18.15 |
| 15 | 3.8 | 30 | 6.78 |
| 31 | 4.19 | 32 | 0.92 |
| 33 | 0.73 | 34 | 0.84 |
| 35 | 0.68 | 36 | 0.96 |
| 37 | 0.49 | 38 | 0.59 |
| 39 | 12.11 | 40 | 0.85 |
| 41 | 0.89 | 42 | 0.76 |
| 43 | 25.16 | 44 | 0.48 |
| 45 | 0.74 | 46 | 0.63 |

TABLE 1-continued

| In-vitro inhibitory activity of compounds of the present invention against EGFR L858R/T790M/C797S kinase | | | |
|---|---|---|---|
| Compound No. | $EGFR^{L858R/T790M/C797S}$ ($IC_{50}$ NM) | Compound No. | $EGFR^{L858R/T790M/C797S}$ ($IC_{50}$ NM) |
| 47 | 0.78 | 48 | 0.06293 |
| 49 | 8.226 | 50 | 0.07073 |
| 51 | 0.0452 | 52 | 0.03691 |
| 53 | 0.2686 | 54 | 0.2009 |
| 55 | 0.2969 | Comparative Compound A | 0.54 |
| Comparative Compound B | 2.3 | BD-2 | 5 |

It can be seen from Table 1 that the compounds of the present invention have excellent in-vitro inhibitory activity against $EGFR^{L858R/T790M/C797S}$ kinase.

Embodiment 2

BaF3 cell proliferation inhibition experiment: The compounds of the present invention have excellent inhibitory activity against the proliferation of $BaF3\text{-}EGFR^{L858R/T790M/C797S}$ cells (1) Cell Culture A. Cell line: BaF3 cells with stable overexpression of wild-type genes are named $BaF3\text{-}EGFR^{WT}$, and BaF3 cells with stable overexpression of $EGFR^{L858R/T790M/C797S}$ $EGFR^{del19/T790M/C797S}$ $EGFR^{L858R/C797S}$ and $EGFR^{del19/C797S}$ mutant genes are named $BaF3\text{-}EGFR^{L858R/T790M/C797S}$ $BaF3\text{-}EGFR^{del19/T790M/C797S}$ $BaF3\text{-}EGFR^{L858R/C797S}$ and $BaF3\text{-}EGFR^{del19/C797S}$ cells, respectively. Mediums:

RPMI 1640 and 10% FBS and 50 ng/mL EGF

B. Cell Thawing a) The medium was preheated in a 37° C. water bath.

b) The cryopreservation tube was taken from the liquid nitrogen tank, quickly placed in a 37° C. water bath, and melted completely within 1 minute.

c) The cell suspension was transferred to a 15 mL centrifuge tube containing a 10 mL medium and centrifuged at 1000 rpm for 4 minutes.

d) The supernatant was discarded, the cells were resuspended in a 1 mL medium and transferred to a 55 $cm^3$ culture dish containing a 10 mL medium, 20% serum and 50 ng/mL EGF were administered to the first-generation medium, and culture was conducted in a 37° C. and 5% $CO_2$ incubator.

C. Cell Passage a) The medium was preheated in a 37° C. water bath.

b) The cells in the culture dish were blown evenly with a 5 mL pipette, and 500 μL of the cells were pipetted out to be inoculated into a new 55 $cm^3$ culture dish and cultured in a 37° C. and 5% $CO_2$ incubator.

(2) Compound Preparation a) The compound to be tested (10 mM stock solution) was diluted with 100% DMSO to 1 mM, and diluted with a culture solution in a 24-well plate to prepare of a working solution of 2 μM concentration.

b) The 2 μM working solution was diluted with a triple dilution method to obtain working solutions with approximate concentrations of 2 μM, 600 nM, 200 nM, 60 nM, and 20 nM.

(3) Cell Culture Plate a) The cells at the logarithmic growth phase were centrifuged at 1000 rpm for 4 minutes, resuspended with a medium (containing 10% serum and 50 ng/mL EGF), and counted.

b) The cells were inoculated into a 96-well plate with a cell density of 4000 cells/well, and placed in a 37° C. and 5% $CO_2$ incubator for culture for 12 hours.

(4) Cell Administration a) The prepared compound was added to a 96-well plate, with 100 μL per well. The final concentrations were 1 μM, 300 nM, 100 nM, 30 nM, 10 nM, and 0 nM, and the final concentration of DMSO was 0.2%. A medium served as a blank control.

b) The cells were placed in 37° C. and 5% $CO_2$ incubator for culture for 72 hours.

(5) Cell Viability Testing a) The 96-well cell culture plate was taken out, and 20 μL of a CCK-8 reagent (Cell Counting Kit-8, Topscience, Catalog No. C0005) was added in the dark.

b) Mixing well was conducted on a horizontal shaking table at a room temperature at 100 rpm for 5 minutes.

c) The culture plate was placed in a 37° C. constant-temperature incubator for incubation.

d) Starting from the addition of the CCK-8, the absorbance at 450 nM was read using the TECAN microplate reader at 1 hour, 2 hours, and 3 hours, respectively.

(6) Data Analysis

The data was analyzed using GraphPad Prism 8.0 software to obtain a fitted curve of activity of the compounds. The $IC_{50}$ of the compounds was fitted from nonlinear regression equation.

Embodiment 3

A431 cell proliferation inhibition: The compounds of the present invention have good selectivity to wild-type EGFR (1) Cell Culture Cell line: A431.

A. Mediums

DMEM and 10% FBS

B. Cell Thawing a) The medium was preheated in a 37° C. water bath.

b) The cryopreservation tube was taken from the liquid nitrogen tank, quickly placed in a 37° C. water bath, and melted completely within 1 minute.

c) The cell suspension was transferred to a 15 mL centrifuge tube containing a 10 mL medium and centrifuged at 1000 rpm for 4 minutes.

d) The supernatant was discarded, the cells were resuspended in a 1 mL medium and transferred to a 55 $cm^3$ culture dish containing a 10 mL medium, 20% serum and 50 ng/mL EGF were administered to the first-generation medium, and culture was conducted in a 37° C. and 5% $CO_2$ incubator.

C. Cell Passage a) The medium was preheated in a 37° C. water bath.

b) The cells in the culture dish were blown evenly with a 5 mL pipette, and 500 μL of the cells were pipetted out to be inoculated into a new 55 $cm^3$ culture dish and cultured in a 37° C. and 5% $CO_2$ incubator.

(2) Compound Preparation a) The compound to be tested (10 mM stock solution) was diluted with 100% DMSO to 1 mM, and diluted with a culture solution in a 24-well plate to prepare of a working solution of 2 μM concentration.

b) The 2 μM working solution was diluted with a triple dilution method to obtain working solutions with approximate concentrations of 2 μM, 600 nM, 200 nM, 60 nM, and 20 nM.

(3) Cell Culture Plate a) The cells at the logarithmic growth phase were centrifuged at 1000 rpm for 4 minutes, resuspended with a medium (containing 10% serum and 50 ng/mL EGF), and counted.

b) The cells were inoculated into a 96-well plate with a cell density of 4000 cells/well, and placed in a 37° C. and 5% $CO_2$ incubator for culture for 12 hours.

(4) Cell Administration a) The prepared compound was added to a 96-well plate, with 100 μL per well. The final concentrations were 1 μM, 300 nM, 100 nM, 30 nM, 10 nM, and 0 nM, and the final concentration of DMSO was 0.2%. A medium served as a blank control.

b) The cells were placed in 37° C. and 5% $CO_2$ incubator for culture for 72 hours.

(5) Cell Viability Testing a) The cell supernatant was discarded, rinsed once with 1×PBS, and fixed with 10% trichloroacetic acid for 1 hour. The trichloroacetic acid was discarded, excess trichloroacetic acid was washed off with tap water, and the 96-well plate was dried in a 60° C. oven.

b) 70 μL of an SRB stain was added to each well of the dry 96-well plate for staining at a room temperature for 30 minutes. Excess SRB stain was washed off with 1% glacial acetic acid, and the 96-well plate was dried in a 60° C. oven.

c) SRB was dissolved with 100 μL of 10 mM Tris-base solution. The absorbance was detected at 540 nm ultraviolet absorption using the microplate reader. The data was analyzed.

(6) Data Analysis

The data was analyzed using GraphPad Prism 8.0 software to obtain a fitted curve of activity of the compounds. The $IC_{50}$ of the compounds was fitted from nonlinear regression equation.

TABLE 2

$IC_{50}$ of compounds on BaF3-$EGFR^{L858R/T790M/C797S}$ and A431

| Compound No. | BaF3-$EGFR^{L858R/T790M/C797S}$ ($IC_{50}$ NM) | A431 ($IC_{50}$ NM) |
|---|---|---|
| 5 | 42.32 | >500 |
| 6 | 67.60 | >1000 |
| 7 | 49.89 | >500 |
| 8 | 260.6 | >1000 |
| 12 | 44.35 | >500 |

TABLE 2-continued $IC_{50}$ of compounds on BaF3-$EGFR^{L858R/T790M/C797S}$ and A431

| Compound No. | BaF3-$EGFR^{L858R/T790M/C797S}$ ($IC_{50}$ NM) | A431 ($IC_{50}$ NM) |
|---|---|---|
| 13 | 38.12 | >500 |
| 16 | 35.69 | >500 |
| 17 | 45.38 | >500 |
| 19 | 47.78 | >500 |
| 21 | 33.29 | >500 |
| 23 | 38.97 | >500 |
| 32 | 55.37 | 961.5 |
| 24 | 43.28 | >1000 |
| 51 | 131.1 | 745.0 |
| 52 | 236.2 | 606.5 |
| 55 | 48.56 | 700.2 |
| Comparative Compound A | 47.32 | 206.7 |
| Comparative Compound B | 251.4 | 279.8 |

It can be seen from the table above that the compounds of the present invention have excellent in-vitro inhibitory activity against the proliferation of BaF3-$EGFR^{L858R/T790M/C797S}$ cells, while the inhibitory activity thereof against the proliferation of wild-type A431 cells is weak, indicating that the compounds of the present invention have good therapeutic effects on cell proliferative diseases caused by $EGFR^{L858R/T790M/C797S}$ mutations and good selectivity to wild-type EGFR.

TABLE 3

$IC_{50}$ of compounds on BaF3-$EGFR^{del19/T790M/C797S}$ and BaF3-$EGFR^{WT}$

| Compound No. | BaF3-$EGFR^{del19/T790M/C797S}$ ($IC_{50}$ nM) | BaF3-$EGFR^{WT}$ ($IC_{50}$ nM) |
|---|---|---|
| 24 | 128.4 | 5774 |
| 48 | 176.0 | 633.5 |
| 50 | 186.5 | 942.5 |
| 51 | 29.91 | 1182 |
| 52 | 92.79 | 353.4 |
| AZD9291 | 613.8 | 76.14 |
| Comparative Compound A | 66.26 | 1569 |

TABLE 4

$IC_{50}$ of compounds on BaF3-$EGFR^{del19/C797S}$ and BaF3-$EGFR^{L858R/C797S}$

| Compound No. | BaF3-$EGFR^{del19/C797S}$ ($IC_{50}$ nM) | BaF3-$EGFR^{L858R/C797S}$ ($IC_{50}$ nM) |
|---|---|---|
| 24 | 202.5 | 157.5 |
| 54 | 192.6 | 166.1 |
| 51 | 146.1 | 115.8 |
| AZD9291 | >1000 | >1000 |

It can be seen from the table above that the compounds of the present invention have excellent in-vitro inhibitory activity against the proliferation of BaF3-$EGFR^{del19/T790M/C797S}$, BaF3-$EGFR^{del19/C797S}$ and BaF3-$EGFR^{L858R/C797S}$ cells, while the inhibitory activity thereof against the proliferation of wild-type BaF3 cells is weak, indicating that the compounds of the present invention have good therapeutic effects on cell proliferative diseases caused by $EGFR^{del19/T790M/C797S}$, $EGFR^{del19/C797S}$ and $EGFR^{L858R/C797S}$ mutations and good selectivity to wild-type EGFR.

Embodiment 4

BaF3-EGFR$^{T790M/C797S/L858R}$ cell phosphorylation inhibition effect: The compounds of the present invention effectively inhibit the phosphorylation level of EGFR in BaF3-EGFR$^{L858R/T790M/C797S}$ cells (1) Cell Culture Cell line: BaF3 cells with stable overexpression of EGFR$^{T790M/C797S/L858R}$ mutant genes, named BaF3-EGFR$^{T790M/C797S/L858R}$ cells.

A. Mediums

RPMI 1640 and 10% FBS and 50 ng/mL EGF

B. Cell Thawing a) The medium was preheated in a 37° C. water bath.

b) The cryopreservation tube was taken from the liquid nitrogen tank, quickly placed in a 37° C. water bath, and melted completely within 1 minute.

c) The cell suspension was transferred to a 15 mL centrifuge tube containing a 10 mL medium and centrifuged at 1000 rpm for 4 minutes.

d) The supernatant was discarded, the cells were resuspended in a 1 mL medium and transferred to a 55 $cm^3$ culture dish containing a 10 mL medium, 20% serum and 50 ng/mL EGF were administered to the first-generation medium, and culture was conducted in a 37° C. and 5% $CO_2$ incubator.

C. Cell Passage a) The medium was preheated in a 37° C. water bath.

b) The cells in the culture dish were blown evenly with a 5 mL pipette, and 500 μL of the cells were pipetted out to be inoculated into a new 55 $cm^3$ culture dish and cultured in a 37° C. and 5% $CO_2$ incubator.

(2) Compound Preparation a) The compound to be tested (10 mM stock solution) was diluted with 100% DMSO to 1 mM, and diluted with a culture solution in a 24-well plate to prepare of a working solution of 2 μM concentration.

b) The 2 μM working solution was diluted with a triple dilution method to obtain working solutions with approximate concentrations of 2 μM, 600 nM, 200 nM, 60 nM, and 20 nM.

(3) Cell Culture Plate a) The cells at the logarithmic growth phase were centrifuged at 1000 rpm for 4 minutes, resuspended with a medium (containing 10% serum), and counted.

b) The cells were inoculated into a 24-well plate with a cell density of 2 million cells/well, and placed in a 37° C. and 5% $CO_2$ incubator for stabilization overnight. The medium did not contain EGF.

(4) Cell Administration a) The prepared compound was added to a 96-well plate, with 100 μL per well. The final concentrations were 1 μM, 300 nM, 100 nM, 30 nM, 10 nM, and 0 nM, and the final concentration of DMSO was 0.2%. A medium and 0.2% DMSO served as a blank control.

b) 100 ng/mL EGF was added at 1 hour and 45 minutes of administration. After 15 minutes of EGF treatment, the cells were collected and centrifuged to obtain the supernatant.

(5) Detection of Intracellular pEGFR Content

The content of EGFR and pEGFR in the supernatant was determined using an ELISA kit (Abcam, ab126439-EGFR (pY1068)+total EGFR Human ELISA).

(6) Data Analysis

The data was analyzed using GraphPad Prism 8.0 software to obtain a fitted curve of activity of the compounds. The $IC_{50}$ of the compounds was fitted from nonlinear regression equation.

TABLE 5

The effect of compounds on EGFR phosphorylation in Ba/F3-EGFR$^{L858R/T790M/C797S}$ engineered cells

| Compound | Cellular pEGFR Inhibition $IC_{50}$ (nM) Ba/F3-EGFR$^{L858R/T790M/C797S}$ |
|---|---|
| 24 | 150.5 |
| 51 | 132.5 |
| Comparative Compound A | 405.2 |

Both compounds 24 and 51 have a good inhibitory effect on EGFR phosphorylation in Ba/F3-EGFR$^{L858R/T790M/C797S}$ engineered cells.

Embodiment 5 Activity of Other Kinases (1) Preparation of 1× kinase reaction buffer:

1 time the volume of 5× kinase reaction buffer and 4 times the volume of water; 5 mM MgCl2; 1 mM DTT.

(2) Screening of Compounds:

| | Kinase | | Substrate | | ATP |
|---|---|---|---|---|---|
| Kinase | Store Conc.(ng/μL) | Conc.(ng/μL) | | Conc.(μM) | Work Conc.(μM) |
| AURKB | 200 | 0.2 | S2 | 1 | 0.5 |

a) The compound was diluted with DMSO in a dilution plate.

b) The compound was diluted 40 times into the 1× kinase reaction buffer and oscillated on an oscillator for 20 minutes.

c) 2× was prepared using a 1× enzyme reaction buffer.

d) 2 μL of kinase was added to each well of the reaction plate.

e) 1 μL of the compound diluted in the buffer was added to each well, and the plate was sealed with a sealing film, centrifuged at 1000 rpm for 60 seconds and incubated at 25° C. for 10 minutes.

f) A mixture of 2.5×S2 & TK-substrate-biotin and ATP was prepared using the 1× enzyme reaction buffer, and 2 μL of the S2 & TK-substrate-biotin/ATP mixture was added to the reaction plate.

G) The plate was sealed with a sealing film, centrifuged at 1000 rpm for 60 seconds and incubated at 25° C. for 50&40&30&20 minutes.

h) 4× Sa-XL 665 was prepared using an HTRF detection buffer.

i) 5 μL of Sa-XL 665 and 5 μL of STK/TK-antibody-Cryptate were added to each well, centrifugation was conducted at 1000 rpm for 60 seconds, and incubation was conducted at 25° C. for 1 hour.

j) The fluorescence signals at 615 nm (Cryptate) and 665 nm (XL665) were read using the BGM microplate reader.

TABLE 6

| IC$_{50}$ of compounds on Aurora B | |
|---|---|
| Compound No. | Aurora B (IC50 nM) |
| 24 | 410.5 |
| Comparative Compound A | 2010 |

It can be seen from the table above that the compounds of the present invention have good in-vitro inhibitory activity against Aurora B kinase. Targeting the Aurora B kinase can prevent and overcome the resistance of lung cancer to EGFR inhibitors, indicating that the compounds of the present invention have a synergistic anti-tumor mechanism and the potential to overcome the resistance of lung cancer to EGFR inhibitors.

Embodiment 6

Stability testing of liver microsomes: The compounds of the present invention have good stability in humans, monkeys, and mice 1. 100 mM K-buffer was preheated with 5 mM $MgCl_2$ with a pH value of 7.41.
2. Preparation of testing solution 0.5 mM solution A: 5 μL of the 10 mM compound stock solution was added for reference to 95 μL of ACN.

1.5 μM microsome solution (0.75 mg/mL): 1.5 μL of a 500 μM solution and 18.75 μL of 20 mg/mL liver microsomes were added to 479.75 μL of K/Mg-buffer.

3. The K/Mg-buffer NADPH solution (6 mM, 5 mg/mL) was prepared.
4. 30 μM of human, monkey, and mouse liver microsomes with a 0.75 mg/mL concentration were added to detection plates at different time points (0, 15, 30, 45, and 60 minutes).
5. Pre-incubation was conducted at 37° C. for 5 minutes.
6. At 0 min, before 15 μL of the NADPH stock solution (6 mM) was added, 150 μL of ACN containing IS was added.

NADPH was dissolved in the K/mg buffer to prepare a 6 mm and 5 mg/mL NADPH stock solution.

7. At other time points, 15 μL of the NADPH stock solution (6 mM) was added to the well for starting the reaction and timing.
8. 150 μL of ACN containing IS was added to the corresponding plate wells at 15 min, 30 min, 45 min, and 60 min, respectively, and the reaction was stopped.
9. After quenching, shaking well was conducted for 10 minutes (600 rpm), and centrifugation was conducted at 6000 rpm for 15 minutes.

10. 80 μL of the supernatant in each well was transferred to a 96-well sample plate (containing 140 μL of pure water) for LC/MS analysis.

TABLE 7

| Experimental results of stability of compounds on liver microsomes of different species | | | |
|---|---|---|---|
| Compound No. | Species | $T_{1/2}$ (minute) | $Cl_{int}$ (mL/min/kg) |
| 24 | human | >145 | <9.6 |
| | monkey | 50.0 | 27.7 |
| | mouse | >145 | <9.6 |
| Comparative Compound A | human | 27.8 | 49.84 |
| | monkey | 26.7 | 52.0 |
| | mouse | 76.1 | 18.2 |

Experimental conclusion: Compound 24 has good stability in liver microsomes of humans, monkeys, and mice, and the metabolic stability thereof is better than that of comparative compound A.

Embodiment 7

Detection of oral plasma exposure in rats: The compounds of the present invention have good oral in-vivo exposure in rats After a single dose of 10 mg/kg oral administration of the compound to be tested in SD rats, blood samples were collected at different time points.

Standard curve and quality control sample preparation processing: The mixed reserve solution of the compound to be tested was taken and diluted with 50% methanol water into standard working solutions containing respective compounds with concentrations of 20, 40, 100, 200, 400, 1000, 2000, 4000, 10000, and 20000 ng/mL, as well as 60, 600, and 16000 ng/mL quality control working solutions. 47.5 μL of a blank matrix was taken. 2.50 μL of the standard curve working solutions and the quality control working solutions were added to prepare standard curves containing respective compounds with concentrations of 1.00, 2.00, 5.00, 10.00, 20.00, 50.00, 100.00, 200.00, 500.00, and 1000.00 ng/mL, as well as quality control samples with concentrations of 3.00, 30.00, and 800.00 ng/mL, respectively. 400 μL of acetonitrile (containing internal standard Verpmil of 2 ng/mL) was added. After vortex oscillation at 700 rcf for 10 minutes, centrifugation was conducted at 3300 rcf at 4° C. for 10 minutes. The supernatant was taken for LC-MS/MS analysis.

Unknown sample preparation processing: 50 μL of the sample to be tested was taken. 400 μL of acetonitrile (containing internal standard Verpmil of 2 ng/mL) was added. After vortex oscillation at 700 rcf for 10 minutes, centrifugation was conducted at 3300 rcf and 4° C. for 10 minutes. The supernatant was taken for LC-MS/MS analysis.

TABLE 7

| Detection results of oral plasma exposure of rats. | | | | | | |
|---|---|---|---|---|---|---|
| compound | Administration | $T_{1/2}$ (h) | $T_{max}$ (h) | $C_{max}$ (ng/mL) | $AUC_{last}$ (h*ng/mL) | $AUC_{INF\_obs}$ (h*ng/mL) |
| 6 | p.o.(10 mg/kg) | 9.72 | 8.00 | 865.65 | 13809.34 | 17680.19 |
| 12 | p.o.(10 mg/kg) | NA | NA | 1188.81 | 15926.09 | 1592.61 |
| 24 | p.o.(10 mg/kg) | 9.48 | 9.00 | 504.94 | 7873.97 | — |
| 51 | p.o.(10 mg/kg) | 9.47 | 4.00 | 1221.72 | 20712.85 | — |

From the above table and FIG. 1, it can be seen that the compounds of the present invention have a good oral in-vivo exposure and have the potential for oral administration.

Embodiment 8

In-vivo efficacy: The compounds of the present invention have excellent in-vivo anti-tumor efficacy and are dose-dependent In-vivo efficacy experiments were conducted on BALB/c nude mice subcutaneously implanted with Ba/F3-$EGFR^{L858R/T790M/C797S}$ derived xenograft (CDX). BALB/c nude mice, female, 6-8 weeks old, weighing approximately 18-22 grams, were raised in an SPF-level environment with separate ventilation for each cage (5 mice per cage). All cages, beddings, and water were disinfected before use. All the animals were free to access standard certified commercial laboratory diets. A total of 48 mice were purchased from Beijing Vital River for research. Each mouse was subcutaneously implanted with histiocytes in the right axilla for tumor growth. The experiment began when the average tumor volume reached about 70 cubic millimeters. The experimental compounds were for oral administration daily, with compound 24 (45 mg/kg, 75 mg/kg respectively) and compound 51 (100 mg/kg) administered continuously for 13 days. The data are listed in Table 8:

TABLE 8

| Therapeutic effects of compounds on Ba/F3-$EGFR^{L858R/T790M/C797S}$ nude mouse transplantation tumors | | |
|---|---|---|
| Compound | Dose | TGI % |
| 24 | 45 mg/kg/day | 84.74 |
| 24 | 75 mg/kg/day | 99.06 |
| 51 | 100 mg/kg/day | 83.07 |

The compounds of the present invention can effectively inhibit tumor growth in Ba/F3-$EGFR^{L858R/T790M/C797S}$ nude mouse transplantation tumor models, where compound 24 has a TGI of 84.74% and 99.06% at doses of 45 mg/kg/day and 75 mg/kg/day, respectively, and compound 51 has a TGI of 83.07% at a dose of 100 mg/kg/day.

In summary, the compounds of the present invention have broad application prospects for EGFR mutant diseases.

What is claimed:

1. A compound, having a structure represented by formula I:

formula I

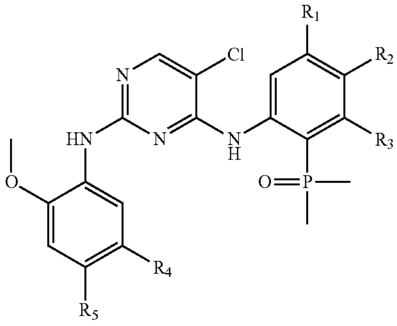

or being an isomer of the structure represented by formula I or a pharmaceutically acceptable salt thereof;

wherein $R_1$, $R_2$, and $R_3$ are each independently selected from H, Cl, $C_{1-3}$ alkyl, and $CF_3$;

$R_4$ is selected from H, halogens, and $C_{1-3}$ alkyl;

$R_5$ is selected from

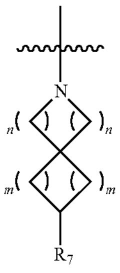
,
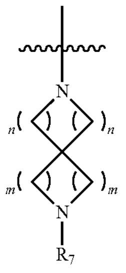
, and
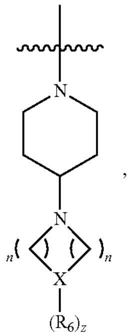
, where m and n are each independently selected from 1 and 2, Z is selected from 0 or 1, and X is selected from N, O, and CH;

$R_6$ is selected from H, $C_{1-3}$ alkyl, and $C_{1-3}$ alkyl substituted amino;

$R_7$ is selected from $C_{1-6}$ alkyl, $C_{1-6}$ cycloalkyl, amino, and $C_{1-6}$ alkoxy, wherein the amino is optionally substituted by 1 or 2 $C_{1-6}$ alkyls or $C_{1-6}$ cycloalkyl, and the $C_{1-6}$ alkyl and the $C_{1-6}$ alkoxy are each optionally substituted by 1 or more $C_{1-6}$ cycloalkyls, halogens, oxo, hydroxyl, or cyano; when X is O, z is 0;

R1, R2, and R3 are not H at the same time, and when one of R1, R2, and R3 is selected from $CH_3$, at most one of the other two of R1, R2, and R3 is selected from H;

when both $R_2$ and $R_3$ are $CH_3$, $R_5$ is not selected from

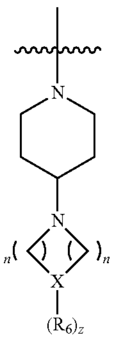

;

when $R_4$ is Cl, $R_5$ is not selected from

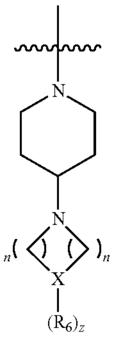

, and when $R_3$ is H, both $R_1$ and $R_2$ are $CH_3$ or both $R_1$ and $R_2$ are Cl.

2. The compound according to claim 1, wherein $R_1$ is H;

$R_2$ and $R_3$ are each independently selected from Cl and $CH_3$;

$R_4$ is selected from H, halogens, $CH_3$, and $CH_2CH_3$.

3. The compound according to claim 1, having a structure represented by formula II or formula III:

formula II

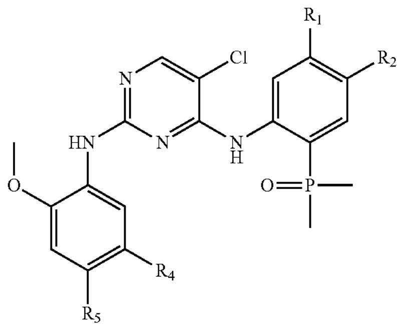

-continued formula III

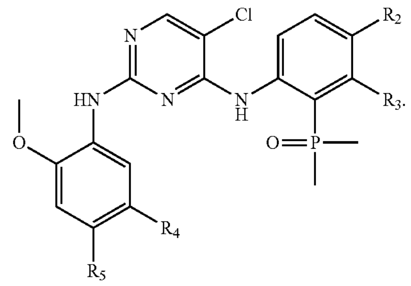

4. The compound according to claim 1, having a structure represented by formula IV:

formula IV

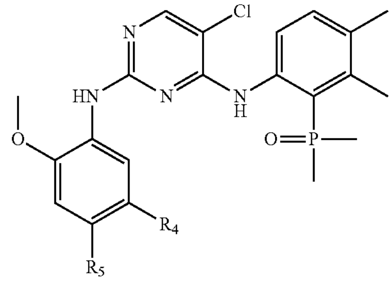

or being an isomer of the structure represented by formula IV or a pharmaceutically acceptable salt thereof;

$R_4$ is selected from $C_{1-3}$ alkyl;

$R_5$ is selected from

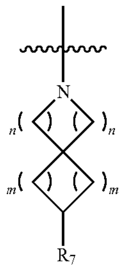

and

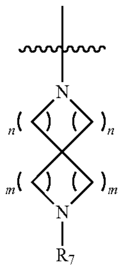

, where m and n are each independently selected from 1 and 2;

$R_7$ is selected from $C_{1-3}$ alkyl and

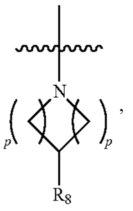

, where p is selected from 1 and 2; and $R_8$ is selected from H and cyano.

5. The compound according to claim 1, wherein $R_5$ is selected from:
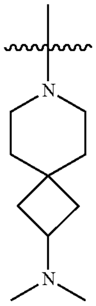, 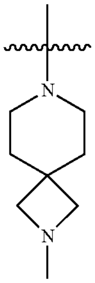, 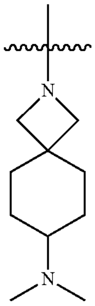, 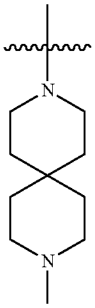, 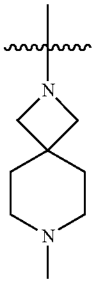,
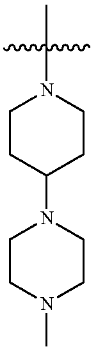, 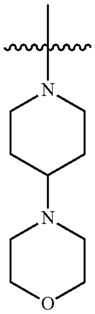, 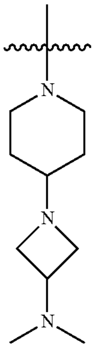, 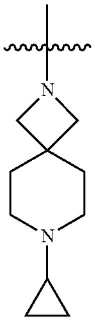,
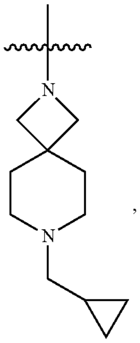, 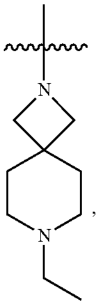, 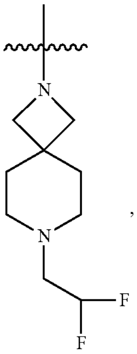, 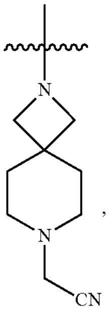,
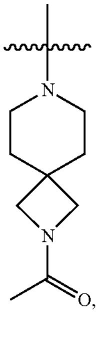, 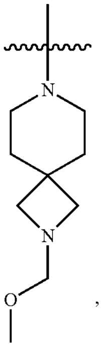, 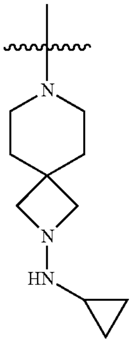, 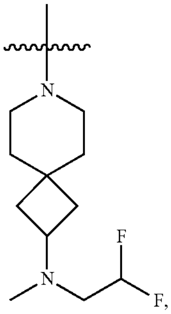,
-continued
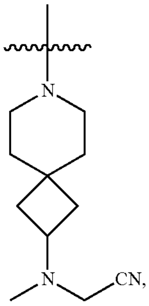, 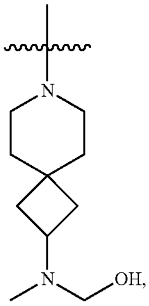, 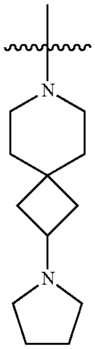, 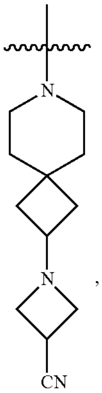,
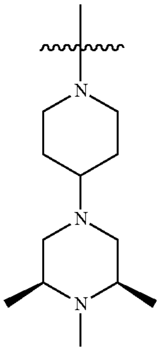, 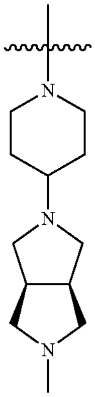, 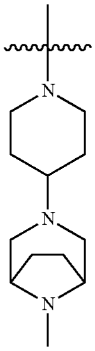,
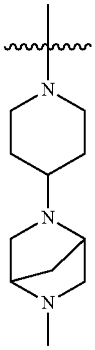, and 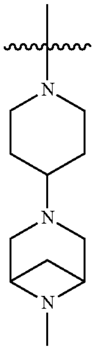.

6. A compound selected from:
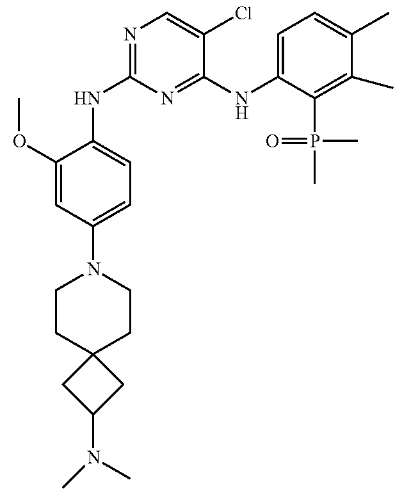
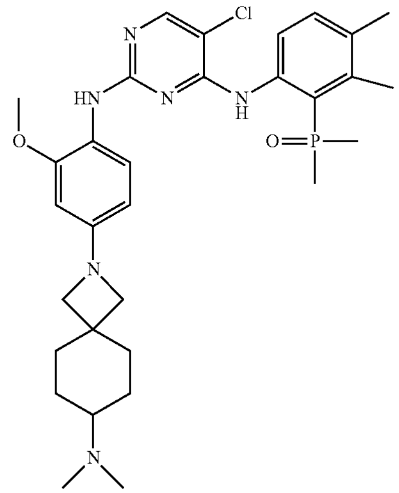
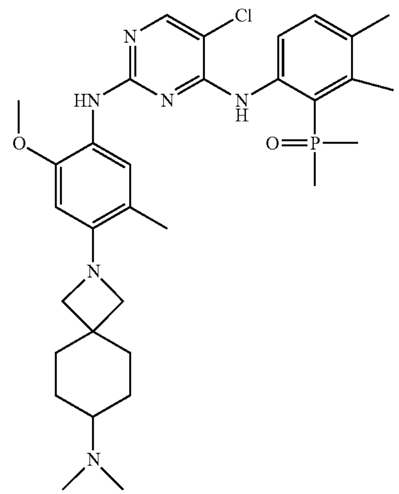
-continued
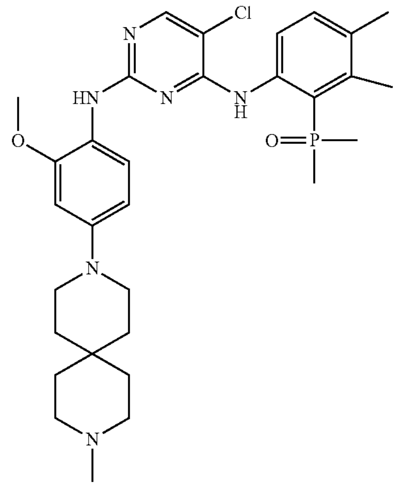
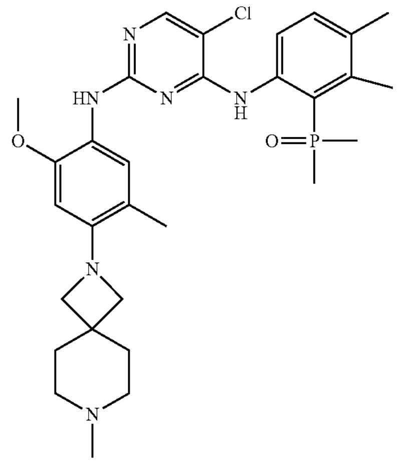
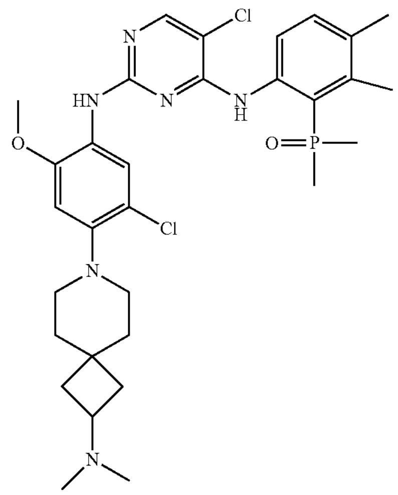

-continued
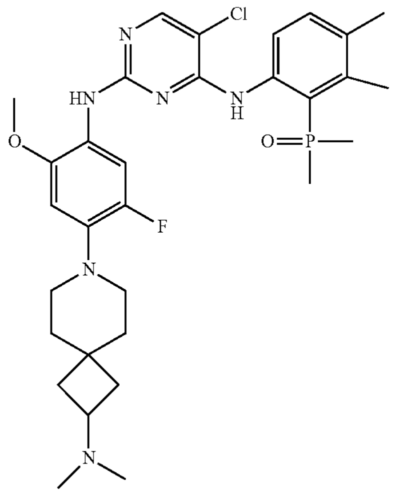
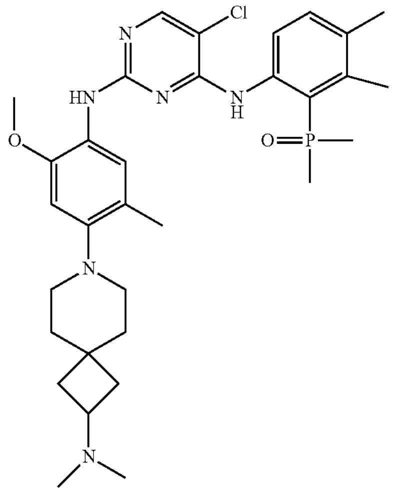
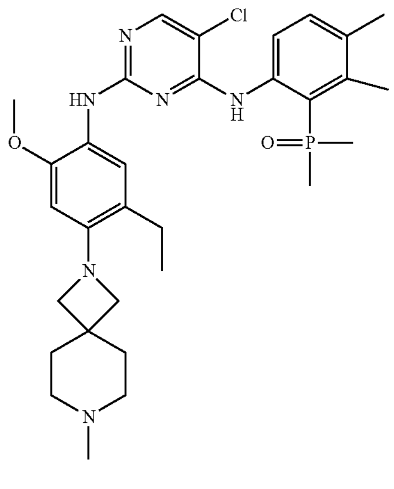
-continued
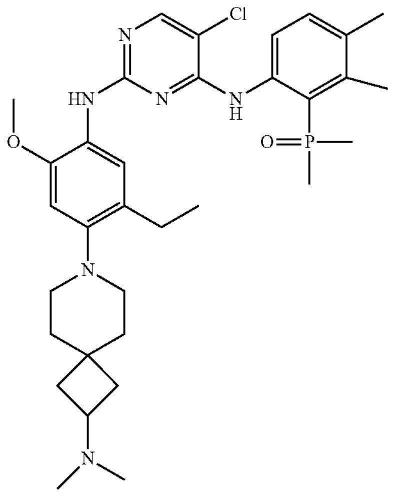
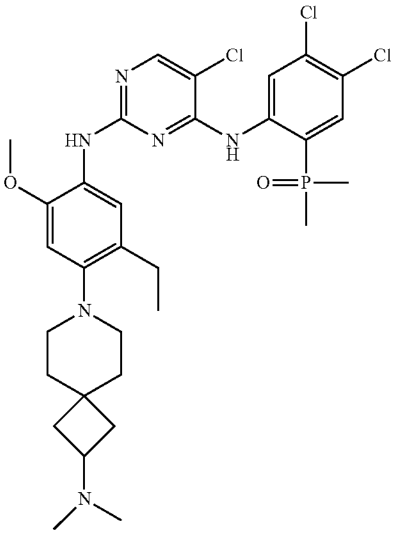
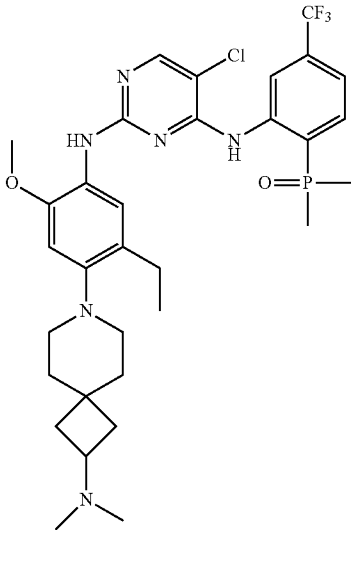

-continued
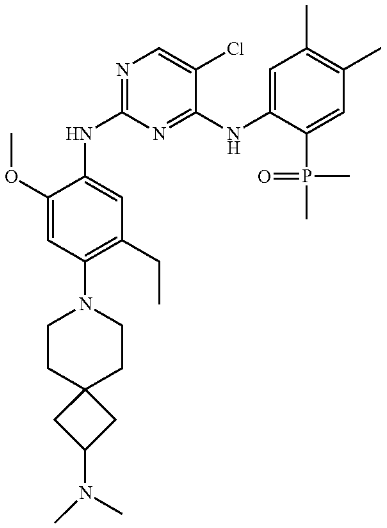
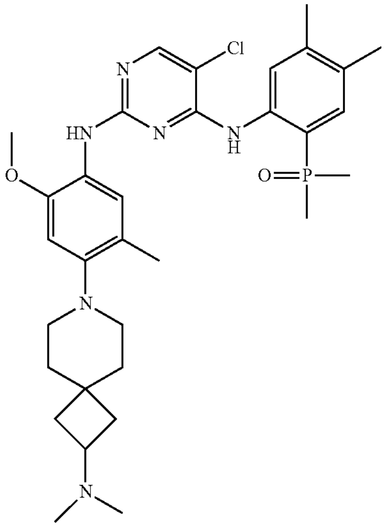
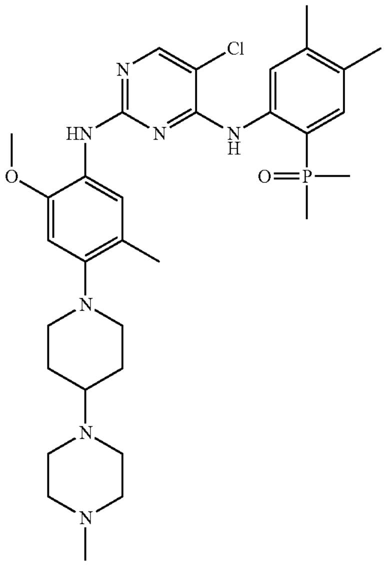
-continued
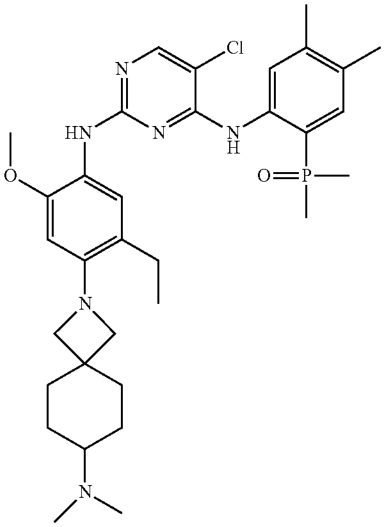
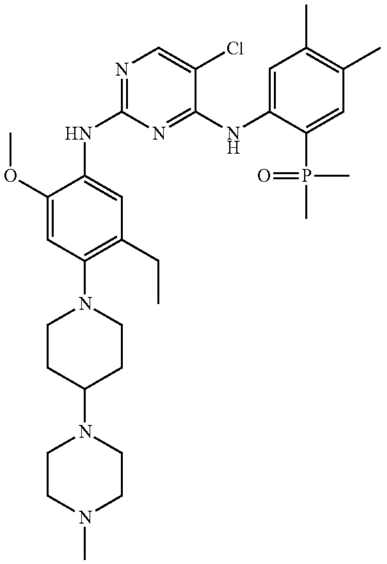
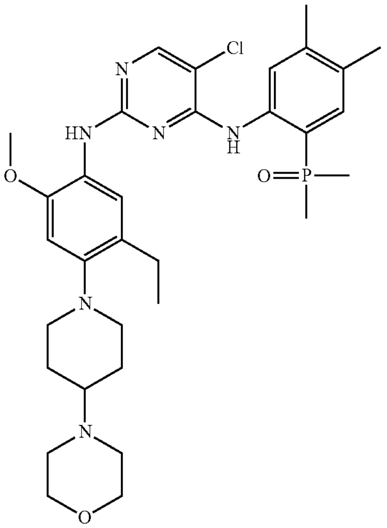

-continued
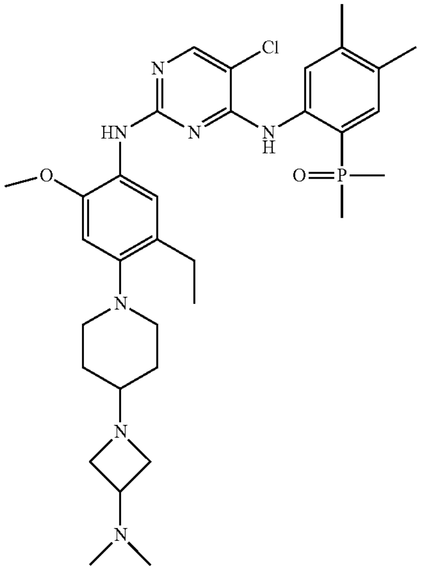
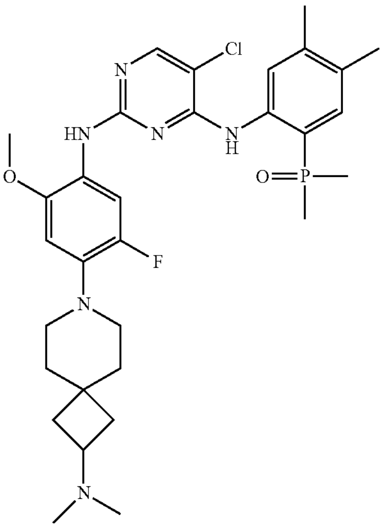
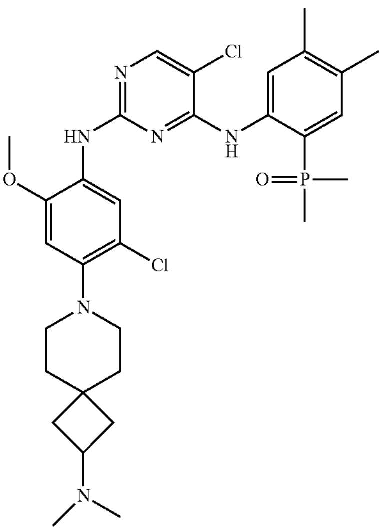
-continued
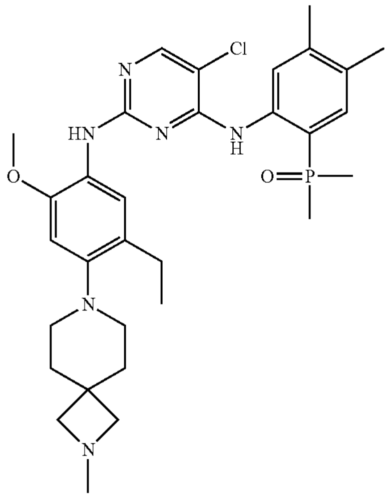
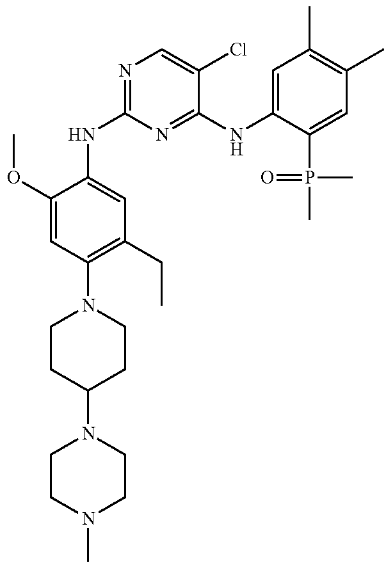
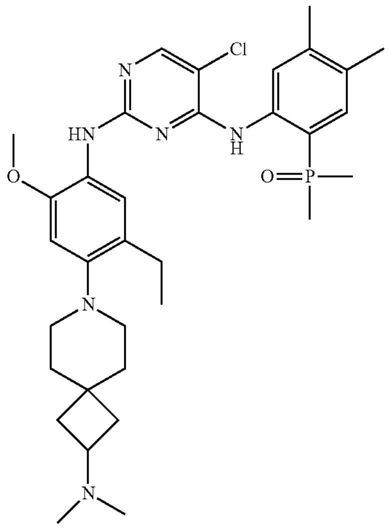

-continued
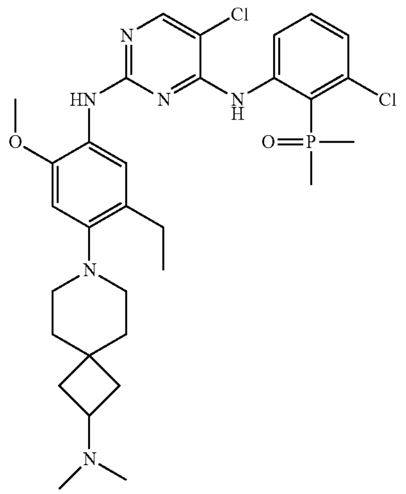
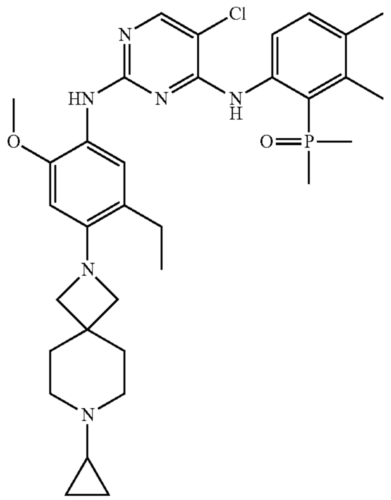
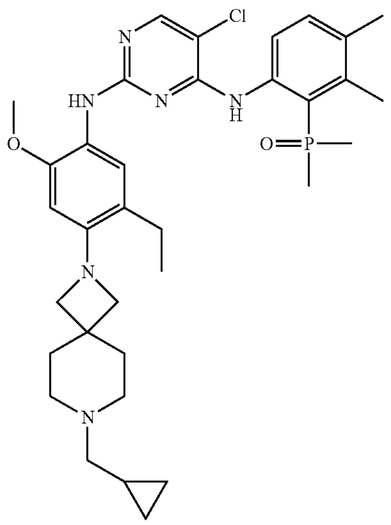
-continued
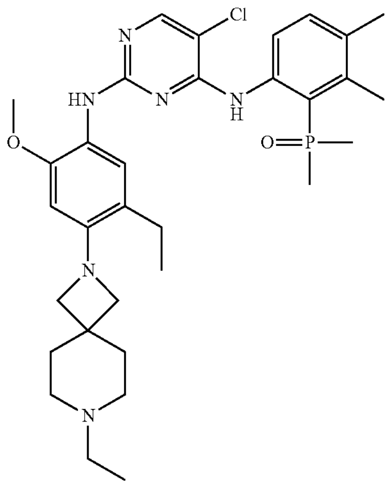
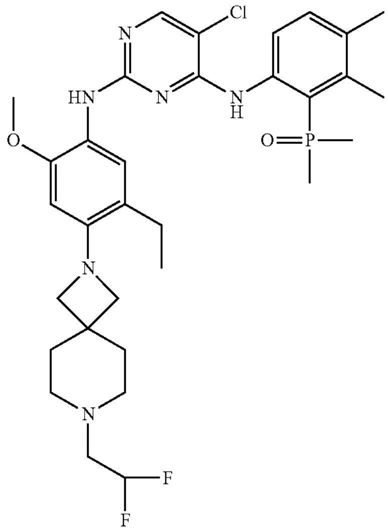
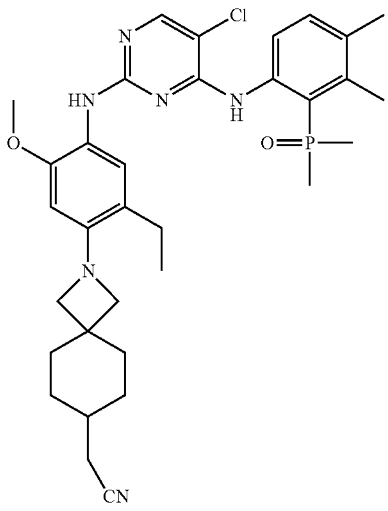

-continued
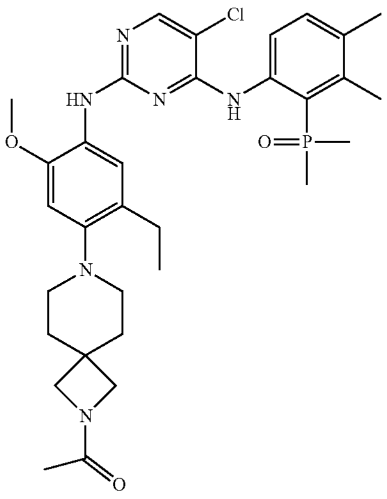
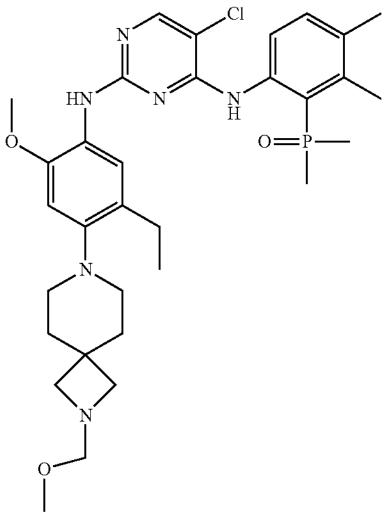
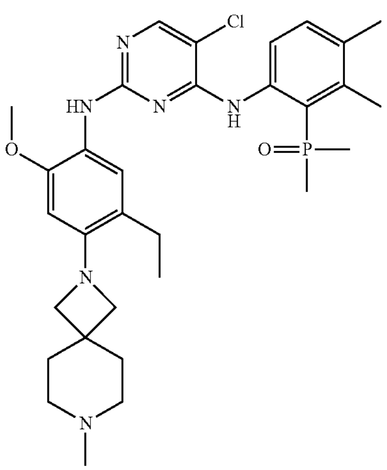
-continued
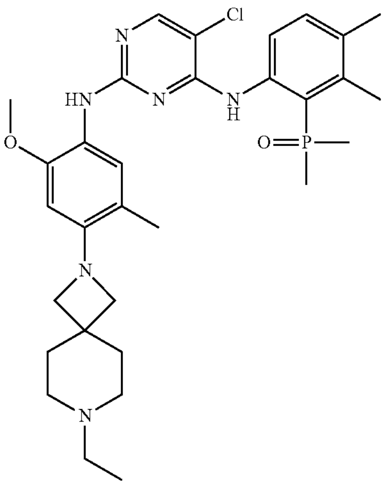
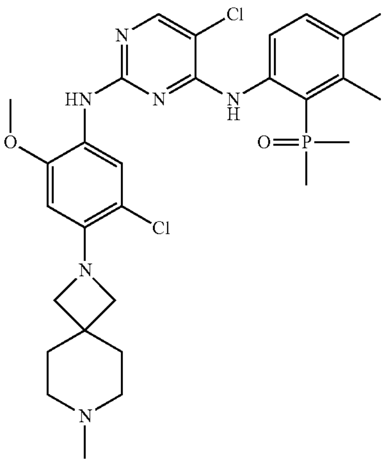
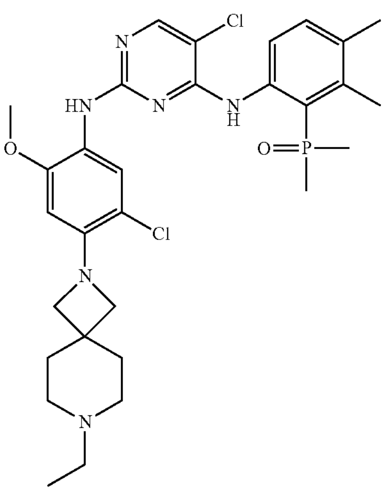

-continued
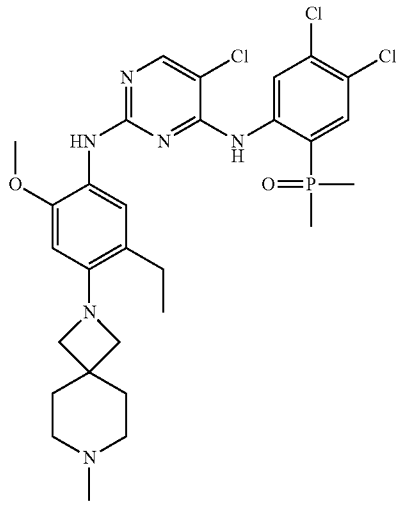
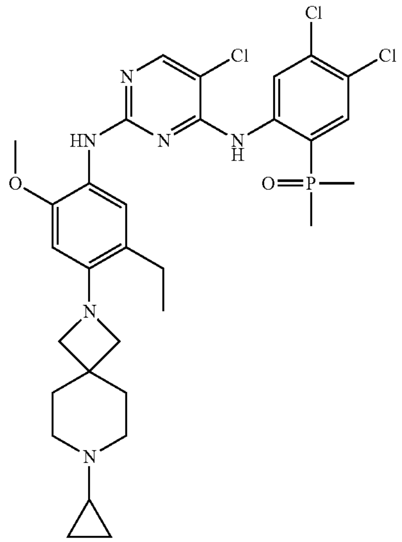
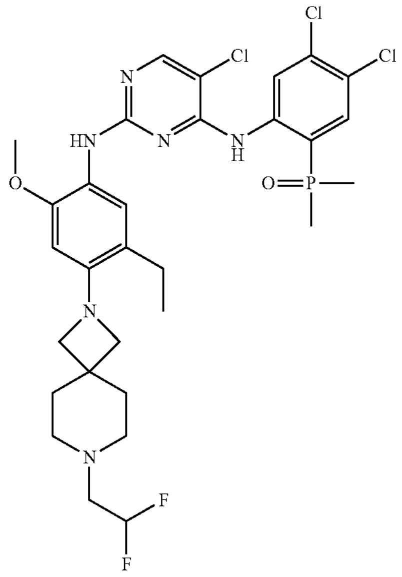
-continued
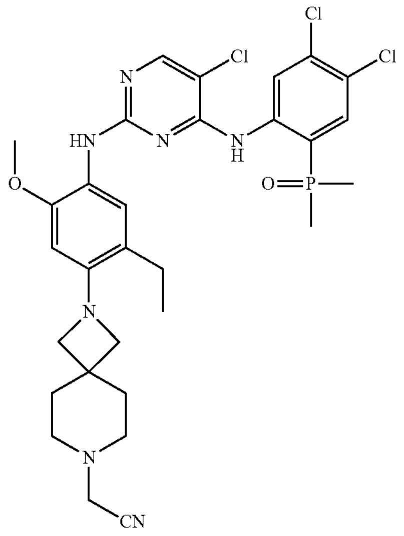
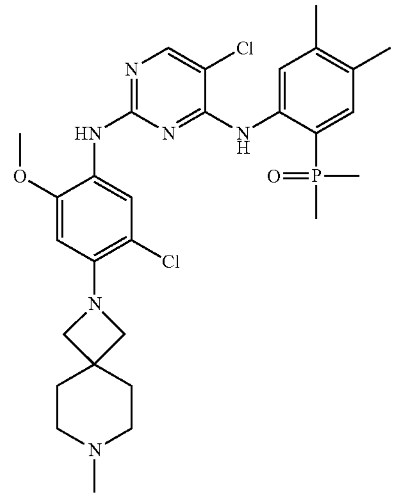
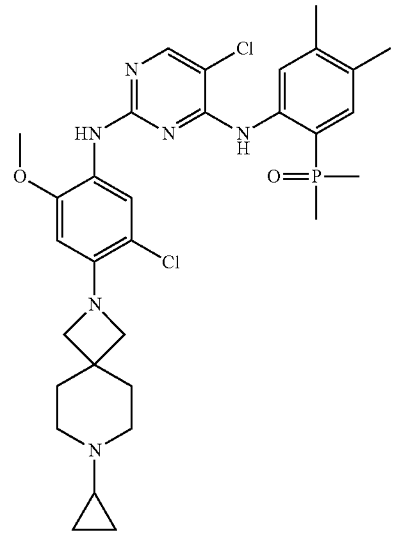

-continued
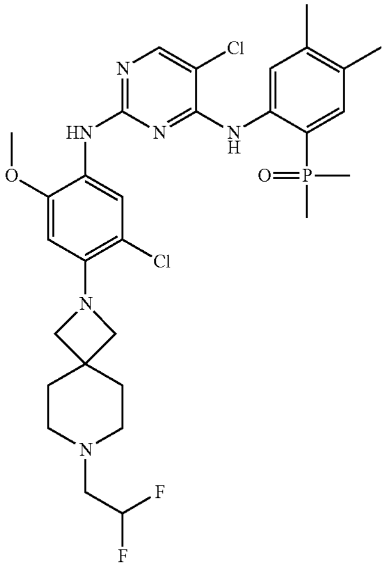
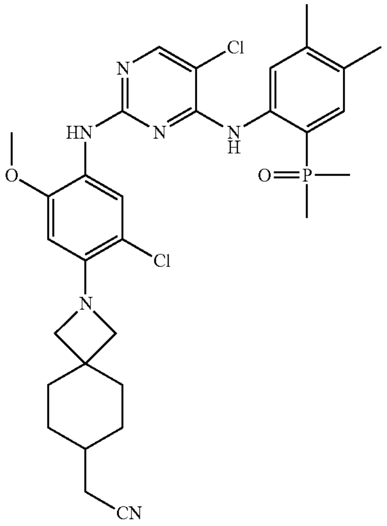
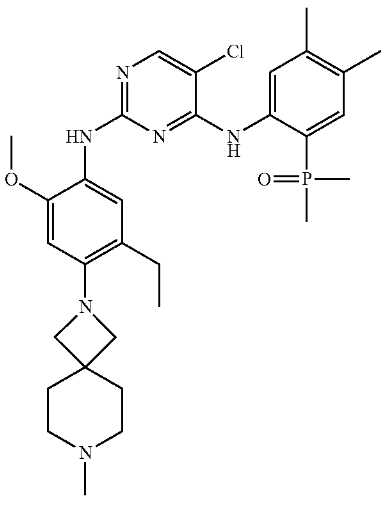
-continued
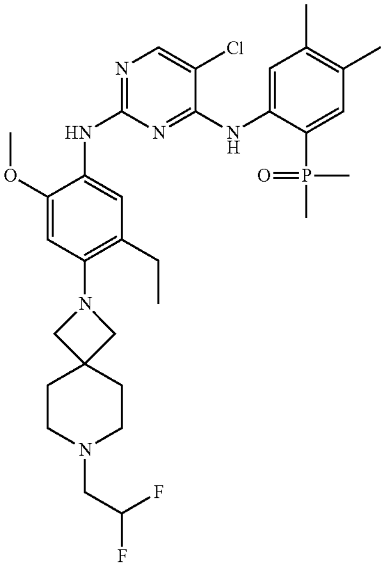
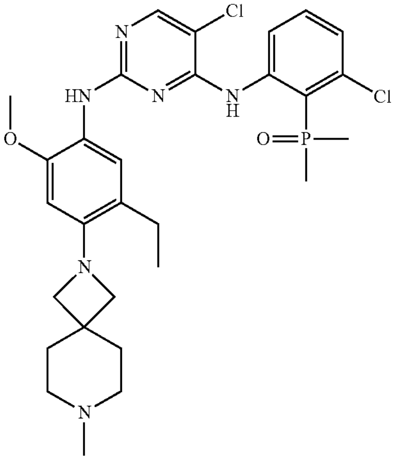
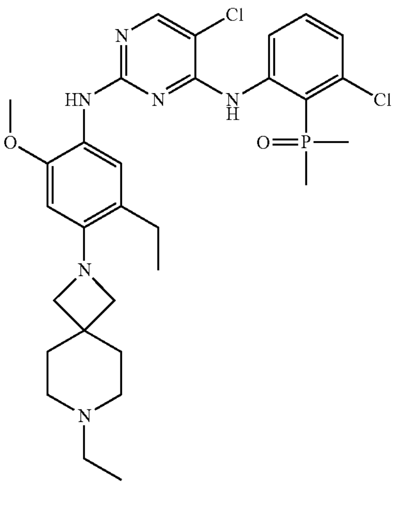

-continued
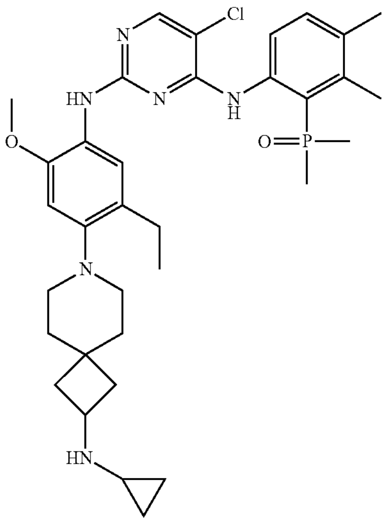
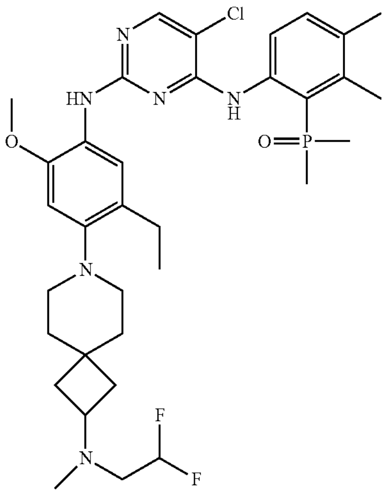
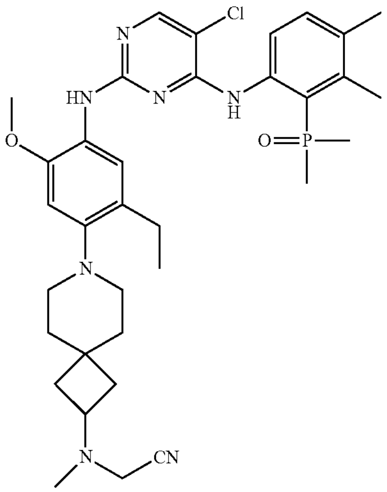
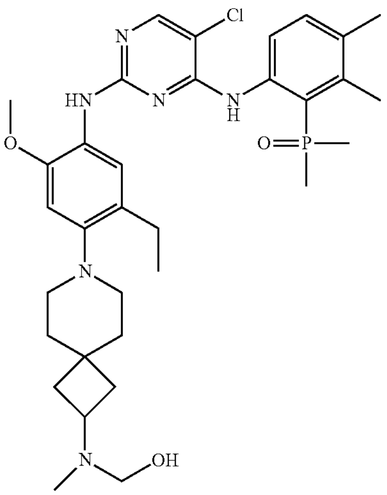
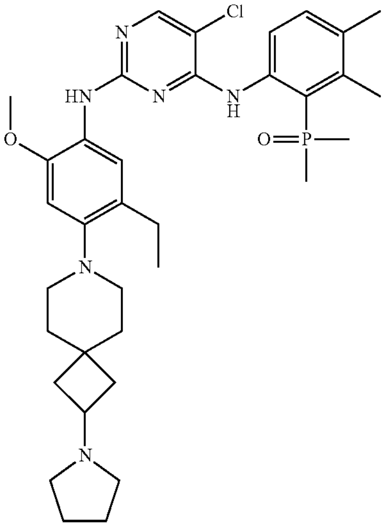
-continued
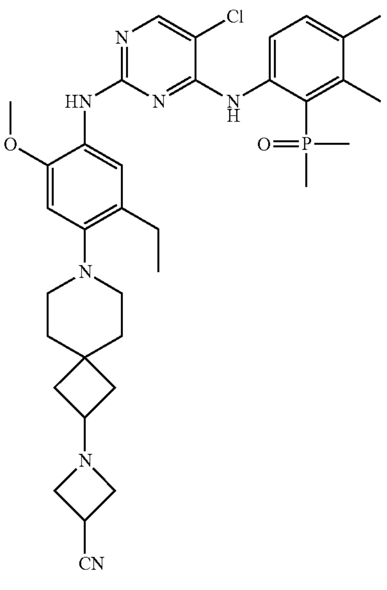

-continued
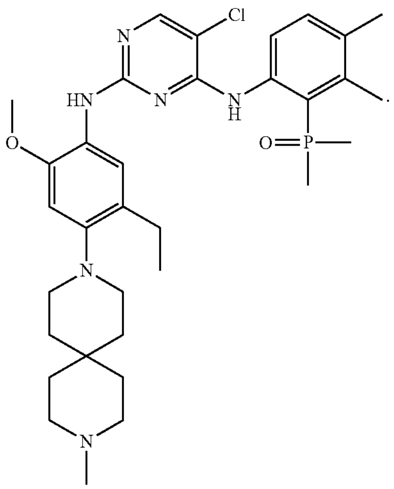 [SMILES: CCc1cc(Nc2ncc(Cl)c(Nc3ccc(C)c(C)c3P(C)(C)=O)n2)c(OC)cc1N1CCC2(CCN(C)CC2)CC1]
7. A compound selected from:
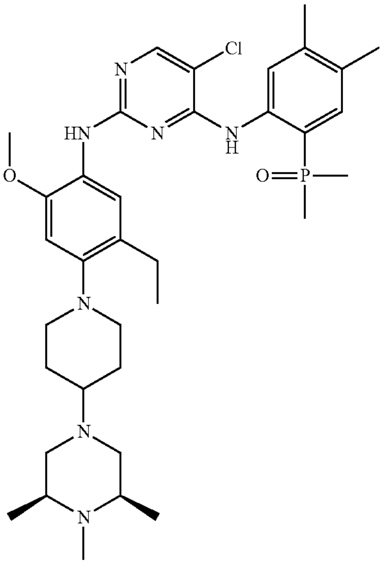
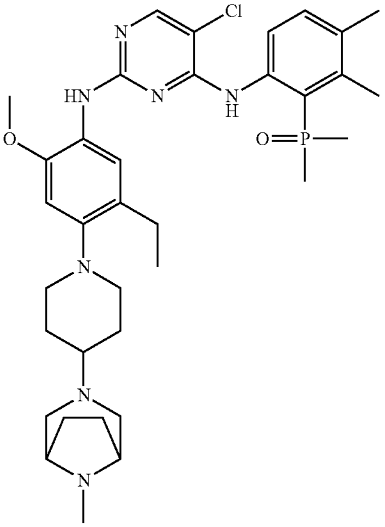
-continued
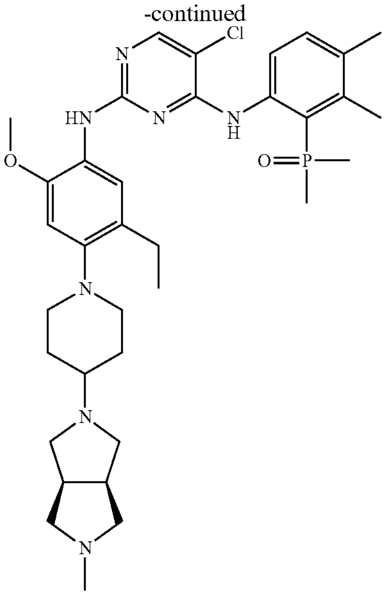
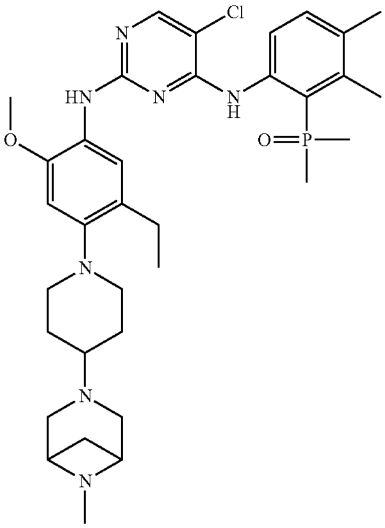
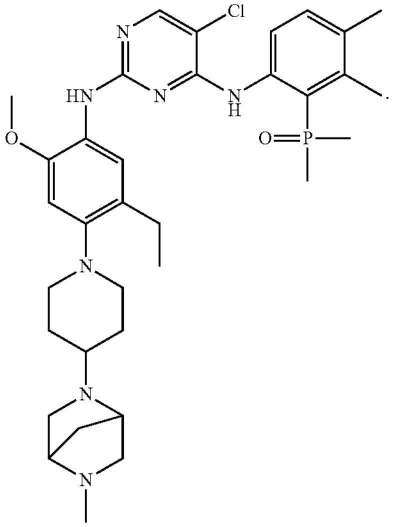
8. A pharmaceutical composition, comprising the compound according to claim 6, an isomer thereof, or a pharmaceutically acceptable salt thereof.

9. A pharmaceutical composition, comprising the compound according to claim 7, an isomer thereof, or a pharmaceutically acceptable salt thereof.

* * * * *